US005559223A

United States Patent [19]

Falco et al.

[11] Patent Number: 5,559,223
[45] Date of Patent: Sep. 24, 1996

[54] SYNTHETIC STORAGE PROTEINS WITH DEFINED STRUCTURE CONTAINING PROGRAMMABLE LEVELS OF ESSENTIAL AMINO ACIDS FOR IMPROVEMENT OF THE NUTRITIONAL VALUE OF PLANTS

[75] Inventors: Saverio C. Falco, Arden; Sharon J. Keeler, Newark; Janet A. Rice, Wilmington, all of Del.

[73] Assignee: E. I. DuPont de Nemours and Company, Wilmington, Del.

[21] Appl. No.: 182,175

[22] PCT Filed: Aug. 7, 1992

[86] PCT No.: PCT/US92/06412

§ 371 Date: Feb. 3, 1994

§ 102(e) Date: Feb. 3, 1994

[87] PCT Pub. No.: WO93/03160

PCT Pub. Date: Feb. 18, 1993

[51] Int. Cl.$^6$ .......................... C12N 15/11; C12N 15/82; A01H 5/00
[52] U.S. Cl. .................... 536/23.1; 435/69.1; 435/172; 435/3; 435/240.4; 435/320.1; 800/205; 800/DIG. 70; 935/10; 935/64
[58] Field of Search ........................ 800/205, DIG. 70; 536/23.1; 435/69.1, 320.1, 240.4, 172.3; 935/10, 64

[56] References Cited

FOREIGN PATENT DOCUMENTS

| 0208418 | 1/1987 | European Pat. Off. ........ C12N 15/00 |
| 0318341 | 5/1989 | European Pat. Off. ........ C12N 15/00 |
| 0319353 | 6/1989 | European Pat. Off. ........ C12P 12/02 |
| WO89/04371 | 5/1989 | WIPO ............................ C12P 21/00 |
| WO91/10725 | 7/1991 | WIPO ............................ C12N 5/00 |

OTHER PUBLICATIONS

Hodges, R. S. et al, *J. Biological Chem.*, 256(3), 1214–1224 (1981).
Altenbach et al, *J. Cell. Bioch.*, Supp. 15A, p. 87 (Jan. 10–17, 1991) Abstract A 400.
Cohen, C. et al, *Trends in Biochemical Sciences*, 11(6). 245–248 (1986).
Kim et al, *J. Cell. Bioch.*, Supp. 14E, p. 349 (Apr. 16–22, 1990) Abstract R 514.
Altenbach, S. B. et al, *Trends in Biotechnology*, 8(6), 156–160 (1990).
Declerq, A. et al, *Plant Physiology*, 94, 970–979 (1990).
Powell, T. S. et al, *Poult. Science*, 55, 502–509 (1976).
Mounts et al In Soybean: Improvement, Production & Uses 2nd Edition (Wilcox, ed.) (1987) vol. 16 pp. 822–823 and 850–853.
Ensminger, M. E. et al, *Feeds and Nutrition*, The Ensminger Publishing Co., Clovis, CA (1978) p. 873.
Pedersen, K. et al, *J. Biol. Chem.*, 261(14), 6279–6284 (1986).
Kirihara, J. A. et al, *Mol. Gen. Genet.*, 21, 477–484 (1988).
Kirihara et al, *Gene*, 71, 359–370 (1988).

Higgins, T. J. V. et al, *J. Biol. Chem.*, 261, 11124–11130 (1986).
Altenbach, S. B. et al, *Plant Mol. Biol.*, 8, 239–250 (1987).
Masumura, T. et al, *Plant Mol. Biol.*, 12, 123–130 (1989).
Deutscher, D., *Adv. Exp. Medicine and Biology*, 105, 281–300 (1978).
Mertz, E. T., *Science*, 145, 279–280 (1964).
Natl. Res. Council Report (1988), Quality Protein Maize. National Acad. Press, Wash. DC pp. 1–81.
Vasal, S. K. (1974). Symposium Proceedings. Worldwide Maize Improvement in the 70's and the Role for CIMMYT. Centro Internacional de Mejoramiento de Maiz y Trigo. El Batan, Mexico pp. 10–1 to 10–28.
Vasal, S. K. et al, Proceedings of the 3rd Seed Protein Symposium, Gatersleben, (held Aug. 31–Sep. 2, 1983) In Die Kulturpflanze (Muntz et al, eds) vol. 32/1 pp. S171–S184 (1984).
Burton J. W., 1984 World Soybean Research Conf. III Proceedings (R. Shibles, Editor), pp. 361–368, Aug. 12–17, 1984.
Chee, P. P. et al, *Plant Physiol.*, 91, 1212–1218 (1989).
Christou, P. et al, *Proc. Nat. Acad. Sci USA*, 86, 7500–7504 (1989).
Hinchee, M. A. W. et al, *Biotechnology*, 6, 915–922 (1988).
DeBlock, M. et al, *Plant Physiol.*, 91, 694–701 (1989).
Gordon–Kamm, W. J. et al, *Plant Cell*, 2, 603–618 (1990).
Fromm, M. E. et al, *Biotechnology*, 8, 833–839 (1990).
Goldberg, R. B. et al, *Cell*, 56, 149–160 (1989).
Sengupta–Gopalan, C. et al, *Proc. Natl. Acad. Sci. USA*, 82, 3320–3324 (1985).
Barker, S. J. et al, *Proc. Natl. Acad. Sci. USA*, 85, 458–462 (1988).
Ellis, J. R. et al, *Plant Mol. Biol.*, 10, 203–214 (1988).
Naito, S. et al, *Plant. Mol. Biol.*, 11, 109–123 (1988).
Hoffman, L. M. et al, *Plant Mol. Biol.*, 11, 717–729 (1988).
Altenbach, S. B. et al, *Plant Mol. Biol.*, 13, 513–522 (1989).
Bednareket, S. Y. et al, *The Plant Cell*, 2, 1145–1155 (1990).
Munro, S. et al, *Cell*, 48, 899–907 (1987).
Pelham, H. R. B., *EMBO J.*, 7(4), 913–918 (1988).
Pelham, H. R. B. et al, *EMBO J.*, 7(6). 1757–1762 (1988).
Inohara, N. et al, *Proc. Natl. Acad. Sci. USA*, 86, 3564–3568 (1989).
Hesse, T. et al, *EMBO J.*, 8(9), 2453–2461 (1989).
Lawton, M. A. et al, *Plant. Mol. Biol.*, 9, 315–324 (1987).
Ueng, P. et al, *Plant Physiol.*, 86, 1281–1285 (1988).

(List continued on next page.)

*Primary Examiner*—Patricia R. Moody

[57] ABSTRACT

There is provided synthetic nucleic acid fragments for the altered expression of selected nutritionally-important proteins in plants. These nucleic acid fragments may be used to transform plants, particularly crop plants, to increase the lysine and methionine content of seeds or leaves. The invention is of significant interest for the nutritional improvement of corn which is low in lysine and sulfur amino acid-poor plants, such as corn and soybean. There is also provided chimeric genes, host cells, plants, seeds and microorganisms containing the nucleic acid fragment as well as methods for obtaining the expression of particular proteins in plants and microorganisms.

18 Claims, 12 Drawing Sheets

OTHER PUBLICATIONS

Williamson, J. O. et al, *Plant Physiol.*, 88, 1002–1007 (1988).
Hoffman, L. M. et al, *EMBO J*, 6, 3213–3221 (1987).
Yang, M. S. et al, *Plant Science*, 64, 99–111 (1989).
Nelson, O. E., *Science*, 150, 1469–1470 (1965).
Jaynes et al 1985 Appl. Microbiol. Biotechnol 21:200–205.
Wilkins et al 1990 (Apr.) The Plant Cell 2:301–313.
Della–Cioppa et al 1987 Plant Physiol 84:965–968.
Rosenberg et al 1987 Gene 56:125–135.
Jaynes et al. 1986 Trends in Biotechnology 4:314–320.
Shoemaker et al 1987 Nature 326:563–567.

FIG. 2A
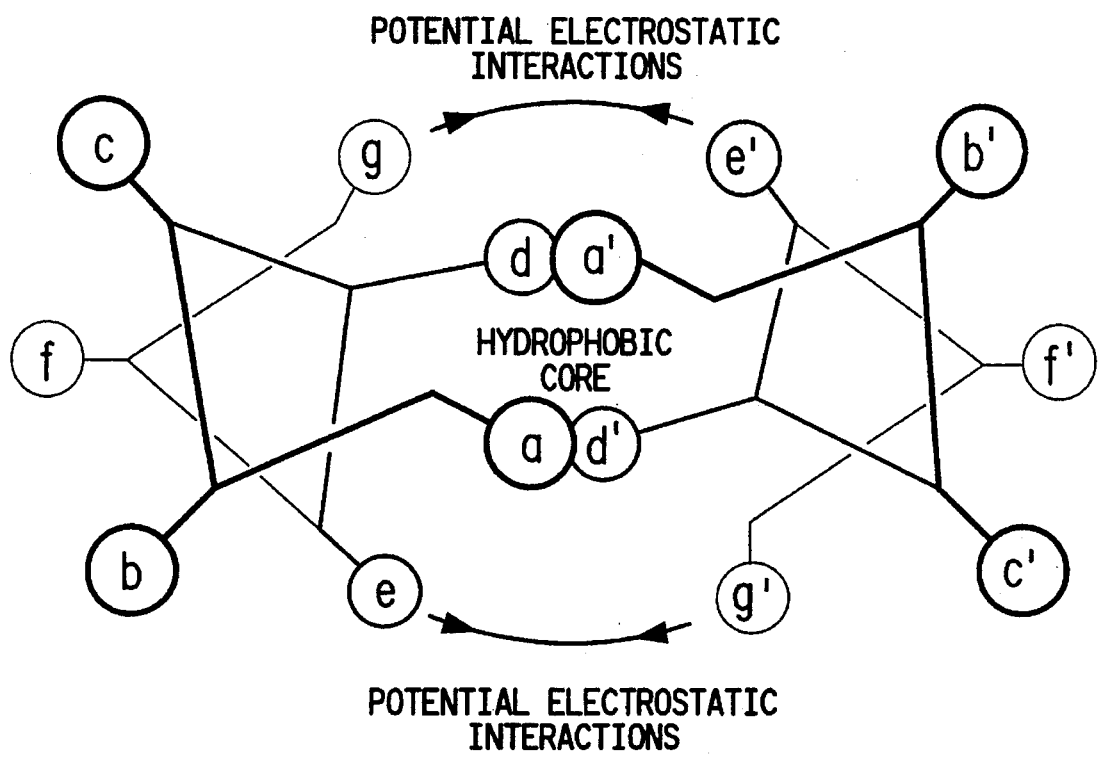
FIG. 2B
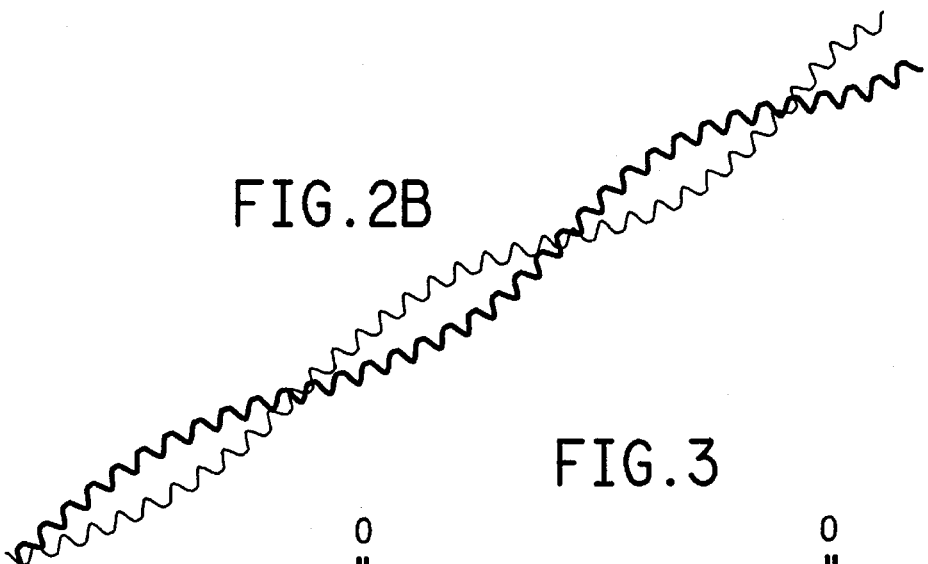
FIG. 3
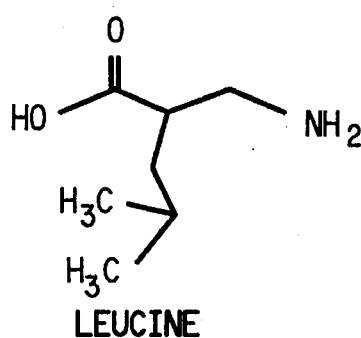
LEUCINE
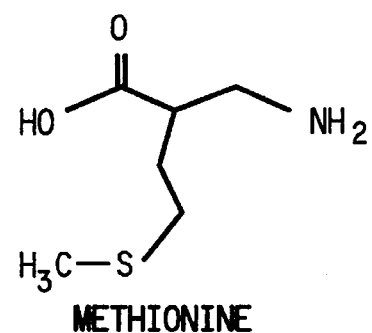
METHIONINE

FIG. 8

```
       NCOI                EARI          BSPHI  STOP  ASP718  ECORI           BASE GENE
      ┌─────┐            ┌──────┐       ┌─────┐      ┌───────┐
      │CATG│GAGGAGAAGATGAAAAA GCTC│GAAGAG│AAGATGAAGG│TCATGA│GTGA│AGGTACC│G
       GTAC CTCCTCTTCTACTTTTTCTA      GCTTCTCTTCTACTTCC AGTACT CACT TCCATGG CTTAA
        M   E  E  K  M  K  K          L  E  E  K  M  K  K  V  M  K
                                                                   ↑

OLIGONUCLEOTIDE INSERTS

GCTGGAAGAAAAAGATGAAGGCTATGGAGGAGAAGATGAAGAAAAGATGAAGAAGCT
                CCTTCTTTTTCTACTTCCGATACCTCCTCTTCTACTTCTTTTCTACTTCTTCGA
             L   E  E  K  M  K  A  M  E  E  E  K  M  K  K  W  L  E  E  K  M  K  K

↓ OLIGOS LIGATED INTO EARI CUT BASE GENE

NCOI
      ┌─────┐
      │CATG│GAGGAGAAGATGAAAAA GCTGGAAGAAAAAGATGAAGGCTATGGAGGAGAAGATGAAGAAAAGATGAAGAAGCT
       GTAC CTCCTCTTCTACTTTTTCTA CCTTCTTTTTCTACTTCCGATACCTCCTCTTCTACTTCTTTTCTACTTCTTCGA
        M   E  E  K  M  K  K     L  E  E  K  M  K  A  M  E  E  E  K  M  K  K  W  L  E  E  K  M  K  K  L

EARI           BSPHI    ASP718   ECORI
     ┌──────┐        ┌─────┐  ┌───────┐
      G│AAGAG│AAGATGAAGG│TCATGA│GTGA│AGGTACC│G           CLONE pSK34
       GCTTCTCTTCTACTTCC AGTACT CACT TCCATGG CTTAA
        E  E  K  M  K  V  M  K
```

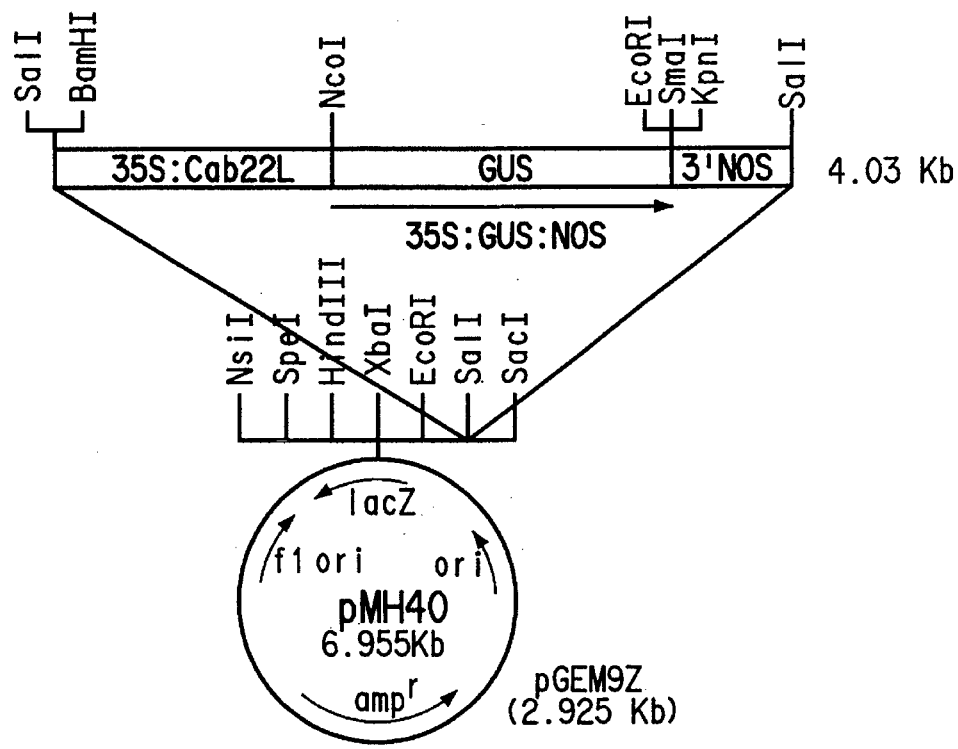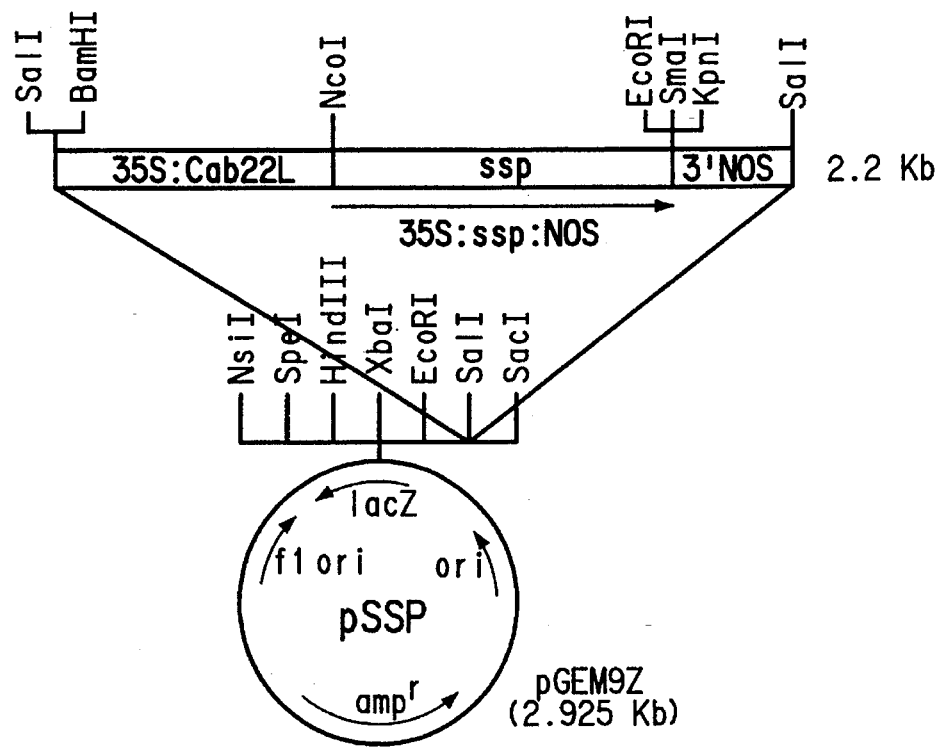
FIG. 10

SYNTHETIC STORAGE PROTEINS WITH DEFINED STRUCTURE CONTAINING PROGRAMMABLE LEVELS OF ESSENTIAL AMINO ACIDS FOR IMPROVEMENT OF THE NUTRITIONAL VALUE OF PLANTS

This application, filed as PCT/US92/06412, on Aug. 7, 1992 is a continuation-in-part of application Ser. No. 07/743,006, filed on Aug. 9, 1991, now abandoned.

BACKGROUND OF THE INVENTION

The worldwide animal feed market, which includes livestock, poultry, aquaculture and pets is 475 million metric tons. In the United States 180 million metric tons are consumed, with corn (*Zea mays* L.) accounting for about 67% and soybean (*Glycine max* L.) meal for about 10% of the total. Corn and soybean products are also a major element of international trade.

Human food and animal feed derived from many grains are deficient in some of the ten essential amino acids (cysteine, isoleucine, lysine, methionine, phenylalanine, threonine, tyrosine, and valine) which are required in animal diets. In corn, lysine is the most limiting amino acid followed by tryptophan and the sulfur amino acids, methionine and cysteine, for the dietary requirements of many animals. The usefulness of soybean meal, which is rich in lysine and tryptophan, to supplement corn in animal feed is limited by the low sulfur amino acid content of the legume. When soybean meal is used to supplement the lysine levels of corn, the low levels of methionine in soybeans cause the blended feed to have an even lower level of methionine than the original corn. As a result, feed blends of corn and soybean typically still include methionine as an additive. A typical composition of chicken starter rations is shown in Table 1 [Powell et al., (1976) Poult. Science. 55:502–509].

TABLE 1

Composition of Practical Chicken Starter Rations

| | |
|---|---|
| Yellow Corn | 57.25% |
| Soybean Meal (49% protein) | 29.00 |
| Fish solubles | 0.65 |
| Wheat middlings | 2.50 |
| Delactosed whey | 1.50 |
| Costal bermudagrass, dehydrated | 5.00 |
| Minerals | 0.25 |
| Vitamins | 0.25 |
| Animal fat | 0.25 |
| DL-Methionine | 0.10 |
| Choline chloride | 0.10 |

Thus, a mechanism to increase the levels of particular amino acids within the plant seed for a given crop and a specific end use would eliminate the need to supplement mixed or single grain feeds with purified amino acids. Furthermore, the methionine requirements of poultry and swine (the two largest consumers of soybean meal accounting for 78% of the soy protein used in feeds [Wilcox, (1987) Agronomy 16:823]) decrease with age of the animal [Ensminger et al., (1978) Feeds and Nutrition, The Ensminger Publishing Co. Clovis, Calif.]. The ability to improve the essential amino acid content of soybean or corn in a controllable manner is therefore, extremely desirable. A solution to this problem is the design of a class of synthetic proteins which can be tailored to complement the deficiencies of any crop for use in feeding any animal of any age.

The amino acid content of seeds is determined primarily by the storage proteins which are synthesized during seed development and which serve as a major nutrient reserve following germination. The quantity of protein in seeds varies from about 10% of the dry weight in cereals to 20–40% of the dry weight of legumes. In many seeds the storage proteins account for 50% or more of the total protein. Because of their abundance, plant seed storage proteins were among the first plant proteins to be isolated. Only recently, however, have the amino acid sequences of some of these proteins been determined with the use of molecular genetic techniques. These techniques have also provided information about the genetic signals that control the seed-specific expression and the intracellular targetting of these proteins.

Although no plant seed storage proteins enriched in lysine relative to average lysine content of plant proteins have been identified, a number of sulfur-rich plant seed storage proteins have been identified and their corresponding genes isolated. A gene in corn for a 15 kD zein protein containing 11% methionine and 5% cysteine [Pedersen et al., (1986) J. Biol. Chem. 261:6279–6284] and a gene for a 10 kD zein protein containing 23% methionine and 3% cysteine have been isolated [Kirihara et al., (1988) Mol. Gen. Genet. 21:477–484; Kirihara et al., (1988) Gene 71:359–370]. Two genes from pea for seed albumins containing 8% and 16% cysteine have been isolated [Higgins et al., (1986) J. Biol. Chem. 261:11124–11130]. A gene from Brazil nut for a 2S albumin containing 18% methionine and 8% cysteine has been isolated [Altenbach et al., (1987) Plant Mol. Biol. 8:239–250]. Finally, a gene coding for a 10 kD seed prolamin containing 19% methionine and 10% cysteine has been isolated from rice [Masumura et al., (1989) Plant Mol. Biol. 12:123–130].

Plant breeders have long been interested in using naturally-occuring variations to improve protein quality and quantity in crop plants [Deutscher, (1978) Adv. Exp. Medicine and Biology 105:281–300]. Maize lines containing higher levels of lysine (70% increase) and tryptophan (100% increase) have been identified [Mertz, (1964) Science 145:279 and Nelson, (1965) Science 150:1469–70]. However, these lines which incorporate a mutant gene, opaque-2, exhibit poor agronomic qualities (increased susceptibility to disease and pests, 8–14% reduction in yield, low kernel weight, slower drying, lower dry milling yield of flaking grits, and increased storage problems) and are not commercially useful [Deutscher, (1978) Adv. Exp. Medicine and Biology 105:281–300]. Further breeding to improve the agronomics of opaque-2 lines is complicated because several modifier genes are involved which have complex inheritence patterns [Vasal, S. K. (1974) Symposium Proceedings. Worldwide Maize Improvement in the 70's and the Role for CIMMYT. Centro Internacional de MeJoramiento de Maiz y Trigo. El Batan, Mexico]. In spite of the difficulties, a few researchers have continued to work with opaque-2 mutants. Quality Protein Maize (QPM), bred at CIMMYT using the opaque-2 and sugary-2 genes and associated modifiers, has a hard endosperm and enriched levels of lysine and tryptophan in the kernals [Vasal et al., Proceedings of the 3rd Seed Protein Symposium, Gatersleben, Aug. 31–Sep. 2, (1983)].

However, the gene pools represented in the QPM lines are tropical and subtropical and they are only available as open pollinated types (hybrids are mainly used in the United States) [National Research Council Report (1988) Quality Protein Maize. National Academy Press, Washington, D.C.]. QPM is genetically complex and the existing lines are not easily adapted to the dent germplasm used in the United States. These factors prevent the adoption of QPM by U.S. corn breeders.

Efforts to improve the sulfur amino acid content of crops through traditional plant breeding have met with limited success on the laboratory scale and no success on the commercial scale. A mutant corn line with an elevated whole-kernel methionine concentration was isolated from corn cells grown in culture by selecting for growth in the presence of inhibitory concentrations of lysine plus threonine [Phillips et al., (1985) Cereal Chem. 62:213–218]. However, agronomically-acceptable cultivars have not yet been derived from this line.

Traditional breeding efforts designed to increase the level of methionine in soybean protein have been limited compared to efforts to increase overall protein quantity in soybeans [Burton, 1984 World Soybean Research Conference III Proceedings, p. 361–368 (Aug. 12–Aug. 17, 1984)]. Soybean cell lines with increased intracellular concentrations of methionine were isolated by selection for growth in the presence of ethionine, a nonmetabolizable methionine analog, Madison et al., (1988) Plant Cell Reports 7: 472–476, but plants were not regenerated from these lines.

Recombinant DNA technology offers the potential for altering the amino acid composition of crop plants. Particularly useful technologies are: (a) methods for the molecular cloning and in vitro manipulation of genes [see Sambrook et al., (1989) Molecular Cloning: a Laboratory Manual, 2nd Ed., Cold Spring Harbor Laboratory Press], (b) introduction of genes via transformation into agriculturally-important crop plants such as soybean [Chee et al., (1989) Plant Physiol. 91: 1212–1218; Christou et al., (1989) Proc. Nat. Acad. Sci U.S.A. 86:7500–7504; Hinchee et al., (1989) Biotechnology 6:915–922; EPO publication 0301 749 A2], rapeseed [De Block et al., (1989) Plant Physiol. 91:694–701], and corn [Gordon-Kamm et al., (1990) Plant Cell 2:603–618; Fromm et al., (1990) Biotechnology 8:833–839], and (c) seed-specific expression of introduced genes in transgenic plants [see Goldberg et al., (1989) Cell 56:149–160); Thompson et al., (1989) BioEssays 10:108–113]. In order to use these technologies to develop crop plants with increased lysine and sulfur amino acid content, it is essential to obtain or develop commercially-important gene products enriched in the appropriate amino acids.

Expression of seed storage protein genes in transgenic plants have been reported in the model plant systems, tobacco or petunia, because it has only recently become possible to transform agriculturally-important crop plants such as corn and soybean. In general, dicot seed storage protein genes were expressed in a seed-specific manner in transformed dicot plants. Furthermore, both temporal and spatial control of gene expression was maintained. The transgenic protein products have, in some cases, been shown to be correctly processed and assembled into appropriate multimeric forms. [Beachy et al., (1985) EMBO J. 4:3047–3053; Sengupta-Gopalan et al., (1985) Proc. Natl. Acad. Sci. USA 82:3320–3324; Barker et al., (1988) Proc. Natl. Acad. Sci. USA 85:458–462; Ellis et al., (1988) Plant Mol. Biol. 10:203–214; Naito et al., (1988) Plant Mol. Biol. 11:109–123; Hoffman et al., (1988) Plant Mol. Biol. 11:717–729; Altenbach et al., (1989) Plant Mol. Biol. 13: 513–522].

Storage proteins are usually targetted to subcellular locales by the processing of N-terminal signal peptides or carboxy-terminal sequences such as SEKDEL [Bednareket al., (1990) The Plant Cell, 2: 1145–1155. Munro et al., (1987) Cell 48:899–907; Pelham, (1988) EMBO J. 7:913–918; Pelham et al., (1988) EMBO J. 1757–1762; Inohara et al., (1989) Proc. Natl. Acad. Sci. U.S.A. 86:3564–3568; Hesse et al., (1989) EMBO J. 8:2453–2461]. It may prove necessary to create chimeric genes incorporating these signals for proper localization and stability of synthetic storage proteins.

Expression of seed storage protein genes in the leaves of plants is accomplished by replacing the regulatory signals that function in the seed with signals that function in the leaf [Lawton et al., (1987) Plant Mol. Biol. 9:315–324; Schernthaner et al., (1988) EMBO J. 7:1249–1255]. Monocot seed storage protein genes were expressed at very low levels [Schernthaner et al., (1988) EMBO J. 7:1249–1255] and, in one case, expressed in a non-seed-specific manner in transformed dicot plants [Ueng et. al., (1988) Plant Physiol. 86:1281–1285]. Replacement of the monocot regulatory regions (promoter and transcription terminator) with dicot seed-specific regulatory regions resulted in low level seed-specific expression of the protein in one case [Williamson et. al., (1988) Plant Physiol. 88:1002–1007]. In another case, high-level seed-specific expression of the monocot protein was found and the signal sequence of the monocot precursor was also correctly processed [Hoffman et al., (1987) EMBO J. 6:3213–3221].

In order to increase the lysine and sulfur amino acid contents of seeds, it is essential to obtain a gene or genes coding for a protein rich in lysine and the sulfur-containing amino acids methionine and cysteine. Methionine is preferable to cysteine because methionine can be converted to cysteine by most animals, while cysteine cannot be converted to methionine. It is desirable that the introduced protein be compatible with the target crop plant. It is desirable to select the gene to maximize lysine and sulfur amino acid content thereby minimizing the level of expression required in the plant to satisfy end-user needs. For this reason, those skilled in the art have not restricted themselves to natural genes and their polypeptide products.

Jaynes et al. worked with synthetic polypeptides which have elevated levels of lysine, methionine, tryptophan, threonine, and isoleucine as compared to known proteins [WO 89/04371]. These synthetic genes were formed by random ligation of mixtures of small oligodeoxy-nucleotides containing a high proportion (25–60%) of codons for essential amino acids. The proteins so formed are heterogeneous and do not fold to defined structures. Limited expression (0.02–0.35% of total plant protein) has been demonstrated in potato [Yang et al., (1989) Plant Science, 64: 99–111].

Others have modified natural proteins by addition or replacement of amino acids to increase the lysine or methionine content [DeClercq et al., EP 0 318 341 A1]. DeClercq et al. have Shown that it is possible to express modified storage protein genes in tobacco, Arabidopsis, and Brassica plants. However, their work gives little guidance regarding the design of the sequences rich in appropriate amino acids which are to be inserted into a target gene product. They observe only that the stability of the molecule should not be influenced and that long stretches of methionines should be interrupted by amino acids which break helical structures. Furthermore, the specific polypeptide sequences inserted into the target gene were not designed to adopt uniquely defined stable structures.

The importance of gene product stability in the seed dictates the need for a polypeptide of defined structure, while the need to complement existing amino acid composition and to satisfy end-user requirements emphasizes the importance of a flexible system which can accomodate variations in composition without sacrificing final gene product stability.

SUMMARY OF THE INVENTION

Applicants have provided an invention which overcomes the limitations of naturally-occurring plant proteins and provides flexibility to satisfy the nutritional requirements of humans and animals by means of the design and expression in plants and microorganisms of synthetic seed storage proteins (SSPs).

The introduction into transgenic crop plants of a chimeric gene comprising seed storage protein regulatory sequences and an appropriate protein coding sequence rich in essential amino acids represents an approach to improve the nutritional quality of seeds from crop plants. These sequences can be designed to code for amino acid sequences which result in a particular tertiary structure that improves stablity. The increase in essential amino acid content of the seed will be determined by: (a) the level of expression of the chimeric gene in the transformed crop, which depends, in part, upon the seed-specific expression, the translatability and stability of the mRNA and targetting signals used; (b) the percentage of the designated amino acid residues in the seed storage protein coding region; (c) the stability of the introduced protein in the seed of the transformed crop plant, which depends, in part, upon its proper processing, intracellular targetting, assembly into higher-order structures, and ability to withstand desiccation; and (d) the compatibility of the introduced protein with the native seed proteins of the transformed crop.

The present invention provides a means to overexpress proteins high in lysine and methionine content by providing gene sequences and promoters capable of transforming target plants. Specifically one aspect of the present invention is a synthetic polypeptide comprising n heptad units (d e f g a b c), each heptad being either the same or different, wherein:

n is at least 4;

a and d are independently selected from the group consisting of Met, Leu, Val, Ile and Thr;

e and g are independently selected from the group consisting of the acid/base pairs Glu/Lys, Lys/Glu, Arg/Glu, Arg/Asp, Lys/Asp, Glu/Arg, Asp/Arg and Asp/Lys; and b, c and f are independently any amino acids except Gly or Pro and at least two amino acids of b, c and f in each heptad are selected from the group consisting of Glu, Lys, Asp, Arg, His, Thr, Ser, Asn, Ala, Gln, Cys and Ala.

Additionally, this aspect of the invention may have a+d independently selected from the group consisting of Met and Leu, or where e and g are independently either Lys/Glu or Glu/Lys, or where b, c, and f are selected such that if f is a charged amino acid then b or c carries the opposite charge.

In addition, another aspect of the invention further obeys conditions wherein:

n is at least 4;

a and d are independently selected from the group consisting of Met and Leu;

e and g are independently either Lys/Glu or Glu/Lys; and b, c and f are independently any amino acids except Gly or Pro, at least two amino acids of b, c, and f in each heptad are selected from the group Glu, Lys. Asp, Arg, His, Thr, Ser, Asn, Ala, Glu, and Cys, and b, c, and f are selected such that if f is a charged amino acid then b or c carries the opposite charge.

Specific heptad units which conform to the invention are:

| | | | |
|---|---|---|---|
| LEEKLKA | (SEQ ID NO:60) | LKEELKA | (SEQ ID NO:69) |
| MEEKLKA | (SEQ ID NO:61) | MKEELKA | (SEQ ID NO:70) |
| MEEKMKA | (SEQ ID NO:62) | MKEEMKA | (SEQ ID NO:71) |
| LEEKLKK | (SEQ ID NO:63) | LKEELKK | (SEQ ID NO:72) |
| MEEKLKK | (SEQ ID NO:64) | MKEELKK | (SEQ ID NO:73) |
| MEEKMKK | (SEQ ID NO:65) | MKEEMKK | (SEQ ID NO:74) |
| LEEKLKW | (SEQ ID NO:66) | LKEELKW | (SEQ ID NO:75) |
| MEEKLKW | (SEQ ID NO:67) | MKEELKW | (SEQ ID NO:76) |
| MEEKMKW | (SEQ ID NO:68) | MKEEMKW | (SEQ ID NO:77) |
| MEDKMKW | (SEQ ID NO:78) | LEEKMKV | (SEQ ID NO:81) |
| LKEEMAK | (SEQ ID NO:79) | MKDEMWK | (SEQ ID NO:82) |
| LKEEMKK | (SEQ ID NO:80) | | |

A further aspect of the invention are synthetic polypeptides selected from the group consisting of SEQ ID NOS: 1, 2, 3, 4, 5, 6, 7 and 83.

An aspect of the invention are the nucleic acid fragments encoding the claimed polypeptides.

Another aspect of the invention is a chimeric gene, comprising a regulatory sequence of the invention and a DNA sequence coding for the desired protein operably linked to the regulatory sequence such that the transformed host cell expresses the desired protein. When the preferred host cell is eukaryotic and selected from corn, soybean, BRASSICA spp. (*B. napus, B. campistris, B. oleracea*), tobacco, rice, potato, forage grasses, and wheat, preferred regulatory sequences are those active in plant seeds and include those encoding for soybean kunitz trypsin inhibitor, glycinin, β-conglycinin, lectin, bean lectin, phaseolin, corn 10 kD zein, 27 kD zein, and 19 kD zein globulin 1 and globulin 2. When the preferred host cell is *E. coli* the preferred regulatory sequence is a bacteriophage T7 promoter system and translational initiation sequence.

A further aspect of the invention is a host cell transformed with the chimeric gene of the invention such that the transformed host cell expresses the desired protein. Yet another aspect of the invention is a plant transformed with the chimeric gene of the invention such that the transformed plant expresses the desired protein. The seeds of such transformed plants are also regarded as an embodiment of the invention.

A final aspect of the invention is a method of varying the content of essential amino acids in plants in response to end-user nutritional requirements, comprising the steps of a. assessing deficiencies of a feed crop plant relative to the end-user nutritional requirements;

b. synthesizing a nucleic acid fragment that encodes a polypeptide, for instance, of the structure described herein, to correct the amino acid deficiencies identified in step a;

c. combining the nucleic acid synthesized in step b with regulatory sequences for expression and localization in plant tissues;

d. transforming a plant cell with the product of step c;

e. regenerating plants from said transformed plant cell of step d to obtain mature plants;

f. screening the seeds of the plants of step e for the desired variation in amino acid level.

The invention can be more fully understood from the following detailed description, the accompanying drawings and the Sequence Descriptions which form a part of this application. The Sequence Descriptions contain the one letter code for nucleotide sequence characters and the three letter codes for amino acids in conformity with the IuPAC-1UB standards described in Nucleic Acids Research 13:3021–3030 (1985) and in The Biochemical Journal 219:345–373 (1984) which are incorporated by reference herein. The amino acid residues are labelled according to the conventions of the coiled-coil literature. The citation herein of any patents, pending U.S. applications, and any other disclosure that was available to the public as of the filing date of the instant application are incorporated herein by reference in their entirety.

BRIEF DESCRIPTION OF THE DRAWINGS AND SEQUENCE DESCRIPTIONS

FIG. 2A shows the end view of an alpha helical coiled-coil structure.

FIG. 2B shows the side view of an alpha helical coiled-coil structure.

FIG. 3 shows the chemical structure of leucine and methionine emphasizing their similar shapes.

FIG. 8 shows the insertion of the 63 bp "segment" oligonucleotides used to create non-repetitive gene sequences for use in the duplication scheme in FIG. 9.

FIG. 10 shows the construction of a chimeric gene for expression of SSPs in plants.

Figure 1:
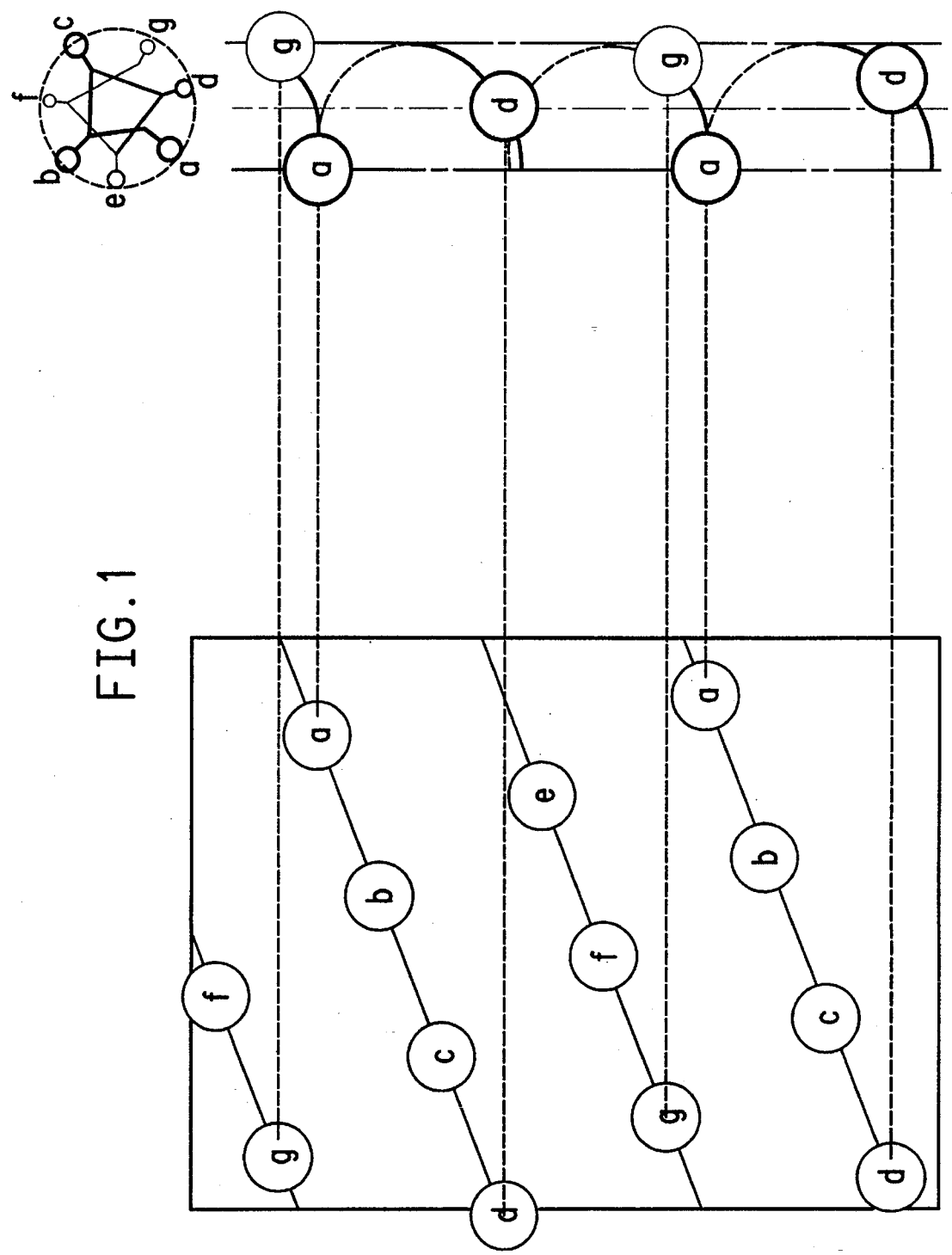
FIG. 1 shows an alpha helix from the side and top views.

The SEQ ID NOS:1–7 and 83 are SSP polypeptide sequences suitable for expression in vivo.

The SEQ ID NOS:8 and 31 are CSP polypeptide sequences unsuitable for expression in vivo.

The SEQ ID NOS:60–82 are specific claimed embodiments of SSP polypeptide sequences suitable for expression in vivo.

The SEQ ID NOS:9–30, and 32–59, 84–105, 110–112 represent nucleic acid fragments and the proteins they encode referenced in the text and used in the development of the claimed invention.

DEFINITIONS

In the context of this disclosure, a number of terms shall be utilized. As used herein, the term "nucleic acid" refers to a large molecule which can be single-stranded or double-stranded, composed of monomers (nucleotides) containing a sugar, phosphate, and either a purine or pyrimidine. A "nucleic acid fragment" is a fraction of a given nucleic acid molecule. In higher plants, deoxyribonucleic acid (DNA) is the genetic material while ribonucleic acid (RNA) is involved in the transfer of the information in DNA into proteins. A "genome" is the entire body of genetic material contained in each cell of an organism. The term "nucleotide sequence" refers to a polymer of DNA or RNA which can be single- or double-stranded, optionally containing synthetic, non-natural or altered nucleotide bases capable of incorporation into DNA or RNA polymers.

As used herein, the term "homologous to" refers to the complementarity between the nucleotide sequence of two nucleic acid molecules or between the amino acid sequences of two protein molecules. Estimates of such homology are provided by either DNA-DNA or DNA-RNA hybridization under conditions of stringency as is well understood by those skilled in the art [as described in Hames and Higgins, Eds. (1985) Nucleic Acid Hybridisation, IRL Press, Oxford, U.K.]; or by the comparison of sequence similarity between two nucleic acids or proteins.

As used herein, "substantially homologous" refers to nucleic acid molecules which require less stringent conditions of hybridization than those for homologous sequences, and also refers to coding DNA sequences which may involve base changes that do not cause a change in the encoded amino acid, or which involve base changes which may alter one or more amino acids, but not affect the functional properties of the protein encoded by the DNA sequence. Thus, the nucleic acid fragments described herein include molecules which comprise possible variations of the nucleotide bases derived from deletion, rearrangement, random or controlled mutagenesis of the nucleic acid fragment, and even occasional nucleotide sequencing errors so long as the DNA sequences are substantially homologous.

"Gene" refers to a nucleic acid fragment that expresses a specific protein, including regulatory sequences preceding (5' non-coding) and following (3' non-coding) the coding region. "Native" gene refers to the gene as found in nature with its own regulatory sequences. "Chimeric" gene refers to a gene comprising heterogeneous regulatory and coding sequences. A "foreign" gene refers to a gene not normally found in the host organism but that is introduced by gene transfer.

"Coding sequence" refers to a DNA sequence that codes for a specific protein and excludes the non-coding sequences. It may constitute an "uninterrupted coding sequence", i.e., lacking an intron, such as in a cDNA or it may include one or more introns bounded by appropriate splice junctions. An "intron" is a sequence of RNA which is transcribed in the primary transcript but which is removed through cleavage and re-ligation of the RNA within the cell to create the mature mRNA that can be translated into a protein.

"Initiation codon" and "termination codon" refer to a unit of three adjacent nucleotides in a coding sequence that specifies initiation and chain termination, respectively, of protein synthesis (mRNA translation). "Open reading frame" refers to the amino acid sequence encoded between translation initiation and termination codons of a coding sequence.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA" (mRNA) refers to the RNA that is without introns and that can be translated into protein by the cell.

As used herein, "suitable regulatory sequences" refer to nucleotide sequences located upstream (5'), within, and/or downstream (3') to a coding sequence, which control the transcription and/or expression of the coding sequences, potentially in conjunction with the protein biosynthetic apparatus of the cell. "Suitable regulatory sequences" include promoters, enhancers, translation leader sequence, 3' non-coding sequence.

"Promoter" refers to a DNA sequence in a gene, usually upstream (5') to its coding sequence, which controls the expression of the coding sequence by providing the recognition for RNA polymerase and other factors required for proper transcription. A promoter may also contain DNA sequences that are involved in the binding of protein factors which control the effectiveness of transcription initiation in response to physiological or developmental conditions. It may also contain enhancer elements.

An "enhancer" is a DNA sequence which can stimulate promoter activity. It may be an innate element of the promoter or a heterologous element inserted to enhance the level and/or tissue-specificity of a promoter. "Constitutive promoters" refers to those that direct gene expression in all tissues and at all times. "Organ-specific" or "development-specific" promoters as referred to herein are those that direct gene expression almost exclusively in specific organs, such as leaves or seeds, or at specific development stages in an organ, such as in early or late embryogenesis, respectively.

The term "expression", as used herein, is intended to mean the production of the protein product encoded by a gene. A "gene product" refers to the protein produced by the translation of an mRNA corresponding to a gene sequence. "Overexpression" refers to the production of a gene product in transgenic organisms that exceeds levels of production of that protein in normal or non-transformed organisms.

The "3' non-coding sequences" refers to the DNA sequence portion of a gene that contains a transcription termination signal, a polyadenylation signal and any other regulatory signal capable of affecting mRNA processing or gene expression. The polyadenylation signal is usually characterized by affecting the addition of polyadenylic acid tracts to the 3' end of the mRNA precursor.

The "translation leader sequence" refers to that DNA sequence portion of a gene between the promoter and coding sequence that is transcribed into RNA and is present in the fully processed mRNA upstream (5') of the translation start codon. The translation leader sequence may affect processing of the primary transcript to mRNA, mRNA seability or translation efficiency.

"Signal peptide" refers to the amino terminal extension of a polypeptide, which is translated in conjunction with the polypeptide forming a precursor peptide and which is required for its entrance into the secretory pathway. The term "signal sequence" refers to a nucleotide sequence that encodes the signal peptide.

"Intracellular localization sequence" refers to a nucleotide sequence that encodes an intracellular targetting signal. An "intracellular targetting signal" is an amino acid sequence which is translated in conjunction with a protein and directs it to a particular sub-cellular compartment. "Endoplasmic reticulum (ER) stop transit signal" refers to a carboxy-terminal extension of a polypeptide, which is translated in conjunction with the polypeptide and causes a protein that enters the secretory pathway to be retained in the ER. "ER stop transit sequence" refers to a nucleotide sequence that encodes the ER targetting signal. Other intracellular targetting sequences encode targetting signals active in seeds and/or leaves and vacuolar targetting signals.

"Transformation" herein refers to the transfer of a foreign gene into the genome of a host organism and its genetically stable inheritance. Examples of methods of plant transformation include Agrobacterium-mediated transformation and particle-accelerated or "gene gun" transformation technology. "Forage grasses" herein refer to grasses utilized as fodder for animals. "Host cell" refers to a plant, animal or microorganism cell transformed with the chimeric gene of this invention.

"Amino acids" herein refer to the naturally occuring L amino acids (Alanine, Arginine, Aspartic acid, Asparagine, Cystine, Glutamic acid, Glutamine, Glycine, Histidine, Isoleucine, Leucine, Lysine, Methionine, Proline, Phenylalanine, Serine, Threonine, Tryptophan, Tyrosine, and Valine). "Essential amino acids" are those amino acids which cannot be synthesized by animals. A "polypeptide" or "protein" as used herein refers to a molecule composed of monomers (amino acids) linearly linked by amide bonds (also known as peptide bonds).

"Synthetic protein" herein refers to a protein consisting of amino acid sequences that are not known to occur in nature. The amino acid sequence may be derived from a consensus of naturally occuring proteins or may be entirely novel.

"Primary sequence" refers to the connectivity order of amino acids in a polypeptide chain without regard to the conformation of the molecule. Primary sequences are written from the amino terminus to the carboxy terminus of the polypeptide chain by convention.

"Secondary structure" herein refers to physico-chemically favored regular backbone arrangements of a polypeptide chain without regard to variations in side chain identities or conformations. "Alpha helices" as used herein refer to right-handed helices with approximately 3.6 residues residues per turn of the helix. An "amphipathic helix" refers herein to a polypeptide in a helical conformation where one side of the helix is predominantly hydrophobic and the other side is predominantly hydrophilic.

"Coiled-coil" herein refers to an aggregate of two parallel right-handed alpha helices which are wound around each other to form a left-handed superhelix.

"Salt bridges" as discussed here refer to acid-base pairs of charged amino acid side chains so arranged in space that an attractive electrostatic interaction is maintained between two parts of a polypeptide chain or between one chain and another.

"Host cell" means the cell, either plant or animal, that is transformed with the introduced genetic material.

In the context of this invention a protein "enriched" in an essential amino acid is one which contains a higher percentage of that amino acid than is found for average mixtures of natural proteins.

DETAILED DESCRIPTION

Design of SSP Polypeptide Sequences

One aspect of this invention is the design of polypeptides which can be expressed in vivo to serve as synthetic seed storage proteins. Polypeptides are linear polymers of amino acids where the α-carboxyl group of one amino acid is covalently bound to the α-amino group of the next amino acid in the chain. Non-covalent interactions among the residues in the chain and with the surrounding solvent determine the final conformation of the molecule. Those skilled in the art must consider electrostatic forces, hydrogen bonds, Van der Waals forces, hydrophobic interactions, and conformational preferences of individual amino acid residues in the design of a stable folded polypeptide chain [see for example: Creighton, (1984) Proteins, Structures and Molecular Properties, W. H. Freeman and Company, New York, pp. 133–197, or Schulz et al., (1979) Principles of Protein Structure, Springer Verlag, New York, pp. 27–45]. The number of interactions and their complexity suggest that the design process may be aided by the use of natural protein models where possible.

The synthetic storage proteins (SSPs) embodied in this invention are chosen to be polypeptides with the potential to be enriched in lysine, methionine, or tryptophan relative to average levels (see Table 2) [Schulz et al., (1979) Principles of Protein Structure. Springer Verlag, New York, pp.2; Bright et al., (1983) CRC Critical Rev. Plant Sci. 1:49–93; and Smith et al., Eds., (1978) Soybeans: Chemistry and Technology. Vol 1: The AVI Publishing Co. Westport, Conn.].

TABLE 2

| Average Amino Acid Content of Protein Derived From Bacteria or Plants | | | |
|---|---|---|---|
| | E. coli | Corn | Soybean | SSPs |
| Lysine | 7.0 | 3.52 | 6.4 | up to 43% |
| Methionine | 3.8 | 2.04 | 1.6 | up to 43% |
| Tryptophan | 1.0 | 0.94 | 1.2 | up to 14% |

Lysine is a charged amino acid at physiological pH and is therefore found most often on the surface of protein molecules [Chotia, (1976) Journal of Molecular Biology 105:1–14]. To maximize lysine content Applicants chose a molecular shape with a high surface-to-volume ratio for the synthetic storage proteins embodied in this invention. The alternatives were either to stretch the common globular shape of most proteins to form a rod-like extended structure or to flatten the globular shape to a disk-like structure. Applicants chose the former configuration as there are several natural models for long rod-like proteins in the class of fibrous proteins [Creighton, (1984) Proteins, Structures and Molecular Properties, W. H. Freeman and Company, New York, p. 191].

Coiled-coils constitute a well-studied subset of the class of fibrous proteins [see Cohen et al., (1986) Trends Biochem. Sci. 11:245–248]. Natural examples are found in α-keratins, paramyosin, light meromyosin and tropomyosin. These protein molecules consist of two parallel alpha helices twisted about each other in a left-handed supercoil. The repeat distance of this supercoil is 140 Å (compared to a repeat distance of 5.4 Å for one turn of the individual helices). The supercoil causes a slight skew (10°) between the axes of the two individual alpha helices.

In a coiled coil there are 3.5 residues per turn of the individual helices resulting in an exact 7 residue periodicity with respect to the superhelix axis (see FIG. 1). Every seventh amino acid in the polypeptide chain therefore occupies an equivalent position with respect to the helix axis. Applicants refer to the seven positions in this heptad unit of the invention as (d e f g a b c) as shown in FIGS. 1 and 2a. This conforms to the conventions used in the coiled-coil literature.

The a and d amino acids of the heptad follow a 4,3 repeat pattern in the primary sequence and fall on one side of an individual alpha helix (See FIG. 1). If the amino acids on one side of an alpha helix are all non-polar, that face of the helix is hydrophobic and will associate with other hydrophobic surfaces as, for example, the non-polar face of another similar helix. A coiled-coil structure results when two helices dimerize such that their hydrophobic faces are aligned with each other (See FIG. 2a).

The amino acids on the external faces of the component alpha helices (b, c, e, f, g) are usually polar in natural coiled-coils in accordance with the expected pattern of exposed and buried residue types in globular proteins [Schulz, et al., (1979) Principles of Protein Structure. Springer Verlag, New York, p. 12; Talbot, et al , (1982) Acc. Chem. Res. 15:224–230; Hodges et al., (1981) Journal of Biological Chemistry 256:1214–1224]. Charged amino acids are sometimes found forming salt bridges between positions e and g' or positions g and e' on the opposing chain (see FIG. 2a).

Thus, two amphipathic helices like the one shown in FIG. 1 are held together by a combination of hydrophobic interactions between the a, a', d, and d' residues and by salt bridges between e and g' and/or g and e' residues. The packing of the hydrophobic residues in the supercoil maintains the chains "in register". For short polypeptides comprising only a few turns of the component alpha helical chains, the 10° skew between the helix axes can be ignored and the two chains treated as parallel (as shown in FIG. 2a).

A number of synthetic coiled-coils have been reported in the literature (Lau et al., (1984) Journal of Biological Chemistry 259:13253–13261; Hodges et al., (1988) Peptide Research 1:19–30; DeGrado et al., (1989) Science 243:622–628; O'Neil et al., (1990) Science 250:646–651. Although these polypeptides vary in size, Lau et al. found that 29 amino acids were sufficient for dimerization to form the coiled-coil structure [Lau et al., (1984) Journal of Biological Chemistry 259:13253–13261]. Applicants constructed the polypeptides in this invention as 28-residue and larger chains for reasons of conformational stability.

A class of DNA binding proteins known as leucine zippers contain regions (usually 28 to 35 residues in length) which form a coiled-coil structure resulting in assembly of the protein into dimeric structures [O'Shea et al., (1989) Science 243:538]. Sequence analysis of these proteins shows that the d position is almost always occupied by a leucine residue. This position is also preferentially occupied by leucine in tropomyosin [Hodges et al., (1981) J. Biol. Chem. 256:1214–1224]. The eight e, g, e', and g' positions in these leucine zipper sequences are often charged residues. However natural protein sequences rarely form more than two interhelix salt bridges in one molecule.

The polypeptides of this invention are designed to dimerize with a coiled-coil motif in aqueous environments. Applicants have used a combination of hydrophobic interactions and electrostatic interactions to stabilize the coiled-coil conformation. Most nonpolar residues are restricted to the a and d positions which creates a hydrophobic stripe parallel to the axis of the helix. This is the dimerization face. Applicants avoided large, bulky amino acids along this face to minimize steric interference with dimerization and to facilitate formation of the stable coiled-coil structure.

Despite recent reports in the literature suggesting that methionine at positions a and d is destabilizing to coiled-coils in the leucine zipper subgroup [Landschulz et al., (1989) Science 243:1681–1688 and Hu et al., (1990) Science 250:1400–1403], Applicants chose to substitute methionine residues for leucine on the hydrophobic face of the SSP polypeptides. Methionine and leucine are similar in molecular shape (FIG. 3). Applicants demonstrated that any destabilization of the coiled-coil that may be caused by methionine in the hydrophobic core appears to be compensated in sequences where the formation of salt bridges (e-g' and g-e') occurs at all possible positions in the helix (i.e., twice per heptad).

To the extent that it is compatible with the goal of creating a polypeptide enriched in lysine and methionine, Applicants minimized the unbalanced charges in the polypeptide. This may help to prevent undesirable interactions between the synthetic storage proteins and other plant proteins when the polypeptides are expressed in vivo.

synthesizer using PAL™ resin as a solid support and standard 9-fluorenylmethyloxycarbonyl (Fmoc) chemistry for the coupling reactions. The crude peptides were cleaved from the resin with trifluoroacetic acid and purified to homogeneity by reverse-phase high pressure liquid chromatography (HPLC). Purified peptides were used as antigens in the generation of antibodies to be used as synthetic protein detection reagents and as standards for titering antibodies. The peptides were characterized using the physico-chemical techniques described below. The synthetic storage proteins embodied in this invention are all expected to form stable dimers in vivo (see Tables 3 and 4).

TABLE 3

| | Example of Coiled-coil Synthetic Storage Proteins | |
|---|---|---|
| SSP (4)$_4$ | LEEKLKALEEKLKALEEKLKALEEKLKA | SEQ ID NO:1 |
| SSP (5)$_4$ | MEEKMKAMEEKMKAMEEKMKAMEEKMKA | SEQ ID NO:2 |
| SSP (7)$_4$ | MEEKLKAMEEKLKAMEEKLKAMEEKLKA | SEQ ID NO:3 |
| SSP (8)$_4$ | MEEKLKKMEEKLKKMEEKLKKMEEKLKK | SEQ ID NO:4 |
| SSP (9)$_4$ | MEEKLKWMEEKLKWMEEKLKWMEEKLKW | SEQ ID NO:5 |
| SSP (10)$_4$ | MEEKMKKMEEKMKKMEEKMKKMEEKMKK | SEQ ID NO:6 |
| SSP (11)$_4$ | MEEKMKWMEEKMKWMEEKMKWMEEKMKW | SEQ ID NO:7 |
| SSP-3-5 (A/E) | MEEKLKAMEEKLKAMEEKLKAMEEKLKA MEEKLKAMEEKLKAMEEKMKEMEEKMKA | SEQ ID NO:112 |

Some of the peptides synthesized include tryptophan, a limiting amino acid in animal feeds derived from maize and soybean (see Table 2). The set also includes peptides which have a net positive charge. These peptides are only a few preferred examples of the class of SSP polypeptides embodied in this invention.

Two peptides were synthesized which form alpha helical structures in aqueous solution but which were unsuitable for expression in vivo (Table 4).

TABLE 4

| | Examples of Coiled-coil Synthetic Peptides Unsuitable for Expression in vivo | |
|---|---|---|
| CSP 1 | MEWEELKKKLEELKKKWEELKKKLEELKKK | SEQ ID NO:8 |
| CSP 2 | MEWEEMKKKMEEMKKKWEEMKKKMEEMKKK | SEQ ID NO:31 |

The polypeptides of this invention are designed to spontaneously fold into a defined, conformationally stable structure, the alpha helical coiled-coil, with minimal restrictions on the primary sequence. This allows synthetic storage proteins to be custom-tailored for specific end-user requirements. Any amino acid can be incorporated at a frequency of up to one in every seven residues using the b, c, and f positions in the heptad repeat unit. Applicants note that up to 43% of an essential amino acid from the group isoleucine, leucine, lysine, methionine, threonine, and valine can be incorporated and that up to 14% of the essential amino acids from the group phenylalanine, tryptophan, and tyrosine can be incorporated into the synthetic storage proteins of this invention (see Table 2).

Synthesis and Physical Characterization of SSP Polypeptide Sequences

The following peptides were synthesized from carboxy terminus to amino terminus on a Milligen/Biosearch peptide These peptides have many of the features of the synthetic storage proteins described above. However, they contain a bulky amino acid (tryptophan) on the hydrophobic surface and the salt bridges between positions positions e and g' or g and e' are absent. Although circular dichroism measurements indicate that these sequences become alpha helical in aqueous solution, a parallel coiled-coil is only one of several possible structures; they may form antiparallel two stranded coiled-coils, three stranded and four stranded parallel coils [Monera, poster, "Formation and Stability of Anti-Parallel Coiled-Coils", 9 Jun. 1992, at Protein Engineering Meeting—1992, Montreal, Quebec, Canada; Alber, Presentation, "X-Ray Structure of GCN4 Leucine Zippec, a 2-Standard Parallel Coiled-Coil" 9 Jun. 1992, at Protein Engineering Meeting—1992, Montreal, Quebec, Canada]. This suggests that for an SSP protein to be suitable for expression in vivo, the self association constant must be greater than the affinity of peptide monomers for cellular components.

The polypeptide chains discussed here are composed of L-amino acids and are optically active. Furthermore, the secondary structures formed by peptides in solution are also chiral. Circular Dichroism (CD) spectra of polypeptides in-solution can be used to estimate the percentage of alpha helical, beta sheet, and random coil conformations in a peptide sample [Adler, (1973) Methods Enzymol. 27:675–735]. Applicants used these techniques to characterize some example peptides which were chemically synthesized to confirm that they were conformationally stable coiled-coils in aqueous solution as designed (Example 2).

Analytical ultracentrifugation [Chervenka, C. H., (1973), A Manual of Methods for the analytical ultracentrifuge, pp. 39–64] can be used to determine the molecular weight of a protein in solution without regard to molecular shape and requiring only a knowledge of the partial specific volume of the protein. The partial specific volume can be approximated based on amino acid composition [E. J. Cohn and J. T. Edsall, "Proteins, Amino Acids and Peptides", p. 370, Von Nostrandt-Reinhold, Princeton, N.J., 1943]. Applicants used this technique to characterize the aggregation state of SSP-3-5(A/E) (SEQ ID NO:112), a 56 amino acid example of the synthetic storage protein family that embodies this invention. As described in Example 2 the solution was examined at three concentrations at each of two rotational speeds (28,000 rpm and 40,000 rpm) and two temperatures (4° C. and 20° C.). No monomers were detected. Results indicate that this protein is a nonequilibrium mixture of stable dimers and tetramers in solution.

In vivo environments are far more complex than the single component aqueous solution studied above. In the presence of membranes, there are two possible mechanisms for removing the hydrophobic face of the peptide from the aqueous environment: 1) interaction with the membrane and 2) dimerization to form a coiled-coil. Critical pressure values represent the surface pressure at which the energy required to insert a peptide into a membrane-like lipid monolayer is equal to the free energy gained in transferring the hydrophobic surface of the peptide from the aqueous solvent to the lipid. This technique is a measure of the relative affinity of various peptides for membranes as opposed to their dimerization affinities. The critical pressures of insertion by the synthetic peptides were used to compare the tendencies of the different peptides to interact with 1-palmitoyl, 2-oleyl phosphatidyl choline (POPG) monolayers and, by inference, naturally-occurring membranes composed of similar lipids.

Applicants observed no significant differences between the expression of the SSP sequences or combinations of the basic SSP sequences in *E. coli* (see below, Example 6). However, the peptides, CSP 1 and CSP 2 (Table 4), cannot be expressed well in *E. coli*. Applicants speculate that as the polypeptide is synthesized it interacts with the bacterial cell membrane resulting in cell lysis. Although CSP series peptides appeared to form a coiled-coil structure in aqueous solutions in vitro, (as measured by CD) they had a high affinity for membrane surfaces as measured by the determination of changes in the surface tension of POPG monolayers in the presence of CSP1 and/or CSP2.

Two of every four hydrophobic residues on the hydrophobic face of the CSP peptides is tryptophan. These residues are bulky and may cause unfavorable steric interactions between the two polypeptide chains on dimerization. Also, in the CSP series the e-g' and e'-g pairs are all positively charged lysine residues resulting in a repulsive electrostatic interaction between the polypeptide chains. The CSP series of polypeptides are not members of the set of synthetic storage proteins of this invention, although their properties were important in establishing the rules for defining acceptable structures for the synthetic storage proteins.

The SSP series, a preferred aspect of this invention, are distinguished from the CSP series by two important restrictions on their primary sequence. In the SSP series, only Met, Leu, Ile, Val or Thr are located in the hydrophobic core. Also, in contrast to the CSP series, the e, g, e', and g' positions in the SSP series are restricted such that an attractive electrostatic interaction always occurs at these positions between the two polypeptide chains in an SSP dimer. These differences make the SSP series polypeptides more stable as dimers than the CSP series peptides.

Figure 4A:
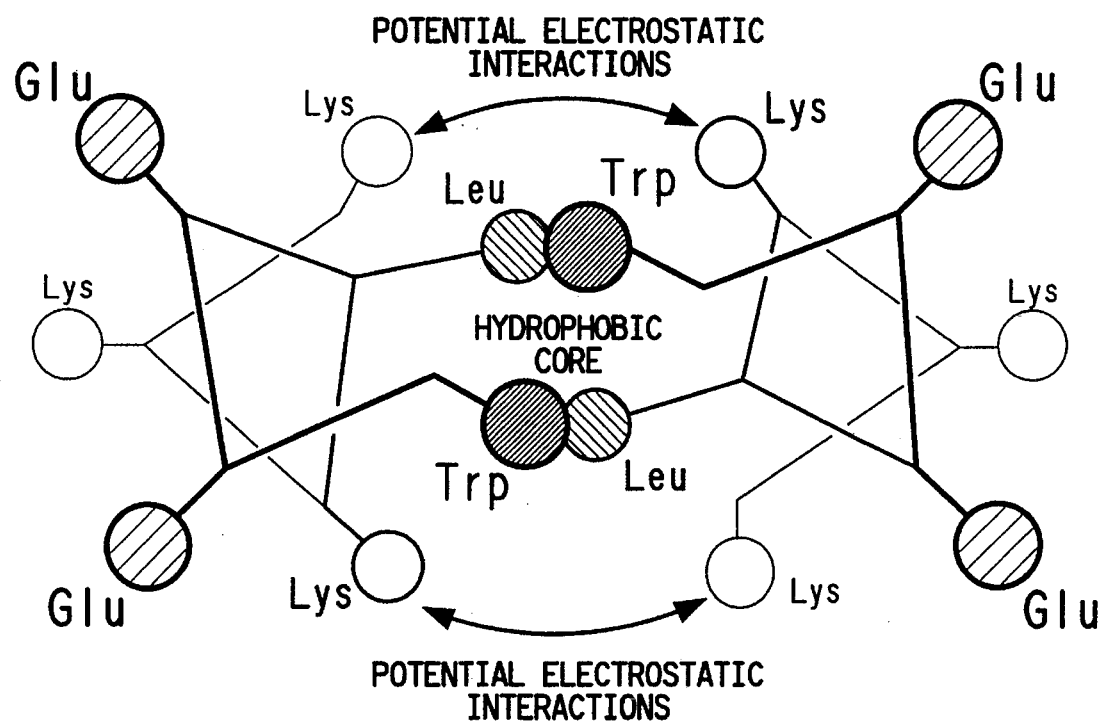
FIG. 4A shows the end view of the CSP series of chemically synthesized and characterized coiled-coil polypeptides.
Figure 4B:
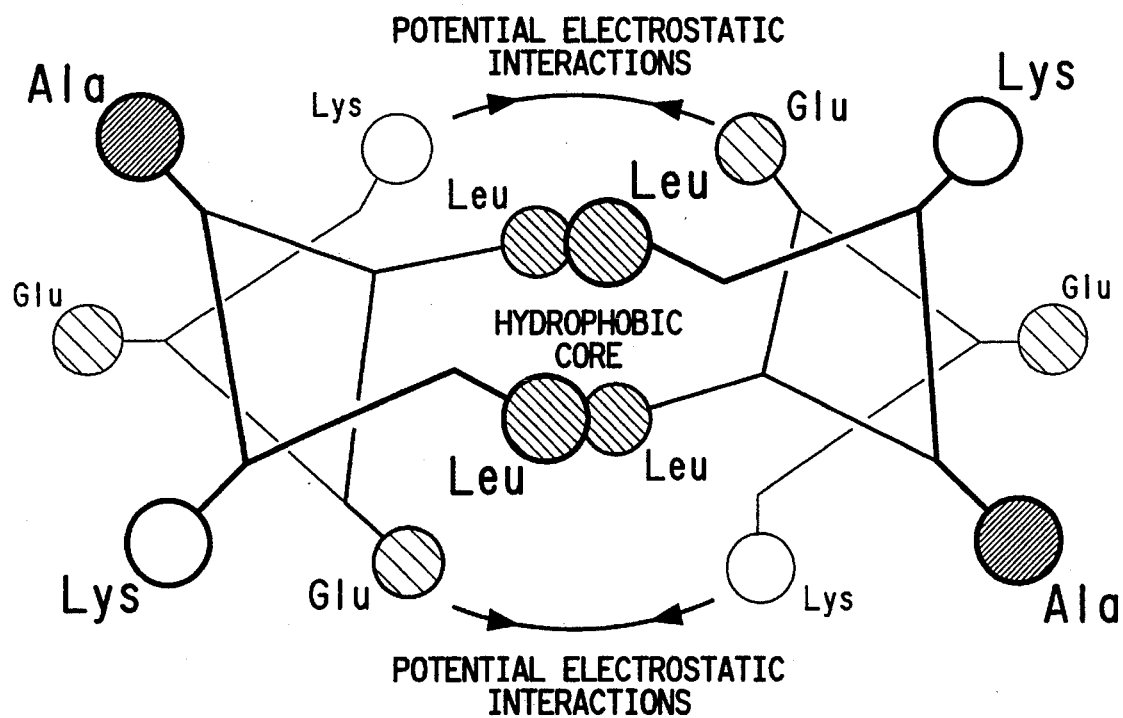
FIG. 4B shows the end view of the SSP series of chemically synthesized and characterized coiled-coil polypeptides.

The interhelical electrostatic interactions which stabilize the peptide in the dimeric state are present in the SSP structures but not in the CSP series of polypeptides (see FIGS. 4b illustrating SSP4 and 4a illustrating CSP1, respectively). Thus, although the CSP series fold to a stable amphipathic helix, the interchain forces are not sufficiently strong to maintain a dimeric structure in the presence of membranes or membrane-like lipid monolayers. Interactions between the hydrophobic face of CSP series peptides and other hydrophobic molecules compete effectively with dimer formation. Studies of HIV and influenza virus derived peptide sequences have shown that only those fusion peptides which have a critical pressure for insertion into POPG monolayers greater than 30 mN/M are likely to induce the disruption of synthetic (model) lipid bilayers in vitro [Rafalski et al., (1990) Biochemistry 29:7917–7922]. CSP series peptides have a critical pressure of 45 mN/M for insertion into POPG monolayers. In contrast, SSP series peptides, which are stabilized by two interhelical salt bridges per heptad, dimerize rather-than interact with other hydrophobic surfaces and have critical pressures of only 30 mN/M for insertion into POPG monolayers.

Thus, the novel synthetic storage proteins described in this invention represent a particular subset of possible coiled-coil polypeptides. Not all polypeptides which adopt an amphipathic alpha helical conformation in aqueous solution are suitable for the applications described here as was demonstrated with the CSP series of polypeptides.

The following rules derived from Applicants' work define the SSP polypeptides that Applicants claim as their invention:

The synthetic polypeptide comprises n heptad units (d e f g a b c), each heptad being either the same or different, wherein:

n is at least 4;

a and d are independently selected from the group consisting of Met, Leu, Val, Ile and Thr;

e and g are independently selected from the group consisting of the acid/base pairs Glu/Lys, Lys/Glu, Arg/Glu, Arg/Asp, Lys/Asp, Glu/Arg, Asp//Arg and Asp/Lys; and b, c and f are independently any amino acids except Gly or Pro and at least two amino acids of b, c and f in each heptad are selected from the group consisting of Glu, Lys, ASp, Arg, His, Thr, Ser, Asn, Gln, Cys and Ala.

Construction of *E. coli* Expression Vector

Figure 5:
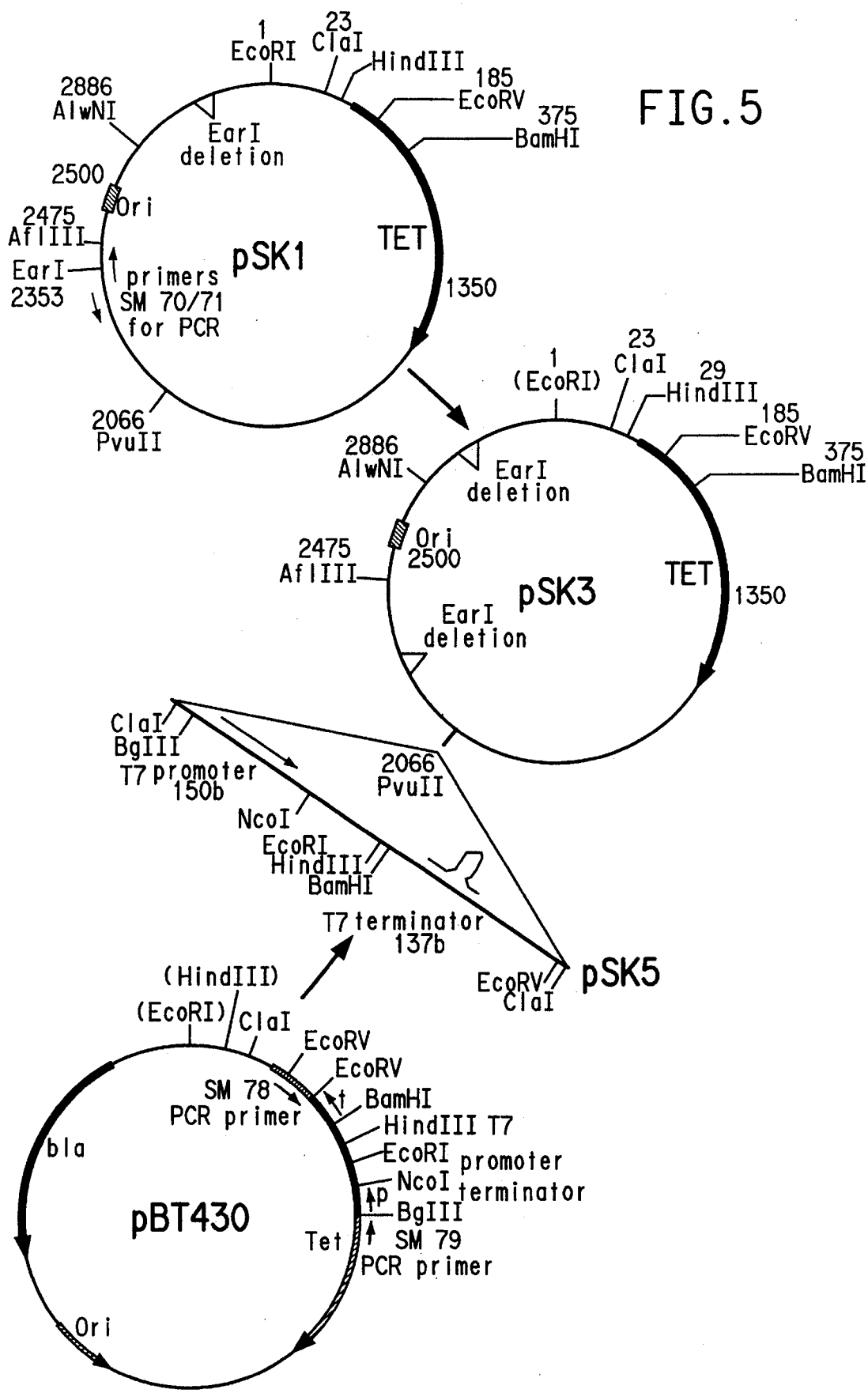
FIG. 5 depicts the strategy for creating a vector (pSK5) for use in construction and expression of the SSP gene sequences.

Applicants designed the strategy shown in FIG. 5 to construct the appropriate gene sequences to produce the polypeptides described above in *E. coli* (see also Example 5). This strategy required a vector for expression of gene products in *E. coli* which did not contain EarI restriction endonuclease sites. Other requirements were that the vector contain the bacteriophage T7 promoter, a translation leader sequence, the transcription terminator for high level expression in E. coli, and appropriate cloning sites for insertion of the gene sequences described below. Applicants also preferred the use of tetracycline resistance as a selectable marker rather than the ampicillin resistance carried on most expression vectors. Plasmids carrying the tetracycline resistance marker are less likely to be lost from cells in broth cultures because it is easier to maintain selection pressure for plasmid maintenance.

The vector pSK5 was constructed in several steps as shown in FIG. 5: (1) Plasmid pSK1 was a spontaneous deletion of the ampicillin gene region of pBR322 including the associated EarI site. (2) Plasmid pSK2 was derived by a polymerase chain reaction (PCR) (Cetus Corporation, Emeryville, Calif.) amplification of the entire pSK1 plasmid using primers SM70 (SEQ ID NO:9) and SM71 (SEQ ID NO:10) at sites which excluded the EarI site at base 2353. (3) Plasmid pSK3 was made by removing the EcoRI site at base 1 of pSK2 by cutting with EcoRI, filling in the site with the Klenow fragment of DNA polymerase and religating the vector. (4) In pBT430, a derivative of pET-3a [Rosenberg et al., (1987) Gene 56:125–135], the NdeI site at the ATG translation initiation site was altered by in vitro mutagenesis to an NcoI site. The T7 promoter/terminator sequences from plasmid pBT430 were amplified by PCR, blunt ended by filling in with Klenow enzyme, kinased and ligated into the PvuII site of pSK3 to create pSK5. Restriction endonuclease digestion analysis and DNA sequence analysis confirmed the orientation and integrity of the PCR fragment in pSK5.

Figure 6:
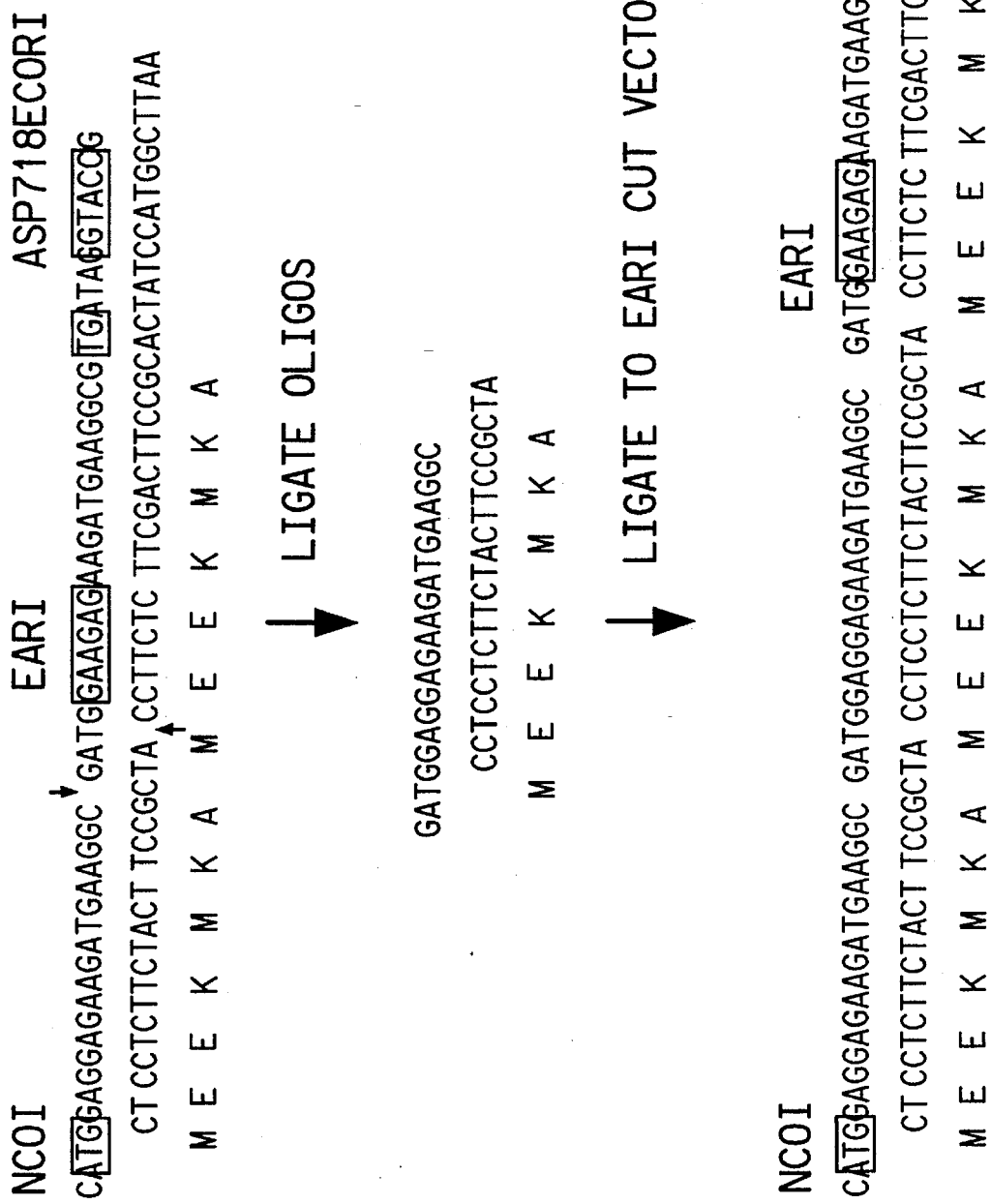
FIG. 6 shows the strategy for inserting oligonucleotide sequences into the unique EarI site of the base gene sequence.

Design of Gene Sequences Based on Peptide Sequences for Coiled-coil Synthetic Storage Proteins To produce in vivo the polypeptides described above Applicants designed DNA sequences which encoded the set of polypeptides SSP5,7,8,9,10 and 11 (SEQ ID NO:2,3,4,5, and 6). Codons were chosen from those preferable for translation in plants and E. coli. The DNA sequences were generated as oligonucleotides using an ABI DNA synthesizer and were inserted into a plasmid vector as shown in FIG. 6.

I. The first strategy for cloning these genes was as follows: The vector pSK5 was cleaved to completion with NcoI and EcoRI, mixed with kinased oligonucleotides SM80 (SEQ ID NO:14) and SM81 (SEQ ID NO:13) and ligated. From this ligation, the plasmid pSK6 was produced which contained the "base gene" sequences of oligonucleotides SM80 (SEQ ID NO:14) and SM81 (SEQ ID NO:13). The oligonucleotide insert for this "base gene" encoded 14 amino acids (two repeats of SSP5 sequence, SEQ ID NO:111). In addition, the "base gene" sequence had a unique EarI site into which repeated units of the various gene sequences could be inserted. EarI restriction endonuclease is unusual in that the cut site on the DNA is 4 bases 5' of the recognition site on the top strand and 1 base 3' of the recognition site on the bottom strand leaving a 5' overhang which is specific for the particular sequence:

```
5'-GAAGGC-3'          5'-GATGGAAGAG-3'¹
3'-CTTCCGCTA-5'       3'   -CCTTCAC-5'
                             EARI
```
¹nucleotides 21-31 of SEQ ID NO:13

This feature allows oligonucleotides with appropriate overhanging sequences to insert in this site in only one orientation. The 21-base oligonucleotides for the representative sequences in FIG. 6 were ligated to obtain multimeric sequences which were then ligated directly into the EarI site of the base gene.

Large multimers (>8 n) of the 21-base oligonucleotide sets SM84/SM85 (SEQ ID NO:15/16) (SSP5) and SM82/SM83 (SEQ ID NO:17/18) (SSP7) were isolated from 18% polyacrylamide gels. The ligated oligonucleotides displayed a ladder array of multimeric forms on these gels. Bands which appeared to be greater than 8 n (168 bp) were cut from the gels, eluted and purified by ethanol precipitation. These gel-purified oligonucleotide multimers were ligated with EarI digested pSK6 vector. Tetracycline-resistant transformants were screened by restriction-digest analysis and double-stranded sequencing. Although most inserts were 2 n (42 bp) or greater, no clones were isolated with greater than 5 n (105 bp) inserts.

Another method of enriching for multimeric forms of the insert oligonucleotides used was purification of the ligated multimeric forms by HPLC. This method separated DNA fragments on the basis of size on a DEAE-NPR ion exchange column with a NaCl gradient. Ligated oligonucleotide sets SM82/83 (SEQ ID NO:17/18)(SSP7), SM84/85 (SEQ ID NO:15/16) (SSP5), SM86/87 (SEQ ID NO:19/20) (SSP8), SM88/89 (SEQ ID N0:21/22) (SSP9), SM90/91 (SEQ ID NO:23/24) (SSP10), SM92/93 (SEQ ID NO:25/26) (SSP11), were injected onto the column, eluted, and fractions were collected and pooled based on known retention times for DNA size standards. Multimeric forms of the oligonucleotide sets of 6 n (126 bp) or greater were purified and the sizes confirmed on polyacrylamide gels. The purified oligonucleotides were ligated into EarI digested pSK6 and tetracycline-resistant transformants selected in E. coli strain DH5α. Clones were screened by restriction digests and sequencing. As with the gel purification, most clones had inserts of 2 n (42 bp) or greater but none of the inserts were greater than 6 n (126 bp) in length. From this procedure Applicants obtained gene sequences coding for each of the test polypeptide sequences described previously (SEQ ID NO:2–7 and 83).

TABLE 5

| Clone # | SEQ ID NO: | Sequence by Heptad Amino Acid Repeat (SSP)¹ | SEQ ID NO: |
|---|---|---|---|
| 82-4 | 44 | 7.7.7.7.7.7.5 | 45 |
| 84-H3 | 46 | 5.5.5.5 | 47 |
| 86-H23 | 48 | 5.8.8.5 | 49 |
| 88-2 | 50 | 5.9.9.9.5 | 51 |
| 90-H8 | 52 | 5.10.10.10.5 | 53 |
| 92-2 | 54 | 5.11.11.5 | 55 |

¹Refer to Table 3

In Table 5, the first and last SSP5 heptads flanking the underlined sequence represent the base gene sequence. Insert sequences are underlined. Clone numbers including the letter "H" designate HPLC-purified oligonucleotides. The loss of the first base gene repeat in clone 82-4 (SEQ ID 44) is believed to result from homologous recombination of the base gene repeat 5.5.

The strategy of gene construction outlined above advantageously allows the mixing of gene sequences simply by alternating insertion of the various 21 bp oligonucleotides into the EarI site. Since the EarI enzyme does not cleave at the recognition site, the site remains intact regardless of insertion at the cleavage point. Therefore, any gene sequence generated in a "first round" as above, may be lengthened and polypeptide sequences combined in any order by subsequent oligonucleotide or DNA fragment insertion into the EarI cleavage site. It may be advantageous to synthesize longer oligonucleotide versions of these insert genes (ex: 84 bases=4 n) to produce longer gene sequences. Alternatively, other strategies for amplifying gene segments may be employed to construct longer gene sequences [Kempe et al., (1985) Gene. 39:239–245].

Applicants noted that even with the 2 n repeat of the base gene stall segments of DNA were sometimes deleted when maintained in *E. coli* strain JM103 (rec +). This may have been due to homologous recombination. To eliminate this possibility Applicants routinely transformed the insert constructs into a recA-*E. coli* strain DH5α [supE44 del lacU169 (phi 80 lacZ del M15) hsdR17 recA1 endA1 gyr196 thi1 relA1]). Since these repetitive sequences may present a similar problem when transformed into recombination-proficient Agrobacterium and plant cells, the DNA sequences were redesigned to be less repetitive and therefore less recombinogenic. To do this, Applicants used alternative codons and/or mixed several polypeptide sequences. Applicants synthesized these oligonucleotides as 84-mers to assure longer initial gene sequences.

sequences. These sequences were designed to avoid exact repeats of sequence at the DNA level that might stimulate homologous recombination and deletion or rearrangement of the genes in bacterial or plant cells. Again, codons were chosen which are known to be preferred in soybean, corn and *E. coli* [Campbell et al. (1990) Plant Physiol. 92:1–11]. In addition, Applicants designed gene sequences to maximize stability of the mRNA based on published data on expression of foreign genes in plant cells [Perlak, F. J., Fuchs, R. L., Dean, D. A., McPherson, S. L., and Fischhoff, D. A. PNAS 88, 3324–3328 (1991)]. All DNA sequences code for amino acid sequences that fit the parameters outlined previously.

Figure 9A:
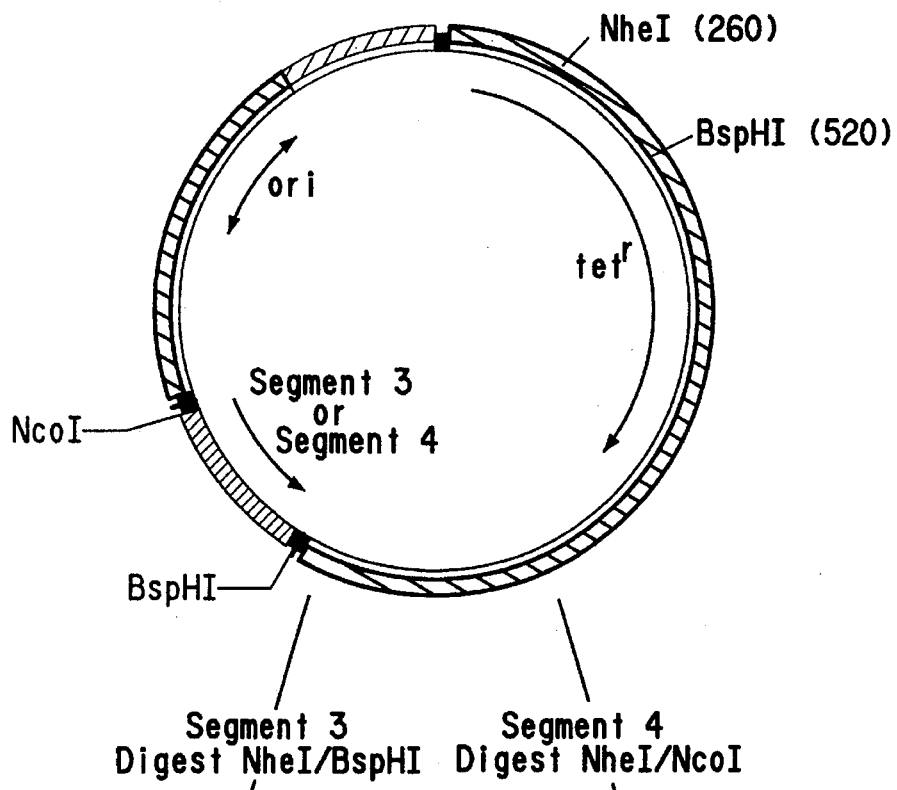
FIG. 9A illustrates the restriction digestion scheme of the plasmid from which component fragments are derived for carrying out a strategy of multiplying non-repetitive gene "segments", said strategy resulting in in-frame gene fusions.
Figure 9B:
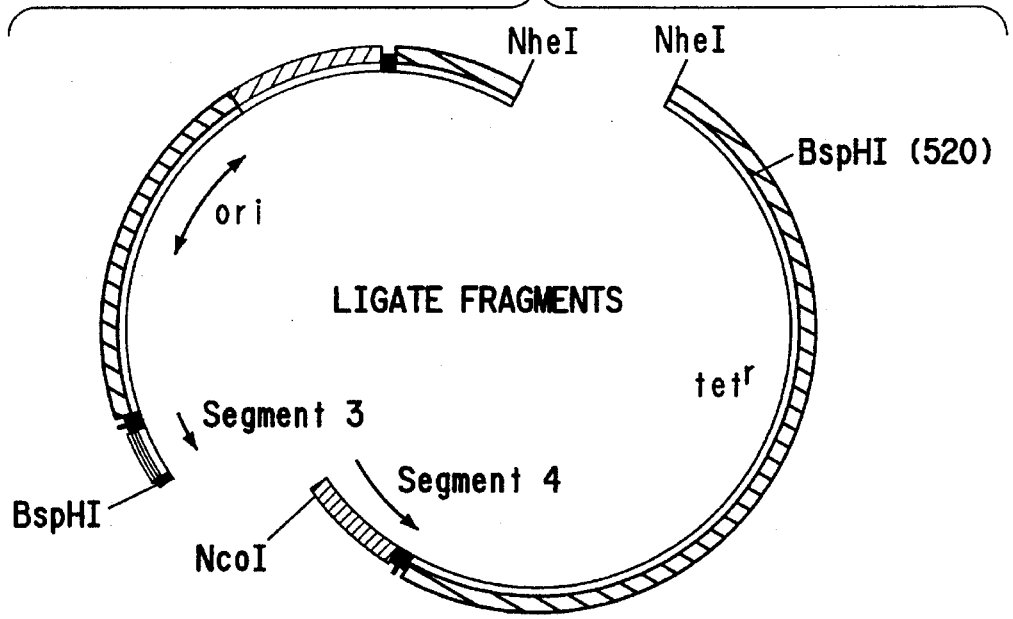
FIG. 9B illustrates the ligation of fragments derived from the plasmid of FIG. 9A wherein the result will be multiplication of non-repetitive gene "segments" such that gene fusions are in-frame.

The strategy for construction of this second generation of gene sequences is depicted in FIGS. 8 and 9. The first step was the insertion of oligonucleotide sequences SM107/106 (SEQ ID:92/93) encoding a base gene of 16 amino acids into the NcoI/EcoRI sites of the vector pSK5. The features of this base gene include an unique EarI site for subsequent inser-

```
          M  E  E  K  M  K  A  M  E  E  K  M  K
SM96  5'-GATGGAGGAAAAGATGAAGGCGATGGAGGAGAAAATGAAA
SM97  3'     CCTCC TTT TCT ACTTCC GCT ACCTCC TCT TTT ACTTT

A  M  E  E  K  M  K  A  M  E  E  K  M  K  A          (SEQ ID NO:2)
          GCTATGGAGGAAAAGATGAAAGCGATGGAGGAGAAAATGAAGGC-3'           (SEQ ID NO:88)
          CGATACCT CCT TTT CTACTT TCG CTACCT CCT CTT TTACTT CCGCTA-5'  (SEQ ID NO:89)

M  E  E  K  L  K  A  M  E  E  K  L  K
SM98  5'-GATGGAGGAAAAGCTGAAAGCGATGGAGGAGAAACTCAAG
SM99  3'     CCTCC TTT TCGACTTTC GCT ACCTCC TCT TTG AGTTC

A  M  E  E  K  L  K  A  M  E  E  K  L  K  A          (SEQ ID NO:3)
          GCTATGGAAGAAAAGCTTAAAGCGATGGAGGAGAAACTGAAAGC-3'           (SEQ ID NO:27)
          CGATACCTTC TTT TCG AATTTC GCATCCTCC TCT TTG ACTTCC GCTA-5'   (SEQ ID NO:28)

M  E  E  K  L  K  K  M  E  E  K  L  K
SM100 5'-GATGG AGGAAAAGCTTAAGAAGATGGAAGAAAAGCTGAAA
SM101 3'     CC TCC TTT TCG AATTCT TCT ACCTTC TTT TCG ACTTT

M  E  E  K  L  K  K  M  E  E  K  L  K  W            (SEQ ID NO:83)
          TGGATGGAGGAGAAACTCAAAAAGATGGAGGAAAAGCTTAAATG-3'           (SEQ ID NO:29)
          ACCT ACCTCC TCT TTG AGTTTT TCA TCCTCC TTT TCG AATTTACCTA-5'  (SEQ ID NO:30)
```

These oligonucleotides were kinased and ligated into the EarI site of clones 82-4 (SEQ ID NO:44) and 84-H3 (SEQ ID NO:46) respectively to create clones 2-9 (polypeptide sequence=SSP7.7.7.7.7.8.9.8.9.5) (SEQ ID NO:57), clone 3-5 polypeptide sequence=7.7.7.7.7.7.5.5) SEQ ID NO:91) and 5-1 (polypeptide sequence=SSP5.5.5.7.7.7.7.5) (SEQ ID NO:59). Sequences similar to these designs could be used to construct genes coding for any of the polypeptides or any combination of the polypeptides disclosed herein. The length of the coding region can be increased by a series of insertions of such oligonucleotide sequences into the EarI site of the base gene. Alternatively, the coding sequences can be constructed by insertion of a different base gene with any unique site for subsequent insertion of heptad coding units. Such a gene could also be constructed by generating a series of oligonucleotides with long (9–10 b) overhanging ends which could be ligated together into the NcoI/EcoRI sites of pSK5 or the EarI site of pSK6 forming a several hundred base sequence.

II. A second generation of SSP genes were designed to incorporate even more variation in DNA and amino acid tion of 63 base pair non repetitive "segments" and an unique BspHI site at the 3' end of the gene to allow duplication of the "segments" as described in FIG. 9 [Kempe et al., (1985) Gene. 39:239–245]. Crude "segment" oligonucleotide sets SM110/111 (SEQ ID NO:94/95), SM112/113 (SEQ ID NO:98/99), SM114/115 (SEQ ID NO:102/103) were annealed and ligated into the EarI site to create three separate clones: pSKseg3, pSKseg4 and pSKseg5. In these "segment" clones, the DNA sequences are as non-repetitive as possible within the limits of codon usage and amino acid sequence requirements. Applicants constructed a 107 amino acid gene sequence by joining the three gene segments using the multiplication scheme depicted in FIG. 9 and described in Example 5. The resultant clone was designated pSKseg 534.

Table 6 is a summary of the relevant amino acid content of the proteins encoded by clones derived from these several cloning schemes which were selected for transformation into plants.

TABLE 6

Summary of important amino acid content of SSP Sequences used for plant transformations

| Clone | SEQ ID | Protein Sequence | SEQ ID | % lys | % met | % trp |
|---|---|---|---|---|---|---|
| 86–H23 | 48 | MEEKMKAMEEKLKKMEEKLKKMEEKMKA | 49 | 36 | 21 | 0 |
| 88–2 | 50 | MEEKMKAKKLKWMEEKLKWMEEKLKW MEEKMKA | 51 | 33 | 18 | 9 |
| 90–H8 | 52 | MEEKMKAMEEKMKKMEEKMKKMEEKMKK MEEKMKA | 53 | 37 | 28.6 | 0 |
| 3–5 | 90 | MEEKLKAMEEKLKAMEEKLKAMEEKLKA MEEKLKAMEEKLKAMEEKMKAMEEKMKA | 91 | 28.6 | 16 | 0 |
| seg 534 | 104 | MEEKMKKLKEEMAKMKDEMWKLKEEMKK LEEKMKVMEEKMKKLEEKMKAMEDKMKW LEEKMKKLEEKMKVMEEKMKKLEEKMKA MEDKMKWLEEKMKKLEEKMKVMK | 105 | 35 | 21 | 2.8 |

Expression of SSP polypeptides in E. coli

The SSP sequences constructed as described above were expressed in E. coli using the bacteriophage T7 RNA polymerase/T7 promoter system [Studier et al., (1990) Methods in Enzymology 185:60–89]. In strain BL21 (DE3) [hsdS gal (lambda cIts857 ind1 Sam7 nin5 lac UV5-T7 gene1)], T7 polymerase was produced from a chromosomal copy of the polymerase coding sequence under control of the lacZ promoter. Derepression of the lacZ promoter by the addition of isopropylthiogalactoside (IPTG) induced expression of T7 RNA polymerase in the cells. In strains DH5α or HMS174 [recA hsdR rifR] there is no endogenous T7 polymerase coding sequence. The T7 polymerase gene and gene product can be delivered to these cells by infection with bacteriophage lambda CE6. This phage carries the T7 polymerase gene and is capable of infection of these strains but is non-lytic on both strains. The procedures for inductions were as described by Studier et al., [(1986) J. Mol. Biol. 189:113–130].

Cells carrying plasmids containing the SSP coding sequences placed downstream from the T7 promoter sequence were induced with IPTG or by the addition of lambda CE6 phage during late log phase growth. Applicants noted that the turbidity of the induced cultures tended to level off or drop slightly after induction but there was no evidence of lytic activity with induction of gene products. Samples were taken one to three hours after induction for in vitro labelling experiments using $^{35}$S methionine. Because of the high methionine content of the SSP proteins and the overexpression from the T7 promoter, Applicants expected these polypeptides would incorporate a greater amount of labelled methionine than any other protein in the cell. $^{35}$S labelling experiments were performed as described by Studier et al., [(1986) J. Mol. Biol. 189:113–130]. Unlabelled cell samples were taken one to three hours after induction and concentrated ten fold by centrifugation.

Samples of both unlabelled and labelled proteins from cell extracts were separated on 18% (75:1 acrylamide:bis). SDS-polyacrylamide gels. Staining of the gels with Coomassie blue revealed additional proteins produced in the induced culture samples but not in uninduced cultures. These proteins were of the approximate size expected for each of the synthetic genes described above. It should be noted that these alpha-helical proteins tended to run faster on the gel than predicted from the globular protein size standards. In addition, there was some effect of sequence on the migration rate of particular polypeptides in the gels. Proteins labelled with $^{35}$S methionine were visualized by autoradiography of the gels. As anticipated, the SSP proteins were labelled well above background levels of endogenous E. coil proteins. Based on staining of in vitro synthesized peptides run in similar gel systems, Applicants estimate the production of these peptides to be approximately 40 mg/L of induced culture.

The size of the protein gene products and their intense labelling with $^{35}$S methionine were used to identify particular polypeptide products. In addition, Western blots of these gels were reacted with antibodies raised against in vitro synthesized polypeptides SSP(5)$_4$ (SEQ ID NO:2) or SSP(7)$_4$ (SEQ ID NO:3) or with anti-GST-SSP- 3-5. Secondary antibodies conjugated to horseradish peroxidase and a chemiluminescence detection system (Amersham) were used to detect the antibody-reactive proteins. Tests of the specificity of the anti-SSP antibodies using dot blots of non-denatured chemically synthesized peptides showed that the anti-SSP antibodies cross-react with various SSP sequences. However, when the peptides are denatured in a gel system, the reaction of the antibodies is more specific. The antibodies raised against a particular SSP polypeptide reacted specifically with that SSP polypeptide induced in E. coli cultures. That is, anti-SSP5 reacted with proteins containing SSP5 sequence and anti-SSP7 reacted with proteins containing SSP7 sequence. The specificity of these interactions confirmed the sequences of the induced proteins.

The synthetic storage proteins can also be expressed in E. coli as gene fusion products. The Pharmacia pGEX™ system was used to produce a fusion protein consisting of glutathione-S-transferase and SSP-3-5. This fusion protein was purified by affinity chromatography and used to immunize rabbits. The resulting serum containing anti-GST-SSP-3-5 antibodies was used as a detection reagent for further studies of transgenic cells expressing the SSP-3-5 protein (SEQ ID NO:91).

This invention can be used to produce large quantities of SSP polypeptides or total protein enriched in essential amino acids via fermentation of E. coli or other transformed microorganisms. The DNA sequences of the invention can be operably linked to a suitable regulatory sequence comprising a promoter sequence, a translation leader sequence and a 3' noncoding sequence. The chimeric gene can then be introduced into a microorganism via transformation and the transformed microorganism can be grown under conditions resulting in high expression of the chimeric gene. The cells containing protein enriched in essential amino acids can be collected, the protein extracted and purified. If desired, a protein carrier such as glutathione-S-transferase can be used to simplify purification of the SSP polypeptide. If a recognition site for thrombin or factor X is included between the carrier protein and the synthetic polypeptide (as in the case of the pGEX™ system) the SSP polypeptide can be easily separated from the carrier protein.

Alternatively, methods of purification may be based on the physical properties of the proteins or (in the case of fusion proteins) may be affinity based. The proteins are small relative to most naturally occurring proteins. They also are easily refolded from solutions of denaturant simply by removal of the denaturant. One strategy to purify the SSPs is to lyse the cells in 6M urea, separate the protein mixture using gel filtration chromatography, reverse-phase chromatography or ion exchange chromatography and finally remove the urea by dialysis. Another exploitable property of the proteins is their lysine content. For those SSPs which are positively charged, anion exchange resins can be used to remove most proteins from the crude mixture without binding the SSPs.

Expression of SSPs in Plants

A preferred class of heterologous hosts for the expression of the coding sequence of the SSP genes are eukaryotic hosts, particularly the cells of higher plants. Particularly preferred among the higher plants and the seeds derived from them are soybean, rapeseed (*Brassica napus, B. campestris*), sunflower (*Helianthus annus*), cotton (*Gossypium hirsutum*), corn, tobacco (*Nicotiana tobacum*), alfalfa (*medicago sativa*), wheat (Triticum sp), barley (*Hordeum vulgare*), oats (*Avena sativa*, L), sorghum (*Sorghum bicolor*), rice (*Oryza sativa*), and forage grasses. Expression in plants will use regulatory sequences functional in such plants.

The expression of foreign genes in plants is well-established [De Blaere et al., (1987.) Meth. Enzymol. 153:277–291]. The promoter chosen to drive the expression of the coding sequence is not critical as long as it has sufficient transcriptional activity to accomplish the invention by increasing the level of translatable mRNA for SSPs in the desired host tissue. Preferred promoters for expression in all plant organs, and especially for expression in leaves include those directing the 19S and 35S transcripts in cauliflower mosaic virus [Odell et al., (1985) Nature 313:810–812; Hull et al., (1987) Virology 86:482–493], small subunit of ribulose 1,5-bisphosphate carboxylase [Morelli et al., (1985) Nature 315:200; Broglie et al., (1984) Science 224:838; Hererra-Estrella et al., (1984) Nature 310:115; Coruzzi et al., (1984) EMBO J. 3:1671; Faciotti et al., (1985) Bio/Technology 3:241], maize zein protein [Matzke et al., (1984) EMBO J. 3: 1525], and chlorophyll a/b binding protein [Lampa et al., (1986) Nature 316:750–752] and the chemically inducible promoter In2-2 [PCT/US90/01210] and its derivatives.

The selection of promoters will be driven by the specific organs of the plant where expression is desired. Preferred promoters allow expression of the protein specifically in seeds. This application is especially useful because seeds are the primary source of vegetable protein. Also, seed-specific expression avoids any potential deleterious effect in non-seed organs. Examples of seed-specific promoters include, but are not limited to, the promoters of seed storage proteins, which represent more than 50% of total seed protein in many plants. The seed storage proteins are strictly regulated, being expressed almost exclusively in seeds in a highly organ-specific and stage-specific manner [Higgins et al., (1984) Ann. Rev. Plant Physiol. 35:191–221; Goldberg et al., (1989) Cell 56:149–160; Thompson et al., (1989) BioEssays 10:108–113]. Moreover, different seed storage proteins may be expressed at different stages of seed development.

There are currently numerous examples for seed-specific expression of seed storage protein genes in transgenic dicotyledonous plants. These include genes from dicotyledonous plants for bean β-phaseolin [Sengupta-Gopalan et al., (1985) Proc. Natl. Acad. Sci. USA 82:3320–3324; Hoffman et al., (1988) Plant Mol. Biol. 11:717–729], bean lectin [Voelker et al., (1987) EMBO J. 6:3571–3577], soybean lectin [Okamuro et al., (1986) Proc. Natl. Acad. Sci. USA 83:8240–8244], soybean kunitz trypsin inhibitor [Perez-Grau et al., (1989) Plant Cell 1:095–1109], soybean β-conglycinin [Beachy et al., (1985) EMBO J. 4:3047–3053; Barker et al., (1988) Proc. Natl. Acad. Sci. USA 85:458–462; Chen et al., (1988) EMBO J. 7:297–302; Chen et al., (1989) Dev. Genet. 10:112–122; Naito et al., (1988) Plant Mol. Biol. 11:109–123], pea vicilin [Higgins et al., (1988) Plant Mol. Biol. 11: 683–695], pea convicilin [Newbigin et al., (1990) Planta 180:461], pea legumin [Shirsat et al., (1989) Mol. Gen. Genetics 215:326]; rapeseed napin [Radke et al., (1988) Theor. Appl. Genet. 75:685–694] as well as genes from monocotyledonous plants such as for maize 15 kD zein [Hoffman et al., (1987) EMBO J. 3213–3221; Schernthaner et al., (1988) EMBO J. 7:1249–1253; Williamson et al., (1988) Plant Physiol. 88:1002–1007], barley β-hordein [Marris et al., (1988) Plant Mol. Biol. 10:359–366] and wheat glutenin [Colot et al., (1987) EMBO J. 6:3559–3564]. Moreover, promoters of seed-specific genes operably linked to heterologous coding sequences in chimeric gene constructs also maintain their temporal and spatial expression pattern in transgenic plants. Such examples include *Arabidopsis thaliana* 2S seed storage protein gene promoter to express enkephalin peptides in Arabidopsis and *B. napus* seeds [Vandekerckhove et al., (1989) Bio/Technology 7:929–932], bean lectin and bean β-phaseolin promoters to express luciferase [Riggs et al., (1989) Plant Sci. 63:47–57], and wheat glutenin promoters to express chloramphenicol acetyl transferase [Colot et al., (1987) EMBO J. 6:3559–3564].

Of particular use in the invention will be the heterologous promoters from several extensively-characterized soybean seed storage protein genes such as those for the Kunitz trypsin inhibitor [Jofuku et al., (1989) Plant Cell 1:1079–1093; Perez-Grau et al., (1989) Plant Cell 1:1095–1109], glycinin [Nielson et al., (1989) Plant Cell 1:313–328], β-conglycinin [Harada et al., (1989) Plant Cell 1:415–425]. Promoters of genes for α'- and β-subunits of soybean β-conglycinin storage protein will be particularly useful in expressing the SSP mRNA in the transgenic plant cotyledons at mid- to late-stages of soybean seed development [Beachy et al., (1985) EMBO J. 4:3047–3053; Barker et al., (1988) Proc. Natl. Acad. Sci. USA 85:458–462; Chen et al., (1988) EMBO J. 7:297–302; Chen et al., (1989) Dev. Genet. 10:112–122; Naito et al., (1988) Plant Mol. Biol. 11:109–123]. This is because: a) there is very little position effect on their expression in transgenic seeds, and b) the two promoters show different temporal regulation:the promoter for the α'-subunit gene is expressed a few days before that for the β-subunit gene.

Also of particular use in the invention will be the heterologous promoters from several extensively-characterized corn seed storage protein genes such as those from the 10 kD zein [Kirihara et al., (1988) Gene 71:359–370], the 27 kD zein [Prat et al., (1987) Gene 52:51-49; Gallardo et al., (1988) Plant Sci. 54:211–281], and the 19 kD zein [Marks et al., (1985) J. Chem. 260:16451–16459]. The relative transcriptional activities of these promoters in corn are known [Kodrzyck et al., (1989) Plant Cell 1:105–114] giving a basis for choosing a promoter for use in chimeric gene constructs for corn. The promoter for the globulin 1 or globulin 2 genes of corn could also be used to express the SSP gene sequences specifically in the embryo of corn seeds [Belanger et al., (1989) Plant Physiol. 91:636–643].

Maximizing the expression of these genes in plants may also require careful attention to the design of the gene sequences to promote mRNA stability and translatability. Applicants have constructed gene sequences using preferred codons for expression in plants and bacteria. For corn and soybean, codons XUA and XCG were not used [Campbell et al. (1990) Plant Physiol. 92:1–11]. Repeating runs of like bases (AAAA, TTTT, CCCC, GGGG, etc.), poly A+ recognition sequences (AATTAA) and specific sequences that are thought to cause mRNA instability (AACCAA, ATTTA) (Perlak et al. (1991) PNAS 88:3324–3328), were avoided. The G/C to A/T content was adjusted as close as possible to 50/50.

The proper level of expression of SSP mRNA may require different chimeric genes using different promoters. Such chimeric genes can be transferred into host plants either together in a single expression vector or sequentially using more than one vector.

It is envisioned that the introduction of enhancers or enhancer-like elements into the promoter constructs will also provide increased levels of primary transcription of SSP genes. These elements include viral enhancers such as that found in the 35S promoter [Odell et al., (1988) Plant Mol. Biol. 10:263–272], enhancers from the opine genes [Fromm et al., (1989) Plant Cell 1:977–984], or enhancers from any other source that result in increased transcription when placed into a promoter operably linked to the nucleic acid fragment of the invention.

Of particular importance is the DNA sequence element isolated from the gene for the α'-subunit of β-conglycinin that can confer 40-fold seed-specific enhancement to a-constitutive promoter [Chen et al., (1988) EMBO J. 7:297–302; Chen et al., (1989) Dev. Genet. 10:112–122]. One skilled in the art can readily isolate this element and insert it within the promoter region of any gene in order to obtain seed-specific enhanced expression with the promoter in transgenic plants. Insertion of such an element in any seed-specific gene that is expressed at different times than the β-conglycinin gene will result in expression in transgenic plants for a longer period during seed development.

Any 3' non-coding region capable of providing a transcription termination signal, a polyadenylation signal and other regulatory sequences that may be required for the proper expression of the SSP coding region can be used to accomplish the invention. This would include 3ʳ end sequences from any source such that the sequence used gives the necessary regulatory information within its nucleic acid sequence for proper expression of the promoter/SSP coding region combination to which it is operably linked. Specific examples include the native 3' end of the 10 kD zein gene(s) from corn, the 3' end from any storage protein gene such as the 3' end of the soybean β-conglycinin gene or the bean phaseolin gene, the 3' end from viral genes such as the 35S or the 19S cauliflower mosaic virus transcripts, the 3' end from the opine synthesis genes, or the 3' ends of ribulose 1,5-bisphosphate carboxylase or chlorophyll a/b binding protein. The usefullness of different 3' non-coding regions is taught in the art [For example, see Ingelbrecht et al., (1989) Plant Cell 1:671–680].

DNA sequences coding for intracellular localization signals may be added to the SSP coding sequence if required for the proper expression of the proteins to accomplish the invention. For example, the monocot signal sequence of the 10 kD rein gene could be used in corn or other monocot transformants and the signal sequence from the β subunit of phaseolin from the bean *Phaseolus vulgaris*, or the signal sequence from the α' subunit of β-conglycinin from soybean [Doyle et al., (1986) J. Biol. Chem. 261:9228–9238], could be used in dicot transformants. Hoffman et al., [(1987) EMBO J. 6:3213–3221] showed that the signal sequence of the monocot precursor of a 15 kD rein directed the protein into the secretory pathway and was also correctly processed in transgenic tobacco seeds. However, the protein did not remain within the endoplasmic reticulum as is the case in corn. To keep the protein in the endoplasmic reticulum it may be necessary to add stop transit sequences. It is known in the art that the addition of DNA sequences coding for the amino acid sequence [lys-asp-glu-leu] at the carboxyl terminal of the protein keeps proteins in the lumen of the endoplasmic reticulum [Munro et al., (1987) Cell 48:899–907; Pelham (1988) EMBO J. 7:913–918; Pelham et al., (1988) EMBO J. 7:1757–1762; Inohara et al., (1989) Proc. Natl. Acad. Sci. U.S.A. 86:3564–3568; Hesse et al., (1989) EMBO J. 8:2453–2461]. In some plants seed storage proteins are located in the vacuoles of the cell. To obtain certain embodiments of the invention it may be necessary to direct the SSP proteins to the vacuole of these plants by adding a vacuolar targetting sequence. A short amino acid domain that serves as a vacuolar targetting sequence has been identified from bean phytohemagglutinin which accumulates in protein storage vacuoles of cotyledons [Tague et al., (1990) Plant Cell 2:533–546]. A carboxyl-terminal amino acid sequence necessary for directing barley lectin to vacoules in transgenic tobacco has also been described [Bednarek et al., (1990) Plant Cell 2:1145–1155]. Applicants' data-suggest that targetting signals are not required for accumulation of SSP proteins in tobacco seeds or rice protoplasts.

Construction of Chimeric Genes for Expression of SSPs in Plants

A significant increase in essential amino acids in the seeds of transformed plants requires expression of high levels of SSPs in a seed-specific manner. Expression of the synthetic storage protein sequences in plants was first accomplished by linking the SSP coding sequences to the 35S promoter from cauliflower mosaic virus and adding a 3' sequence from the nopaline synthase (NOS) gene. The strategy for this cloning is depicted in FIG. 10. The plasmid pMH40 contains the β-glucuronidase (GUS) gene coding sequence. The SSP sequences were inserted into the NcoI/Asp718 sites by removing the GUS gene sequences and replacing them with the SSP NcoI/Asp718 fragments. For initial transformation experiments to investigate the efficiency of translation of the SSP sequences in plants and to observe stability and localization of SSP proteins in plant cells, trangenic tobacco plants expressing the SSP proteins via the constitutive 35S promoter were generated.

Figure 11:
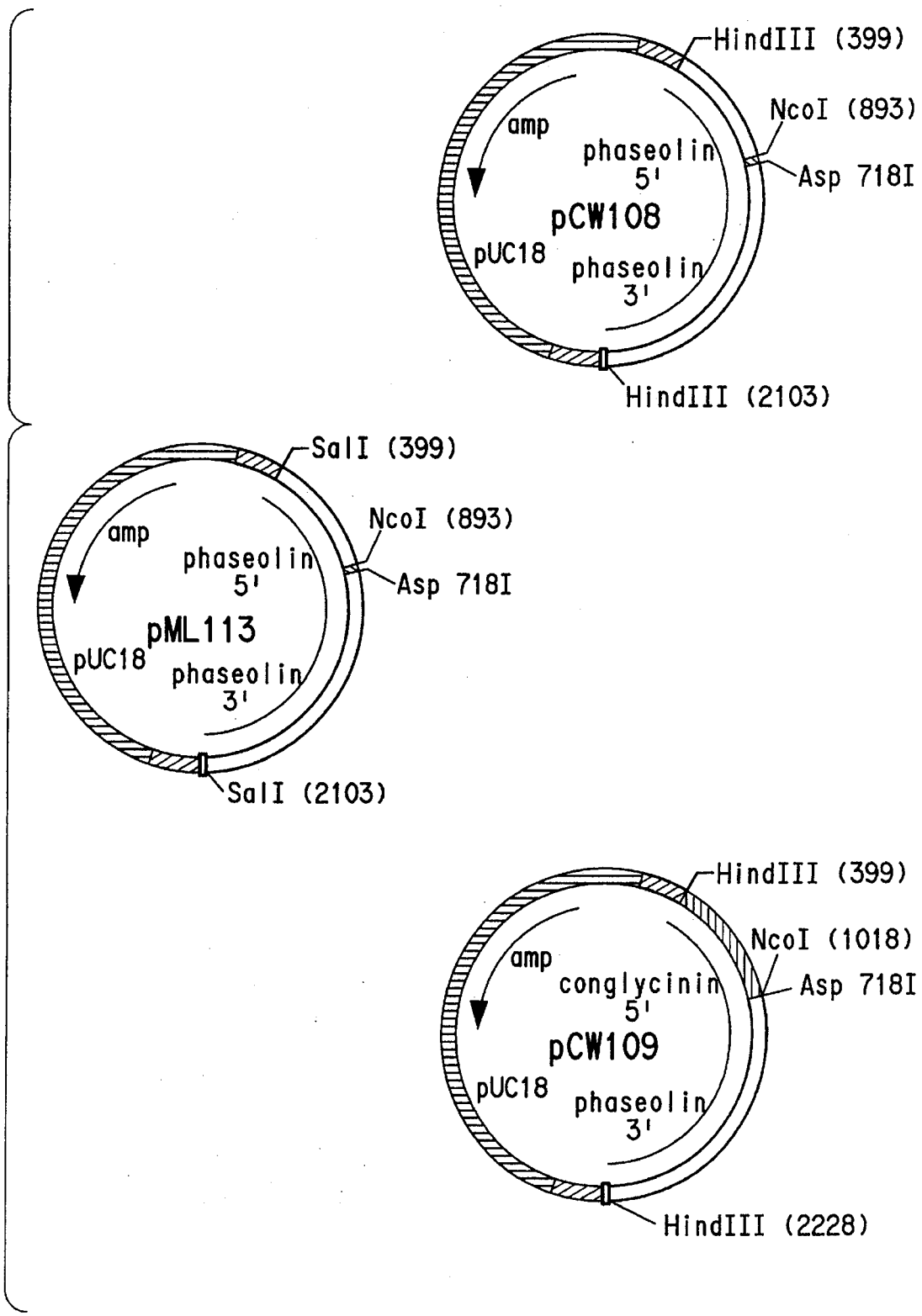
FIG. 11 shows the vectors containing seed specific promoter and 3' sequence cassettes. SSP sequences were inserted into these vectors using the NcoI and Asp718 sites as in FIG. 10.

Similar strategies were employed to insert the SSP-3-5 (SEQ ID NO:90) or SSPseg534 (SEQ ID NO:104) gene sequences into vectors containing the phaseolin promoter and 3' sequences (CW108, ML113) or the conglycinin promoter and phaseolin 3' sequences (CW109) as in FIG. 11. Fragments containing the promoter/SSP coding region/3' sequences were transferred to binary vectors as with the 35S promoter clones. These clones were utilized in subsequent transformations to generate tobacco plants.

Various methods of transforming cells of higher plants are available for use in Applicants' invention (see EPO 0 295 959 A2 and 0 138 341 A1). Such methods include those based on transformation vectors based on the Ti and Ri plasmids of Agrobacterium spp. Particularly preferred is the binary type of these vectors [Bevan (1984) Nucl. Acids. Res. 12:8711–8720]. Ti-derived vectors transformed a wide variety of higher plants, including monocotyledonous and dicotyledonous plants, such as soybean, cotton and rape [Pacciotti et al. (1985) Bio/Technology 3:241; Byrne et al. (1987) Plant Cell, Tissue and Organ Culture 8:3; Sukhapinda et al. (1987) Plant Mol. Biol. 8:209–216; Lorz et al. (1985) Mol. Gen. Genet. 199:178; Potrykus (1985) Mol. Gen. Genet. 199:183].

Figure 12:
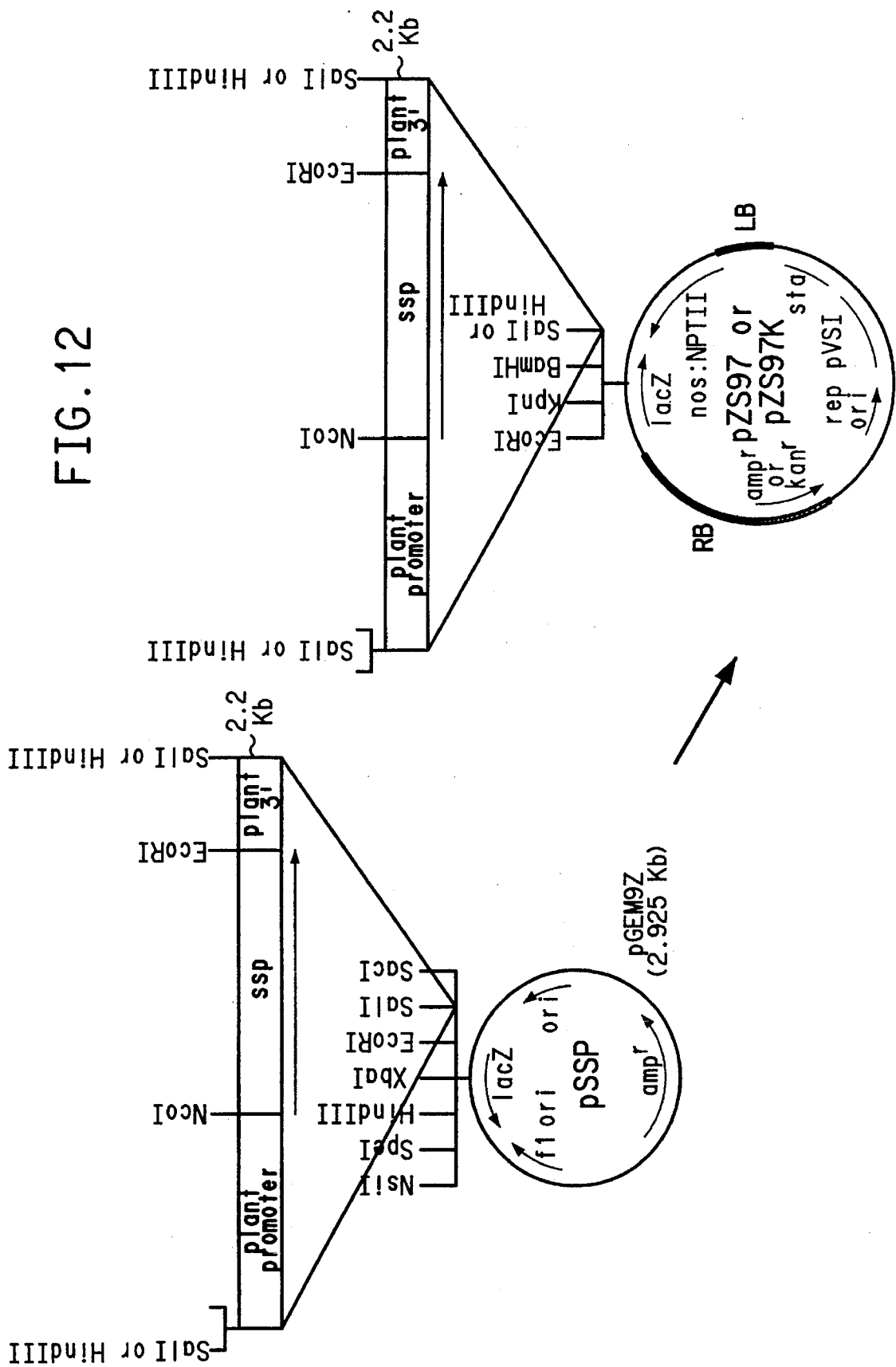
FIG. 12 shows the transfer of the chimeric SSP genes to the binary vector pZS97 or pZS97K for use in Agrobacterium transformation of plant tissue.

FIG. 12 shows the strategy for transferring the chimeric genes to binary vectors. Applicants cleaved the 35S::SSP-::NOS chimeric gene constructs from the pSSP plasmids by digesting the DNA with SalI. The 2.2 kb fragments were ligated individually into SalI-digested binary vector pZS97K which is part of a binary Ti plasmid vector system for Agrobacterium tumefaciens-mediated plant transformation. The vector contains: (1) the chimeric gene nopaline synthase promoter/neomycin phosphotransferase gene (nos-:NPT II) as a selectable marker for transformed plant cells [Bevan et al., (1983) Nature 304:184–186], (2) the left and right borders of the T-DNA of the Ti plasmid [Bevan, (1984) Nucl. Acids. Res. 12:8711–8720], (3) the $E.\ coli$ lacZ α-complementing segment [Vieria et al., (1982) Gene 19:259–267] with unique restriction endonuclease sites for EcoRI, KpnI, BamHI and Sal I, (4) the bacterial replication origin from the Pseudomonas plasmid pVS1 [Itoh et al., (1984) Plasmid 11:206–220], and 5) the bacterial neomycin phosphotransferase gene from Tn5 [Berg et al., (1975) Proc. Natl. Acad. Sci. U.S.A. 72:3628–3632] or β-lactamase as selectable markers for transformation of A. tumefaciens.

The binary vectors containing the chimeric SSP genes were transferred by tri-parental matings [Ruvkin et al., (1981) Nature 289:85–88] to Agrobacterium strain LBA4404/pAL4404 [Hockema et al., (1983) Nature 303:179–180]. The Agrobacterium transformants were used to inoculate tobacco leaf disks [Horsch et al., (1985) Science 227:1229–1231]. Transformed plants were regenerated in selective medium containing kanamycin or carbenicillin.

Other transformation methods are available to those skilled in the art, such as direct uptake of foreign DNA constructs [see EPO 0 295 959 A2], techniques of electroporation [see Fromm et al., (1986) Nature (London) 319:791] or high-velocity ballistic bombardment with metal particles coated with the nucleic acid constructs [see Kline et al., (1987) Nature (London) 327:70, and U.S. Pat. No. 4,945, 050].

Transformed cells can be regenerated with methods understood by those skilled in the art. Of particular relevance are the recently described methods to transform foreign genes into commercially important crops, such as rapeseed [see De Block et al., (1989) Plant Physiol. 91:694–701], sunflower [Everett et al., (1987) Bio/Technology 5:1201], soybean [McCabe et al., (1988) Bio/Technology 6:923; Hinchee et al., (1988) Bio/Technology 6:915; Chee et al., (1989) Plant Physiol. 91:1212–1218; Christou et al., (1989) Proc. Natl. Acad. Sci USA 86:7500–7504; EPO 0 301 749 A2], and corn [Gordon-Kamm et al., (1990) Plant Cell 2:603–618; Fromm et al., (1990) Biotechnology 8:833–839]

Analysis of SSPs in transgenic plants:

Transgenic tobacco plants containing various plant promoter/SSP gene sequence constructs were generated using Agrobacterium mediated transformation. Applicants analyzed these plants for the presence of the genes by PCR, for the copy number of the genes by Southern blot hybridization, for the transcription of the genes by Northern blot hybridization and for the accumulation of the proteins by Western blot as described in Example 9. A summary of this data is presented in Tables 7 and 8.

Applicants analyzed in detail transgenic plants carrying the 35S promoter/SSP3-5/NOS 3' gene sequences. PCR generated fragments and restriction digest analyses of the plant DNAs combined with the size of the mRNA species visualized on the Northern blot suggest that the SSP-3-5 gene sequence. (SEQ ID NO:90), despite its repetitive nature, is stable in plant cells. From the Western blotting data it is clear that the SSP-3-5 II protein (SEQ ID NO:91) is expressed in leaf tissue at levels up to 0.5% of the total cell protein (SEQ ID NO:70). The expression level in the leaves from the 35S promoter is positively correlated with the number of gene copies and the steady state level of mRNA. Expression of SSP-3-5 protein (SEQ ID NO:91) in seeds from the 35S promoter is limited to about 0.01%. Since the 35S promoter is known to express poorly in seeds, this finding does not suggest instability of the protein in seeds.

Analyses of transgenic tobacco plants carrying the phaseolin promoter/SSP-3-5 coding region and the phaseolin 3' sequences revealed that the SSP-3-5 gene sequence (SEQ ID NO:90) is stable and that expression of the gene product is correlated to mRNA levels. In these plants, the level of accumulation of the protein in the seeds is estimated to be 1–2% of the total seed protein. Amino acid analyses of the seeds from the primary transformants indicate that Applicants have altered the lysine content of tobacco seeds through the introduction of genes encoding the SSP sequences. This level of SSP expression in corn seeds would result in significant increases in lysine acid and methionine content.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. All publications including patents cited by Applicants herein are incorporated in their entirety by reference.

EXAMPLE 1

Chemical Synthesis of Coiled-coil Peptides

Peptides described in Tables 3 and 4 were synthesized on a Milligen 9050 solid phase peptide synthesizer using standard protocols suggested by the manufacturer. For peptides containing an alanine at position 21 the peptide was double-coupled at that position.

The columns were packed with 0.1 meq 9-fluorenyl-methyloxycarbonyl (Fmoc) PAL™ Resin (Milligen/Biosearch) mixed with four mass equivalents of glass beads (Sigma). The following protected Fmoc derivatives of the amino acids (Milligen/Biosearch) were used: Fmoc-L-Ala- O-pentafluorophenyl ester, Fmoc-L-Lys (N-tert-butoxy-carbonyl)-O-pentafluorophenyl ester, Fmoc-L-Met-pentafluorophenyl ester, Fmoc-L-Glu(O-t-butyl)O-pentafluorophenyl ester, Fmoc-L-Trp-O-pentafluorophenyl ester. In some cases nonesterified amino acids (Advanced ChemTech) mixed with 300 mg 2-(1H-benzotriazol- 1-yl)-1,1,3,3-tetramethyluronium hexafluorophosphate (HBTU) were employed.

An analog of the 56 amino acid peptide, SSP-3-5 (two amino acid changes: ala49 to Glu and met54 to leu).

SSP-3-5 (A/E)

MEEKLKAMEEKLKAMEEKLKAMEEKLKAMEEKLKA
MEEKLKAMEEKMKEMEEKLKA          (SEQ ID NO:112)

was synthesized on a Milligen/Biosearch Excell peptide synthesizer. The reaction vessel contained 0.05 meq F-moc PAL Resin (Milligen/Biosearch). The same protected Fmoc amino acids were used as above. The synthesis program was modified to acetylate unreacted peptide chains after each coupling reaction with a solution of acetic anhydride, pyridine, and 4-dimethylaminopyridine in dimethylformamide. The first alanine was double coupled. All coupling times were increased two to threefold over the manufacturer's suggestion.

Following completion of each synthesis, the resin was removed from the column by rinsing with methanol into a coarse sintered glass funnel. The material was washed well with methanol and then with diethyl ether. For cleavage of the peptide from the resin, it was placed into a 20 mL roundbottom flask. Five mL of cleavage solution [4.5 mL trifluoroacetic acid, 0.25 mL thioanisole, 0.15 mL ethanediol, 0.1 mL anisole] were added. The flask was stoppered and shaken on a rotary shaker at 200 rpm for 2 h at room temperature. The resin was then filtered through a coarse sintered glass frit into a 125 mL erlenmeyer flask. The resin was washed with 3 to 5 mL of trifluoroacetic acid and the washings combined with the filtrate. A stream of nitrogen was used to reduce the volume of the filtrate to 5 mL. Ice cold diethyl ether was added to precipitate the peptide (approximately 20 to 30 mL). The peptide was filtered through a fine sintered glass frit and washed with cold diethyl ether. The material was then dissolved with distilled water and lyophilized subsequent to further purification by reverse-phase HPLC.

Separations were performed on VYDAC $C_4$ or $C_{18}$ semi-preparative (1 cm diameter) or preparative (1 inch diameter) columns at a flow rate of approximately 4 mL/min/cm$^2$ using a two buffer system [buffer A: 0.1% trifluoroacetic acid (Pierce) in water (MilliQ); buffer B: 90% acetonitrile (J T Baker), 10% water, 0.1% trifluoroacetic acid]. Gradients varied with peptide sequence but typically began at close to 30% buffer B and linearly increased buffer B at a rate of 0.25%/min. The effluent was monitored at 220 nm and the major peak collected. The collected material was lyophilized and stored dry at 4°. Purified material was analyzed by fast atom bombardment mass spectroscopy, amino acid composition and, in some cases, protein sequencing to confirm the identity and purity of the synthetic materials.

EXAMPLE 2

Physical Characterization of Synthetic Peptides

Surface pressure was determined by the de Noy method [Adamson, (1976) The Physical Chemistry of Surfaces, Third Ed. John Wiley & Sons, New York] using a Fisher Autotensiomat Model 215. For monolayer insertion experiments, a monolayer of 1-palmitoyl, 2-oleyl phosphatidylcholine (POPG) was spread from a chloroform solution (concentration approximatly 0.1 mg/ml) onto the surface of 10.5 mL of HEPES/MES/citrate-buffered saline [5 mM HEPES, 5 mM MES, 20 mM sodium citrate, 25 mM sodium chloride, pH 7.4] contained in a polytetrafluoroethylene beaker. The surface area of the resultant POPG monolayer was approximately 5 cm$^2$. Surface tension was measured and adjusted to various desired values by withdrawing a glass capillary tube through the surface to remove a portion of the previously spread monolayer. When the desired value had been attained, 0.1 mL of a 1 mg/mL solution of the peptide dissolved in the above-mentioned buffer was injected beneath the surface with an hypodermic syringe, care being taken to minimize removal of the monolayer, and the surface tension monitored until no change was evident over approximatly 10 min observation time.

This procedure was repeated for a number of different initial lipid monolayer surface tensions, including determinations in the absence of lipid and with no peptide injection to determine the surface tension of the buffer alone. Data calculation involved subtraction of the latter value from all other measured values to provide defined "surface pressure" values. The change in surface pressure caused by injection of peptide was plotted against the initial surface pressure and critical insertion pressure determined by extrapolation to zero surface pressure change. These critical pressure values were used to compare the tendencies of the different peptides to interact with POPG monolayers and, by inference, naturally occuring membranes composed of similar lipids. The CSP peptides were found to have a critical pressure of 45±3 mN/M whereas the SSP peptides were found to have a much lower critical pressure of 30±3 mN/M.

The synthetic peptide SSP-3-5(A/E) (SEQ ID NO:112) was characterized by analytical ultracentrifugation using a Beckman Model E ultratracentrifuge and refractive index detection. The peptide was dissolved in a phosphate buffer [50 mn sodium phosphate, pH 7.0, 150 mM NaCl] at three concentrations: 0.4 mg/mL, 1.2 mg/mL, and 3.5 mg/mL. For each of these concentrations, runs were made at two rotational speeds (28,000 rpm and 40,000 rpm) and at two temperatures (4° C. and 20° C.). The results of all the experiments are best fit by two noninterconverting species in solution: a dimer and a tetramer. No monomers were detected. These findings support Applicants' assertion that these sequences may adopt stable dimeric structures (coiled-coils) in aqueous solution and in vivo under physiological conditions.

EXAMPLE 3

Generation of Antibodies Against Synthesized Peptides

Purified in vitro-synthesized peptides described in (Example 1) were dissolved in distilled water to 1 mg/mL. To denature the peptides 1.0 mL of this solution was mixed with 10 μL of 10% sodium dodecyl sulfate (SDS, BRL, Gaithersburg, Md.) and heated at 65° for 10 min. One mL of peptide solution (either the denatured or the native preparation) was mixed with 100 μL of 75 ug/mL keyhole limpet hemocyanin (Sigma), 30 μL of freshly opened 25% glutaraldehyde (Sigma) and 1.0 mL of phosphate buffered saline [PBS: 8.0 g NaCl/L, 0.2 g KCl/L, 1.44 g $Na_2HPO_4$/L, 0.24 g $KH_2PO_4$/L, pH 7.2]. The mixture was allowed to rock on a table top rocker for 3 h at room temperature. The mixture was sonicated for a few seconds to break up flocculent and was dialyzed (molecular weight cutoff: 10,000) overnight at 4° with two changes of 1 L of PBS. The preparation was sent to Hazelton laboratories in Denver, Pa. for injection into rabbits. Rabbit sera were collected on a biweekly basis. Sera containing antibodies produced after multiple injections with antigen were used to test specificity against in vitro and in vivo (Example 6) synthesized peptides.

Antibodies derived from this procedure were tested for specificity by reacting with in vitro-synthesized peptides which had been transferred to nitrocellulose membrane using a BRL dot blotting apparatus. The peptides were diluted in tris buffered saline [TBS: 25 mM TrisCl, pH 8.0, 8.0 g NaCl/L, 0.2 g KCl/L] to give solutions of 10 µg/µl, 1 µg/µL or 0.1 µg/µL. Two hundred microliters of each dilution were applied to the membrane using the dot blot apparatus following manufacturer's specifications. A dilution series of non-denatured (native) $SSP(5)_4$ (SEQ ID NO:2), $SSP(7)_4$ (SEQ ID NO:3), $SSP(8)_4$ (SEQ ID NO:4), $SSP(9)_4$ (SEQ ID NO:5), $SSP(10)_4$ (SEQ ID NO:6), or $SSP(11)_4$ (SEQ ID NO:7) peptides was loaded onto the nitrocellulose membrane in replicates, the membrane was then sectioned into strips and reacted with antibodies raised against denatured or native $SSP(5)_4$ or $SSP(7)_4$ peptides at a serum dilution of 1:500. Secondary goat anti-rabbit antibodies conjugated to alkaline phophatase (Bio-Rad, Richmond, Calif.) were used with 5-bromo-4-chloro-3-indolyl phosphate p-toluidine salt and nitro blue tetrazolium chloride to visualize the primary rabbit anti-peptide antibody reactions as described by the manufacturer. From these interactions it was determined that the antibodies prepared against native (coiled-coil) structures of peptides $SSP(5)_4$ (SEQ ID NO:2) or $SSP(7)_4$ (SEQ ID NO:3) cross-reacted with all the other native peptides and detected as little as 1 ug. The antibodies reacted with their own counterpart peptides to detect down to 0.01 µg of peptide. Cross reactivity to all other peptides was less when interacting with the antibodies raised against the denatured peptides $SSP(5)_4$ (SEQ ID NO:2) and $SSP(7)_4$ (SEQ ID NO:3 ).

One µg samples of peptides $SSP(5,7,8, 9, 10$ or $11)_4$ were denatured in loading buffer (4% SDS, 20% glycerol, 0.1M Tris pH 8.0, 4% β-mercaptoethanol, 0.01% bromphenol blue), boiled for 2 min and loaded onto a 12×10×0.075 cm 18% polyacrylamide SDS denaturing gel (acrylamide:bis-acrylamide=50:0.66) [Laemmli, U.K. (1970) Nature 227:680]. The samples were electrophoresed through the gel at 150 volts for 2.5 h. Western blots were performed as follows. The peptides were then transferred from the gels to 0.2 micron nitrocellulose membrane (Biorad) in a buffer which contained 2.4 g Tris base, 11.25 g glycine, 1 g SDS, 200 mL methanol/liter buffer using a Hoefer transblot apparatus at 30 volts for 30 rain followed by 80 volts for 30 min. The blots were air dried. Duplicate blots were then reacted with anti-denatured $SSP(5)_4$ antibody or anti-denatured $SSP(7)_4$ (SEQ ID NO:3) antibody at a serum dilution of 1:500. Visualization with secondary antibody conjugated to alkaline phosphatase, followed by 5-bromo-4-chloro-3-indolyl phosphate p-toluidine salt and nitro blue tetrazolium chloride showed detection of 1 µg of $SSP(5)_4$ peptide with anti $SSP(5)_4$ antibody and no cross reaction with 1 µg of $SSP(7,8\ 9,10,$or $11)_4$ peptides. One µg of $SSP(5)_4$ and $SSP(7)_4$ peptides could be visualized with anti-$SSP(7)_4$ antibody with no cross reaction with 1 µg of $SSP(8,9,10,11)_4$ peptides.

A fusion protein of glutathione-S-transferase and the SSP3-5 gene product was generated through the use of the Pharmacia™ pGEX GST Gene Fusion System (Current Protocols in Molecular Biology, Vol 2, pp 16.7.1–8, (1989) John Wiley and Sons). The fusion protein was purified by affinity chromatography on glutathione agarose (Sigma) or glutathione sepharose (Pharmacia) beads, concentrated using Centricon 10™ (Amicon) filters, and then subjected to SDS polyacrylamide electrophoresis (15% Acrylamide, 19:1 Acrylamide:Bis-acrylmide) for further purification. The gel was stained with Coomassie Blue for 30 min, destained in 50% Methanol, 10% Acetic Acid and the protein bands electroeluted using an Amicon™ Centiluter Microelectroeluter (Paul T. Matsudaira ed., A Practical Guide to Protein and Peptide Purification for Microsequencing, Academic Press, Inc. New York, 1989). A second gel prepared and run in the same manner was stained in a non acetic acid containing stain [9 parts 0.1% Coomassie Blue G250 (Bio-Rad) in 50% methanol and 1 part Serva Blue (Serva, Westbury, N.Y.) in distilled water] for 1–2 h. The gel was briefly destained in 20% methanol, 3% glycerol for 0.5–1 h until the GST-SSP3-5 band was just barely visible. This band was excised from the gel and sent with the electroeluted material to Hazelton Laboratories for use as an antigen in immunizing a New Zealand Rabbit. A total of 1 mg of antigen was used (0.8 mg in gel, 0.2 mg in solution). Test bleeds were provided by Hazelton Laboratories every three weeks. The approximate titer was tested by western blotting of *E. Coli* extracts from cells containing the SSP-3-5 gene under the control of the T7 promoter (Example 6) at different dilutions of protein and of serum. Known amounts of chemically synthesized protein corresponding to the SSP-3-5 (SEQ ID NO:91) sequence with only one amino acid change (SEQ ID NO:112) (see Example 1) were loaded on gels to test the limits of detection with the antibody in Western blotting protocols. Using the test bleed obtained 18 weeks after initial immunization Applicants could detect 2 ng of chemically synthesized peptide at a 1:4000 dilution of antibody and overnight incubation of the blot with the diluted serum. This serum was used to measure levels of SSP-3-5 (SEQ ID NO:91) expression in transgenic plants (Example 9) and to confirm the identity of radiolabelled SSP-3-5 protein (SEQ ID NO:91) in rice protoplasts (Example 10 ).

EXAMPLE 4

Construction of *E. coli* Expression Vector

To facilitate the construction and expression of the synthetic genes described below in Example 5, it was necessary to construct a plasmid vector with the following attributes:

1. No EarI restriction endonuclease sites such that insertion of sequences in Example 5 would produce a unique site.

2. Encoding tetracycline resistance to avoid loss of plasmid during growth and expression of toxic proteins.

3. Containing approximately 290 bp from plasmid pBT430 including the T7 promoter and terminator seqment for expression of inserted sequences in *E. coli*.

4. Containing unique EcoRI and NcoI restriction endonuclease recognition sites in proper location behind the T7 promoter to allow insertion of the oligonucleotide sequences in Example 5.

To obtain attributes 1 and 2 Applicants used plasmid pSK1 which was a spontaneous mutant of pBR322 where the ampicillin gene and the EarI site near that gene had been deleted (see FIG. 5). Plasmid pSK1 retained the tetracycline resistance gene, the unique EcoRI restriction sites at base 1 and a single EarI site at base 2353. To remove the EarI site at base 2353 of pSK1 a polymerase chain reaction (PCR) was performed using pSK1 as the template. Approximately 10 femtomoles of pSK1 were mixed with 1 μg each of oligonucleotides SM70 and SM71 which had been synthesized on an ABI1306B DNA synthesizer using the manufacturer's procedures.

| SM70 | 5'-CTGACTCGCTGCGCTCGGTC 3' | SEQ ID NO:9 |
|---|---|---|
| SM71 | 5'-TATTTTCTCCTTACGCATCTGTGC-3' | SEQ ID NO:10 |

The priming sites of these oligonucleotides on the pSK1 template are depicted in FIG. 5. The PCR was performed using a Perkin-Elmer Cetus kit (Emeryville, Calif.) according to the instructions of the vendor on a thermocycler manufactured by the same company. The 25 cycles were 1 min at 95°, 2 min at 42° and 12 min at 72°. The oligonucleotides were designed to prime replication of the entire pSK1 plasmid excluding a 30 b fragment around the EarI site (see FIG. 5). Ten microliters of the 100 μL reaction product were run on a 1% agarose gel and stained with ethidium bromide to reveal a band of about 3.0 kb corresponding to the predicted size of the replicated plasmid.

The remainder of the PCR reaction mix (90 μL) was mixed with 20 μL of 2.5 mM deoxynucleotide triphosphates (dATP, dTTP, dGTP, and dCTP), 30 units of Klenow enzyme added and the mixture incubated at 37° for 30 min followed by 65° for 10 min. The Klenow enzyme was used to fill in ragged ends generated by the PCR. The DNA was ethanol precipitated, washed with 70% ethanol, dried under vacuum and resuspended in water. The DNA was then treated with T4 DNA kinase in the presence of 1 mM ATP in kinase buffer. This mixture was incubated for 30 mins at 37° followed by 10 min at 65°. To 10 μL of the kinased preparation, 2 μL of 5× ligation buffer and 10 units of T4 DNA ligase were added. The ligation was carried out at 15° for 16 h. Following ligation, the DNA was divided in half and one half digested with EarI enzyme. The Klenow, kinase, ligation and restriction endonuclease reactions were performed as described in Sambrook et al., [Molecular Cloning, A Laboratory Manual, 2nd ed. (1989) Cold Spring Harbor Laboratory Press]. Klenow, kinase, ligase and most restriction endonucleases were purchased from BRL. Some restriction endonucleases were purchased from NEN Biolabs (Beverly, Mass.) or Boehringer Mannheim (Indianapolis, Ind.). Both the ligated DNA samples were transformed separately into competent JM103 [supE thi del (lac-proAB) F' [traD36 porAB, lacIq lacZ del M15] restriction minus] cells using the CaCl₂ method as described in Sambrook et al., [Molecular Cloning, A Laboratory Manual, 2nd ed. (1989) Cold Spring Harbor Laboratory Press] and plated onto media containing 12.5 ug/mL tetracycline. With or without EarI digestion the same number of transformants were recovered suggesting that the EarI site had been removed from these constructs. Clones were screened by preparing DNA by the alkaline lysis miniprep procedure as described in Sambrook et al., [Molecular Cloning, A Laboratory Manual, 2nd ed. (1989) Cold Spring Harbor Laboratory Press] followed by restriction endonuclease digest analysis. A single clone was chosen which was tetracycline-resistant and did not contain any EarI sites. This vector was designated pSK2. The remaining EcoRI site of pSK2 was destroyed by digesting the plasmid with EcoRI to completion, filling in the ends with Klenow and ligating. A clone which did not contain an EcoRI site was designated pSK3.

To obtain attributes 3 and 4 above, the bacteriophage T7 RNA polymerase promoter/terminator segment from plasmid pBT430 was amplified by PCR. Plasmid pBT430 is a derivative of pET-3a [Rosenberg et al., (1987) Gene 56:125–135]. The T7 promoter/terminator sequence was cloned into the BamHI site of pBR322 to make plasmid pET-3a. Plasmid pBT430 was constructed by converting the NdeI site at the ATG translation initiation of plasmid pET-3a to an NcoI site using oligonucleotide directed mutagenesis. The DNA sequence of pET-3a in this region, 5'CATATGG, was changed to 5'-CCCATGG in pBT430. Oligonucleotide primers SM78 (SEQ ID NO:11) and SM79 (SEQ ID NO:12) were designed to prime a 300 b fragment from pBT430 spanning the T7 promoter/terminator sequences (see FIG. 5).

| SM78 | 5'-TTCATCGATAGGCGACCACACCCGTCC-3' | SEQ ID NO:11 |
|---|---|---|
| SM79 | 5'-AATATCGATGCCACGATGCGTCCGGCG-3' | SEQ ID NO:12 |

The PCR reaction was carried out as described previously using pBT430 as the template and a 300 bp fragment was generated. The ends of the fragment were filled in using Klenow enzyme and kinased as described above. DNA from plasmid pSK3 was digested to completion with PvuII enzyme and then treated with calf intestinal alkaline phophatase (Boehringer Mannheim) to remove the 5' phosphate. The procedure was as described in Sambrook et al., [Molecular Cloning, A Laboratory Manual, 2nd ed, (1989) Cold Spring Harbor Laboratory Press]. The cut and phosphatased pSK3 DNA was purified by ethanol precipitation and a portion used in a ligation reaction with the PCR generated fragment containing the T7 promoter sequence. The ligation mix was transformed into JM103 [supE thi del (lac-proAB) F' [traD36 porAB, lacIq lacZ del M15] restriction minus] and tetracycline-resistant colonies were screened. Plasmid DNA was prepared via the alkaline lysis mini prep method and restriction endonuclease analysis was performed to detect insertion and orientation of the PCR product. Two clones were chosen for sequence analysis: Plasmid pSK5 had the fragment in the orientation shown in FIG. 5. Sequence analysis performed on alkaline denatured double-stranded DNA using Sequenase® T7 DNA polymerase (US Biochemical Corp) and manufacturer's suggested protocol revealed that pSK5 had no PCR replication errors within the T7 promoter/terminator sequence.

EXAMPLE 5

Construction of Synthetic Genes in Expression Vector DSK5

I.

(a) The strategy for the construction of repeated synthetic gene sequences based on the EarI site is depicted in FIG. 6. The first step was the insertion of an oligonucleotide sequence encoding a base gene of amino acids. This oligonucleotide insert contained a unique EarI restriction site for subsequent insertion of oligonucleotides encoding one or more heptad repeats and added an unique Asp718 restriction site for use in transfer of gene sequences to plant vectors. The overhanging ends of the oligonucleotide set allowed insertion into the unique NcoI and EcoRI sites of vector pSK5.

```
            M  E  E  K  M  K  A  M  E  E  K
SM81   5'-CATGGAGGAGAAGATGAAGGCGATGGAAGAGAAG
SM80       3'-CTCCTCTTCTACTTCCGCTACCTTCTCTTC
            NCOI                      EARI

M  K  A
SM81   ATGAAGGCGTGATAGGTACCG-3'              (SEQ ID NO:111)
SM80   TACTTCCGCACTATCCATGGCTTAA-5'          (SEQ ID NO:13)
                       ASP718 ECORI           (SEQ ID NO:14)
```

Figure 7:
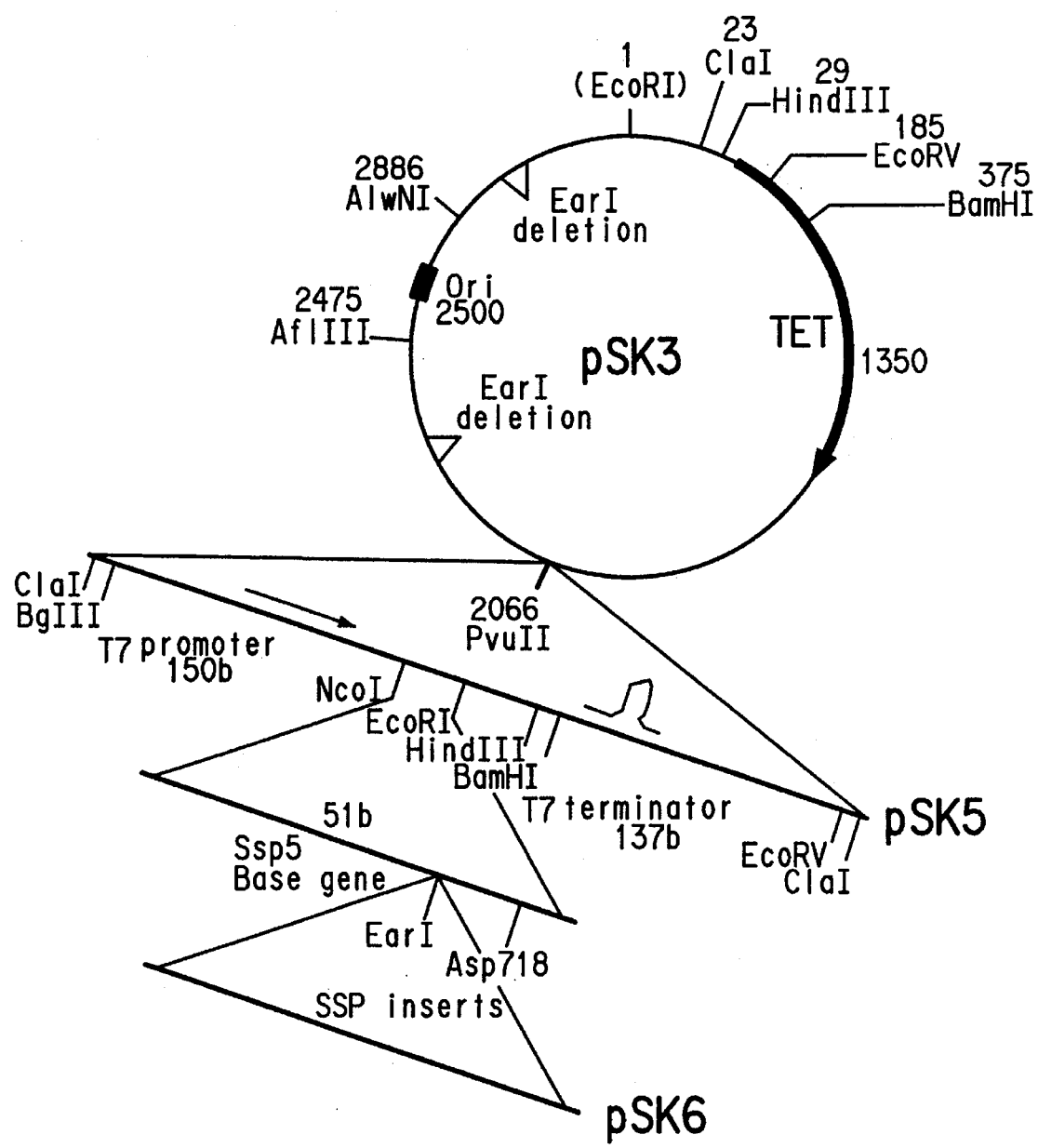
FIG. 7 shows the insertion of the base gene oligonucleotides into the NcoI/EcoRI sites of pSK5 to create the plasmid pSK6. This base gene sequence was used as in FIG. 6 to insert the various SSP coding regions at the unique EarI site to create the cloned seqments listed.

DNA from plasmid pSK5 was digested to completion with NcoI and EcoRI restriction endonucleases and purified by agarose gel electrophoresis. Purified DNA (0.1 ug) was mixed with 1 µg of each oligonucleotide SM80 (SEQ ID NO:14) and SM81 (SEQ ID NO:13) and ligated. The ligation mixture was transformed into E. coli strain JM103 [supE thi del (lac-proAB) F' [traD36 porAB, lacIq lacZ del M15] restriction minus] and tetracycline resistant transformants screened by rapid plasmid DNA preps followed by restriction digest analysis. A clone was chosen which had one each of EarI, NcoI, Asp718 and EcoRI sites indicating proper insertion of the oligonucleotides. This clone was designated pSK6 (FIG. 7). Sequencing of the region of DNA following the T7 promoter confirmed insertion of oligonucleotides of the expected sequence.

(b) Repetitive heptad coding sequences were added to the base gene construct of (a) above by generating oligonucleotide pairs which could be directly ligated into the unique EarI site of the base gene. Oligonucleotides SM84 (SEQ ID NO:15) and SM85 (SEQ ID NO:16) code for repeats of the SSP5 heptad. Oligonucleotides SM82 (SEQ ID NO:17) and SM83 (SEQ ID NO:18) code for repeats of the SSP7 heptad.

```
SSP5           M  E  E  K  M  K  A
SM84   5'-GATGGAGGAGAAGATGAAGGC-3'       (SEQ ID NO:62)
SM85   3'-    CCTCCTCTTCTACTTCCGCTA-5'    (SEQ ID NO:15)
                                          (SEQ ID NO:16)

SSP7           M  E  E  K  L  K  A
SM82   5'-GATGGAGGAGAAGCTGAAGGC-3'       (SEQ ID NO:61)
SM83   3'-    CCTCCTCTTCGACTTCCGCTA-5'    (SEQ ID NO:17)
                                          (SEQ ID NO:18)
```

Oligonucleotide sets were ligated and purified to obtain DNA fragments encoding multiple heptad repeats for insertion into the expression vector. Oligonucleotides from each set totalling about 2 µg were kinased, and ligated for 2 h at room temperature. The ligated multimers of the oligonucleotide sets were separated on an 18% non-denaturing 20×20× 0.015 cm polyacrylamide gel (Acrylamide: bis-acrylamide= 19:1). Multimeric forms which separated on the gel as 168 bp (8 n) or larger were purified by cutting a small piece of polyacrylamide containing the band into fine pieces, adding 1.0 mL of 0.5M ammonium acetate, 1 mM EDTA (pH 7.5) and rotating the tube at 37° overnight. The polyacrylamide was spun down by centrifugation, 1 µg of tRNA was added to the supernatant, the DNA fragments were precipitated with 2 volumes of ethanol at −70°, washed with 70% ethanol, dried, and resuspended in 10 µL of water.

Ten micrograms of pSK6 DNA were digested to completion with EarI enzyme and treated with calf intestinal alkaline phosphatase. The cut and phosphatased vector DNA was isolated following electrophoresis in a low melting point agarose gel by cutting out the banded DNA, liquifying the agarose at 55°, and purifying over NACS PREPAC™ columns (BRL) following manufacturer's suggested procedures. Approximately 0.1 µg of purified EarI digested and phosphatase treated pSK6 DNA was mixed with 5 µL of the gel purified multimeric oligonucleotide sets and ligated. The ligated mixture was transformed into E. coli strain JM103 [supE thi del (lac-proAB) F' [traD36 porAB, lacIq lacZ del M15] restriction minus] and tetracycline-resistant colonies selected. Clones were screened by restriction digests of rapid plasmid prep DNA to determine the length of the inserted DNA. Restriction endonuclease analyses were usually carried out by digesting the plasmid DNAs with Asp718 and BglII, followed by separation of fragments on 18% non-denaturing polyacrylamide gels. Visualization of fragments with ethidium bromide, showed that a 150 bp fragment was generated when only the base gene segment was present. Inserts of the oligonucleotide fragments increased this size by multiples of 21 bases. From this screening several clones were chosen for DNA sequence analysis and expression of coded sequences in E. coli (see Example 6).

TABLE 9

| Clone # | SEQ ID NO: | Amino Acid Repeat (SSP)[1] | SEQ ID NO: |
|---|---|---|---|
| C15 | 32 | 5.<u>7.7.7.7.7</u>.5 | 33 |
| C20 | 34 | 5.<u>7.7.7.7.7</u>.5 | 35 |
| C30 | 36 | 5.<u>7.7.7.7</u>.5 | 37 |
| D16 | 38 | 5.<u>5.5</u>.5 | 39 |
| D20 | 40 | 5.<u>5.5.5.5</u>.5 | 41 |
| D33 | 42 | 5.<u>5.5.5</u>.5 | 43 |

Sequence by Heptad

[1]Refer to Table 3

The first and last SSP5 heptads flanking the sequence of each construct are from the base gene of section (a) above. Inserts are designated by underlining.

(c) Because the gel purification of the oligomeric forms of the oligonucleotides did not give the expected enrichment of longer (i.e., >8 n) inserts, Applicants used a different procedure for a subsequent round of insertion constructions. For this series of constructs four more sets of oligonucleotides were generated which code for SSP 8,9,10 and 11 amino acid sequences respectively:

| | | |
|---|---|---|
| SSP8 | M E E K L K K | (SEQ ID NO:64) |
| SM86 | 5'-GATGGAGGAGAAGCTGAAGAA-3' | (SEQ ID NO:19) |
| SM87 | 3'-   CCTCCTCTTCGACTTCTTCTA-5' | (SEQ ID NO:20) |
| | | |
| SSP9 | M E E K L K W | (SEQ ID NO:67) |
| SM88 | 5'-GATGGAGGAGAAGCTGAAGTG-3' | (SEQ ID NO:21) |
| SM89 | 3'-   CCTCCTCTTCGACTTCACCTA-5' | (SEQ ID NO:22) |
| | | |
| SSP10 | M E E K M K K | (SEQ ID NO:65) |
| SM90 | 5'-GATGGAGGAGAAGATGAAGAA-3' | (SEQ ID NO:23) |
| SM91 | 3'-   CCTCCTCTTCTACTTCTTCTA-5' | (SEQ ID NO:24) |
| | | |
| SSP11 | M E E K M K W | (SEQ ID NO:68) |
| SM92 | 5'-GATGGAGGAGAAGATGAAGTG-3' | (SEQ ID NO:25) |
| SM93 | 3'-   CCTCCTCTTCTACTTCACCTA-5' | (SEQ ID NO:26) |

The following HPLC procedure was used to purify multimeric forms of the oligonucleotide sets after kinasing and ligating the oligonucleotides as described in section (b) above. Chromatography was performed on a Hewlett Packard Liquid Chromatograph instrument, Model 1090M. Effluent absorbance was monitored at 2 nm. Ligated oligonucleotides were centrifuged at 12,000×g for 5 min and injected onto a 2.5µ TSK DEAE-NPR ion exchange column (35 cm×4.6 mm I.D.) fitted with a 0.5µ in-line filter (Supelco). The oligonucleotides were separated on the basis of length using a gradient elution and a two buffer mobile phase Buffer A: 25 mM Tris-Cl, pH 9.0, and Buffer B: Buffer A+1M NaCl]. Both Buffers A and B were passed through 0.2µ filters before use. The following gradient program was used with a flow rate of 1 mL per min at 30°:

| Time | % A | % B |
|---|---|---|
| initial | 75 | 25 |
| 0.5 min | 55 | 45 |
| 5 min | 50 | 50 |
| 20 min | 38 | 62 |
| 23 min | 0 | 100 |
| 30 min | 0 | 100 |
| 31 min | 75 | 25 |

Fractions (500 µL) were collected between 3 min and 9 min. Fractions corresponding to lengths between 120 bp and 2000 bp were pooled as determined from control separations of restriction digests of plasmid DNAs.

The 4.5 mL of pooled fractions for each oligonucleotide set were precipitated by adding 10 µg of tRNA and 9.0 mL of ethanol, rinsed twice with 70% ethanol and resuspended in 50 µL of water. Ten microliters of the resuspended HPLC purified oligonucleotides were added to 0.1 µg of the EarI cut, phosphatased pSK6 DNA described above and ligated overnight at 15°. All six oligonucleotide sets described above which had been kinased and self-ligated but not purified by gel or HPLC were also used in separate ligation reactions with the pSK6 vector. The ligation mixtures were transformed into E. coli strain DH5α [supE44 del lacU169 (phi 80 lacZ del M15) hsdR17 recA1 endA1 gyr196 thi1 relA1] tetracycline-resistant colonies selected. Applicants chose to use the DH5α [supE44 del lacU169 (phi 80 lacZ del M15) hsdR17 recA1 endA1 gyr196 thi1 relA1] strain for all subsequent work because this strain has a very high transformation rate and is recA-. The recA- phenotype eliminates concerns that these repetitive DNA structures may be substrates for homologous recombination leading to deletion of multimeric sequences.

Clones were screened as described in (b) above. Several clones were chosen to represent insertions of each of the six oligonucleotide sets.

TABLE 10

| | Sequence by Heptad | | |
|---|---|---|---|
| Clone # | SEQ ID NO: | Amino Acid Repeat (SSP)[1] | SEQ ID NO: |
| 82–4 | 44 | 7.7.7.7.7.7.5 | 45 |
| 84–H3 | 46 | 5.5.5.5 | 47 |
| 86–H23 | 48 | 5.8.8.5 | 49 |
| 88–2 | 50 | 5.9.9.9.5 | 51 |
| 90–H8 | 52 | 5.10.10.10.5 | 53 |
| 92–2 | 54 | 5.11.11.5 | 55 |

[1]Refer to Table 3

The first and last SSP5 heptads flanking the sequence represent the base gene sequence. Insert sequences are underlined. Clone numbers including the letter "H" designate HPLC-purified oligonucleotides. The loss of the first base gene repeat in clone 82-4 may have resulted from homologous recombination between the base gene repeats 5.5 before the vector pSK6 was transferred to the recA- strain. The HPLC procedure did not enhance insertion of longer multimeric forms of the oligonucleotide sets into the base gene but did serve as an efficient purification of the ligated oligonucleotides.

(d) Oligonucleotides were designed which coded for mixtures of the SSP sequences and which varied codon usage as much as possible. This was done to reduce the possibility of deletion of repetitive inserts by recombination once the synthetic genes were transformed into plants and to extend the length of the constructed gene segments. These oligonucleotides encode four repeats of heptad coding units (28 amino acid residues) and can be inserted at the unique EarI site in any of the previously constructed clones. SM96 and SM97 code for SSP(5)4 (SEQ ID NO:2), SM98 and SM99 code for SSP(7)₄ (SEQ ID NO:3) and SM100 plus SM101 code for SSP8.9.8.9 (SEQ ID NO:83).

| | | M E E K M K A M E E K M K |
|---|---|---|
| SM96 | | 5'-GATGGAGGAAAAGATGAAGGCGATGGAGGAGAAAATGAAA |
| SM97 | 3' | CCTCC TTT TCT ACTTCC GCT ACCTCC TCT TTT ACTTT |

-continued

```
            A  M  E  E  K  M  K  A  M  E  E  K  M  K  A           (SEQ ID NO:2)
            GCTATGGAGGAAAAGATGAAAGCGATGGAGGAGAAATGAAGGC-3'          (SEQ ID NO:88)
            CGATACCT CCT TTT CTACTT TCG CTACCT CCT CTT TTA CTT CCGCTA-5'  (SEQ ID NO:89)

M  E  E  K  L  K  A  M  E  E  K  L  K
SM98  5'-GATGGAGGAAAAGCTGAAAGCGATGGAGGAGAAACTCAAG
SM99  3'     CCTCC TTT TCG ACTTTC GCT ACCTCC TCT TTG AGTTC

A  M  E  E  K  L  K  A  M  E  E  K  L  K  A           (SEQ ID NO:3)
            GCTATGGAAGAAAAGCTTAAAGCGATGGAGGAGAAACTGAAAGC-3'        (SEQ ID NO:27)
            CGATACCTTC TTT TCG AATTTC GCATCCTCC TCT TTG ACTTCC GCTA-5'  (SEQ ID NO:28)

M  E  E  K  L  K  K  M  E  E  K  L  K
SM100  5'-GATGG AGGAAAAGCTTAAGAAGATGGAAGAAAAGCTGAAA
SM101  3'     CC TCC TTT TCG AATTCT TCT ACCTTC TTT TCG ACTTT

M  E  E  K  L  K  K  M  E  E  K  L  K  W              (SEQ ID NO:83)
           TGGATGGAGGAGAAACTCAAAAAGATGGAGGAAAAGCTTAAATG-3'        (SEQ ID NO:29)
           ACCT ACCTCC TCT TTG AGTTTT TCA TCCTCC TTT TCG AATTTA CCTA-5'  (SEQ ID NO:30)
```

DNA from clones 82-4 and 84-H3 (see c above) were digested to completion with EarI enzyme, treated with phosphatase and gel purified. About 0.2 μg of this DNA were mixed with 1.0 μg of each of the oligonucleotide sets SM96 and SM97, SM98 and SM99 or SM100 and SM101 which had been previously kinased. The DNA and oligonucleotides were ligated overnight and then the ligation mixes transformed into *E. coli* strain DH5α. Tetracycline-resistant colonies were screened as described in sections (b) and (c) for the presence of the oligonucleotide inserts, Clones were chosen for sequence analysis based on their restriction endonuclease digestion patterns,

TABLE 10

| | Sequence by Heptad | | |
|---|---|---|---|
| Clone # | SEQ ID NO: | Amino Acid Repeat (SSP)[1] | SEQ ID NO: |
| 2-9 | 56 | 7.7.7.7.7.7.<u>8.9.8.9</u>.5 | 57 |
| 3-5 | 90 | 7.7.7.7.7.7.<u>5.5</u> | 91 |
| 5-1 | 58 | 5.5.5.<u>7.7.7.7</u>.5 | 59 |

[1]Refer to Table 3
Inserted oligonucleotide segments are underlined

Clone 2-9 was derived from oligonucleotides SM100 (SEQ ID NO:29) and SM101 (SEQ ID NO:30) ligated into the EarI site of clone 82-4 (see section (c) above), Clone 3-5 (SEQ ID NO:90) was derived from the insertion of the first 22 bases of the oligonucleotide set SM96 (SEQ ID NO:88) and SM97 (SEQ ID NO:89) into the EarI site of clone 82-4 (SEQ ID NO:44). This partial insertion may reflect improper annealing of these highly repetitive oligos. Clone 5-1 (SEQ ID NO:58) was derived from oligonucleotides SM98 (SEQ ID NO:27) and SM99 (SEQ ID NO:28) ligated into the EarI site of clone 84-H3 (SEQ ID NO:46) (see section (c) above).

II.

(a) A second strategy for construction of synthetic gene sequences was implemented to allow more flexibility in both DNA and amino acid sequence. This strategy is depicted in FIGS. 8 and 9. The first step was the insertion Of an oligonucleotide sequence encoding a base gene of 16 amino acids into the original vector pSK5. This oligonucleotide insert contained an unique EarI site as in the previous base gene construct for use in subsequent insertion of oligonucleotides encoding one or more heptad repeats. The base gene also included a BspHI site at the 3' terminus. The overhanging ends of this cleavage site are designed to allow "in frame" protein fusions using NcoI overhanging ends. Therefore, gene segments can be multiplied using the duplication scheme described in FIG. 9. The overhanging ends of the oligonucleotide set allowed insertion into the unique NcoI and EcoRI sites of vector pSK5.

```
              M  E  E  K  M  K  K  L  E  E  K
SM107  5'-CATGGAGGAGAAGATGAAAAAGCTCGAAGAGAAG
SM106        3'-CTCCTCTTCTACTTTTTCGAGCTTCTCTTC
          NCOI                                EARI

M  K  V  M  K                                (SEQ ID NO:113)
           ATGAAGGTCATGAAGTGATAGGTACCG-3'               (SEQ ID NO:92)
           TACTTCCAGTACTTCACTATCCATGGCTTAA-5'           (SEQ ID NO:93)
              BSPHI    ASP718
```

The oligonucleotide set was inserted into pSK5 vector as described in I (a) above. The resultant plasmid was designated pSK34.

(b) Oligonucleotide sets encoding 35 amino acid "segments" were ligated into the unique EarI site of the pSK34 base gene using procedures as described in I (b) In this case, the oligonucleotides were not gel or HPLC purified but simply annealed and used in the ligation reactions. The following oligonucleotide sets were used:

```
SEG 3       L    E    E    K    M    K    A    M    E    D    K    M    K    W
SM110   5'-GCTGGAAGAAAAGATGAAGGCTATGGAGGACAAGATGAAATGG
SM111       3'-   CCTT CTT TTC TACTTC CGATACCTC CTGTTC TACTTT ACC
```

```
                    L   E   E   K   M   K   K           (SEQ ID NO:85)
                                                        (amino acids 8-28)
                        CTTGAGGAAAAGATGAAGAA-3'          (SEQ ID NO:94)
                        GAACTC CTT TTC TACTTC TTCGA-5'   (SEQ ID NO:95)
```

```
SEG 4       L    E    E    K    M    K    A    M    E    D    K    M    K    W
SM112   5'-GCTCGAAGAAAGATGAAGGCAATGGAAGACAAAATGAAGTGG
SM113       3'-  GCTT CTT TCT ACTTCC GTT ACCTTC TGT TTT ACTTCACC
```

```
                    L   E   E   K   M   K   K           (SEQ ID NO:97)
                                                        (amino acids 8-28)
                        CTTGAGGAGAAAATGAAGAA-3'          (SEQ ID NO:98)
                        GAACTC CTC TTT TACTTC TTCGA-5'   (SEQ ID NO:99)
```

```
SEG 5       L    K    E    E    M    A    K    M    K    D    E    M    W    K
SM114   5'-GCTCAAGGAGGAAATGGCTAAGATGAAAGACGAAATCTGGAAA
SM115       3'-  GTTC CTC CTT TACCGATTC TACTTT CTGCTT TACACCTTT
```

```
                    L   K   E   E   M   K   K           (SEQ ID NO:101)
                                                        (amino acids 8-28)
                        CTGAAAGAGGAAATGAAGAA            (SEQ ID NO:102)
                        GACTTT CTC CTT TACTTC TTCGA     (SEQ ID NO:103)
```

Clones were screened for the presence of the inserted segments by restriction digestion followed by separation of fragments on 6% acrylamide gels. Correct insertion of oligonucleotides was confirmed by DNA sequence analyses. Clones containing segments 3,4 and 5 respectively were designated pSKseg3, pSKseg4, and pSKseg5.

These "segment" clones were used in a duplication scheme-as described in FIG. 9. Ten ug of plasmid pSKseg3 were digested to completion with NheI and BspHI and the 1503 bp fragment isolated from an agarose gel using the Whatmann paper technique (see Example 7). Ten ug of plasmid pSKseg4 were digested to completion with NheI and NcoI and the 2109 bp band gel isolated. Equal amounts of these fragments were ligated and recombinants selected on tetracycline. Clones were screened by restriction digestions and their sequences confirmed. The resultant plasmid was designated pSKseg34.

pSKseg34 and pSKseg5 plasmid DNAs were digested, fragments isolated and ligated in a similar manner as above to create a plasmid containing DNA sequences encoding segment 5 fused to segments 3 and 4. This construct was designated pSKseg534 and encodes the following amino acid sequence:

```
SSP534  NH2-MEEKMKKLKEEMAKMKDEMWKLKEEMKKLEEKMKVMEEKMKKLEEKMKA
            MEDKMKWLEEKMKKLEEKMKVMEEKMKKLEEKMKAMEDKMKWLEEKMKK
            LEEKMKVMK-COOH     (SEQ ID NO:105)
```

EXAMPLE 6

Expression of Proteins from Synthetic Gene Sequences in E. coli

To detect expression of the polypeptides encoded by the synthetic genes described in Example 5, the plasmid DNAs were maintained in DH5α [supE44 del lacU169 (phi 80 lacZ del M15) hsdR17 recA1 endA1 gyr196 thi1 relA1] cells or transformed into E. coli strain HMS174 [recA hsdR rifR] or BL21 (DE3) [hsdS gal (lambda cIts857 indi Sam7 nin5 lac UV5-T7 gene1]. In DH5α [supE44 del lacU169 (phi 80 lacZ del M15) hsdR17 recA1 endA1 gyr196 thi1 relA1] or HMS174 [recA hsdR rifR] cells, the expression of proteins by addition of T7 polymerase was achieved by infection of the late log phase cells with lambda phage CE6 at a multiplicity of infection of 0.3. In BL21(DE3) [hsdS gal (lambda cIts857 indi Sam7 nin5 lac UV5-T7 gene1 ] cells, the T7 polymerase gene product was expressed by derepression of the lacZ promoter with addition of isopropylthiogalactoside (IPTG) (BRL). Both procedures were performed as described by Studier et al., [(1986) J. Mol. Biol. 189:113–130].

One to three h after induction, samples of the induced cells were collected and concentrated 10-fold by centrifugation and resuspended in lysis buffer [100 mM NaCl, 50 mM Tris pH 8.0, 1 mM EDTA]. Samples (10 μL) of the concentrated cells were lysed by boiling in an equal volume of SDS dye buffer for several min then loaded onto an 18% polyacrylamide SDS denaturing gel as described in Example 3. Alternatively, 100 μL samples were removed from induced cultures, washed twice with M9 minimal media [Sambrook et al , Molecular Cloning, A Laboratory Manual, 2nd ed. (1989) Cold Spring Harbor Laboratory Press], resuspended in M9 minimal medium and labelled with $^{35}$S methionine. The labelling procedure was performed as described by Studier et al., [(1986) J. Mol Biol. 189:113–130]. Since these polypeptides have a high percentage of methionine, it was expected that they would label better than any other proteins in the E. coli cells. After 10 min the labelled cells were concentrated 10-fold by centrifugation. The concentrated cells were lysed as with the unlabelled samples and loaded onto SDS-PAGE gels.

The gels were fixed and stained in 50% trichloroacetic acid, 10% acetic acid, 0.1% Coomassie Blue for 30 min, then destained in 50% methanol, 10% acetic acid for 30 min followed by overnight destaining in 5% methanol, 7% acetic acid. The fixed and destained gels were vacuum-dried and the gels containing labelled proteins were placed in film cassettes with X-ray film for overnight exposure.

With Coomassie staining, the polypeptide gene products were visible for most of the smaller (<8 n) gene constructs. There were no E. coli proteins with molecular weight of less than 7,000 daltons visible on the gels. This facilitated visualization of these <6,000 dalton polypeptide gene products. They represented up to an estimated 40 mg/L of original induced cell culture. Induced polypeptides were also seen as intensely labelled bands on the autoradiographs of the $^{35}$S methionine labelled samples. The SSP polypeptides tend to run somewhat faster than predicted by globular size standards in this gel system. The size of each of the overexpressed polypeptide bands was proportional to the specific gene sequences determined in Example 5.

TABLE 12

| Clone # | SEQ ID NO: | Polypeptide Size in Kilodaltons (by Calculation) | SEQ ID NO: |
| --- | --- | --- | --- |
| D16 | 38 | 3.464 | 39 |
| 82–4 | 44 | 5.594 | 45 |
| 84–H3 | 46 | 3.464 | 47 |
| 86–H23 | 48 | 3.542 | 49 |
| 88–2 | 50 | 4.622 | 51 |
| 90–H8 | 52 | 4.502 | 53 |
| 92–2 | 54 | 3.695 | 55 |
| 2–9 | 56 | 9.691 | 57 |
| 3–5 | 90 | 6.820 | 91 |
| 5–1 | 58 | 6.856 | 59 |
| seg 3 | 84 | 4.466 | 85 |
| seg 4 | 96 | 4.466 | 97 |
| seg 5 | 100 | 4.466 | 101 |
| *seg 34 | 86 | 8.932 | 87 |
| *seg 534 | 104 | 13.398 | 105 |

*These proteins have not been tested for expression in E. Coli.

The identity of some of the overproduced polypeptides was confirmed by Western blotting and reaction with anti-SSP antibodies as described in Example 3. More sensitive detection was made possible by the use of secondary antibodies conjugated to horseradish peroxidase and chemiluminescent visualization. This procedure was performed according to the manufacturer's directions (Amersham). Although the anti-SSP(5)$_4$ and anti-SSP(7)$_4$ antibodies interact with other E. coli proteins (~7000–8,000 daltons), they could be used to detect the smaller molecular weight-induced polypeptide products. Anti-SSP(5)$_4$ reacted with polypeptides from genes containing mostly SSP5 repeats such as 84-3 (SEQ ID NO:47) and 5-1 (SEQ ID NO:59) but not polypeptides from genes containing only SSP7 repeated sequences such as 82-4 (SEQ ID NO:45) and 3-5 (SEQ ID NO:91). Anti-SSP(7)$_4$ reacted with polypeptide from clones 82-4 (SEQ ID NO:45) and 3-5 (SEQ ID NO:91) (mostly SSP7 repeats) but less well with polypeptide from Clone 5-1 (SEQ ID NO:59) where the SSP7 repeats are contained within SSP5 repeats.

The anti GST SSP-3-5 antibody described in Example 3 was used to detect the SSP-3-5 protein (SEQ ID NO:91) in bacterial induction samples. Applicants detected protein in induction samples diluted to 1:100 (approximately 20 ng of protein). The specificity of this antibody was tested against induction samples of all other synthetic proteins (see Table 5). It had limited cross reactivity with proteins from clones 86-H23 (SEQ ID NO:49) and 88-2 (SEQ ID NO:51), more reactivity with proteins from clones D16 (SEQ ID NO:39) and 84-H3 (SEQ ID NO:47) and strong reactivity with protein from clone 82-4 (SEQ ID NO:45) (precursor to clone 3-5 (SEQ ID NO:91)).

EXAMPLE 7

Construction of Chimeric Genes for Expression of Synthetic Gene Products in Plants To express the synthetic gene products described in Example 6 in plant leaf cells, the sequences were transferred from the E. coli expression vector pSK6 or pSK34 to plasmid pMH40 (see FIG. 10). Plasmid pMH40 contains the 35S 5' promoter sequences from cauliflower mosaic virus, the 5' translation leader sequence from the chlorophyll a/b binding protein gene, the coding region for the b-glucuronidase (GUS) gene, and the NOS 3' non-coding sequences. This plasmid has been designed with a unique NcoI restriction site at the ATG translation initiation codon and an unique Asp718 site Just 3' to the translation stop codon.

To replace the GUS gene coding sequence with the synthetic storage protein gene sequences, 10 μg of pMH40 DNA were digested to completion with Asp718 and NcoI restriction endonucleases. The digestion products were separated on a 1.0% agarose gel by overnight electrophoresis at 15 volts. The 5,080 bp vector fragment containing the 35S promoter and NOS 3' sequences was separated from the smaller fragment containing the GUS coding region. The 5,080 bp fragment was collected by cutting the agarose in front of the band, inserting a 10×5 mm piece of Whatman 3 MM paper into the agarose and electrophoresing the fragment into the paper [Errington, (1990) Nucleic Acids Research, 18:17]. The fragment and buffer were spun out of the paper by centrifugation and the DNA in the ~100 μL was precipitated by adding 10 mg of tRNA, 10 μL of 3M sodium acetate and 200 μL of ethanol. The precipitated DNA was washed twice with 70% ethanol and dried under vacuum. The fragment DNA was resuspended in 20 μL of water and a portion diluted 10-fold for use in ligation reactions.

Plasmid DNA (10 mg) from each of the clones 82-4, 84-H3, 86-H23, 88-2, and 90-H8, 3-5 and pSK534 was digested to completion with Asp718 and NcoI restriction endonucleases. The digestion products were separated on an 18% polyacrylamide non-denaturing gel as described in Example 5. Gel slices containing the desired fragments were cut from the gel and purified by inserting the gel slices into a 1% agarose gel and electrophoresing for 20 min at 100 volts. DNA fragments were collected on 10×5 mm pieces of Whatman 3 MM paper, the buffer and fragments spun out by centrifugation and the DNA precipitated with ethanol. The fragments were resuspended in 6 μL water. One microliter of the diluted pMH40 fragment described above, 2 μL of 5× ligation buffer and 1 μL of T4 DNA ligase were added. The mixture was ligated overnight at 15°.

The ligation mixes were transformed into E. coli strain DH5α [supE44 del lacU169 (phi 80 lacZ del M15) hsdR17 recA1 endA1 gyr196 thi$_1$ relA1] and ampicillin-resistant colonies selected. The clones were screened by restriction endonuclease digestion analyses of rapid plasmid DNAs and by DNA sequencing. DNA (from clones containing synthetic gene sequences inserted between the 35S promoter and the NOS 3' sequences were digested with SalI endonuclease to completion. The 35S promoter::synthetic gene::NOS 3' sequences were contained on a ~2100 b SalI fragment. This fragment was isolated from a 1% agarose gel on Whatman 3 MM paper as Example 7.

To express the SSP's to high levels in seeds, the same coding regions were transferred by similar procedures as described above to the seed promoter vectors CW108, CW109 or ML113 (FIG. 11). The vectors CW108 and ML113 contain the bean phaseolin promoter (from base +1 to base −494),and 1191 bases of the 3' sequences from bean phaseolin gene. CW109 contains the soybean β-conglycinin promoter (from base +1 to base −619) and the same 1191 bases of 3' sequences from the bean phaseolin gene. These vectors were designed to allow direct cloning of coding sequences into unique NcoI and Asp718 sites. These vectors also provide sites (HindIII or SalI) at the 5' and 3' ends to allow transfer of the promoter/coding region/3' sequences directly to appropriate binary vectors.

EXAMPLE 8

Transformation of Tobacco with the SSP Chimeric Genes

The binary vectors pZS97 or pZS97K were used to transfer the chimeric genes to plants. Both binary vectors pZS97 and pZS97K (FIG. 12) are part of a binary Ti plasmid vector system [Bevan, (1984) Nucl. Acids. Res. 12:8711–8720] of *Agrobacterium tumefaciens*. The vectors contain: (1) the chimeric gene nopaline synthase::neomycin phosphotransferase (nos::NPTII) as a selectable marker for transformed plant cells [Bevan et al., (1983) Nature 304:184–186], (2) the left and right borders of the T-DNA of the Ti plasmid [Bevan, (1984) Nucl. Acids. Res. 12:8711–8720], (3) the *E. coli* lacZ a-complementing segment [Viering et al., (1982) Gene 19:259–267] with a unique SalI site(pSK97K) or unique HindIII site (pZS97) in the polylinker region, (4) the bacterial replication origin from the Pseudomonas plasmid pVS1 [Itoh et al., (1984) Plasmid 11:206–220], and (5) the bacterial neomycin phosphotransferase gene from Tn5 [Berg et al., (1975) Proc. Natl. Acad. Sci. U.S.A. 72:3628–3632] (pZS97K) or the bacterial β-lactamase gene (pZS97) as selectable markers for transformed *A. tumefaciens*.

Plasmid pZS97K DNA was digested to completion with SalI enzyme and the digested plasmid was gel purified as described in Example 7. The SalI digested pZS97K DNA was mixed with the isolated chimeric gene fragments from Example 7 and ligated at 15° overnight. The ligation mixes were transformed into DH5α [supE44 del lacU169 (phi 80 lacZ del M15) hsdR17 recA1 endA1 gyr196 thi1 relA1] cells and kanamycin-resistant colonies were selected. Plasmid DNAs from kanamycin-resistant colonies were screened by restriction digest analyses and DNA sequencing for the presence of the chimeric genes.

Plasmid pZS97 DNA was digested to completion with HindIII enzyme and the digested plasmid was gel purified as decribed in Example 7. The HindIII digested pZS97 DNA was mixed with the isolated chimeric gene fragments from Example 7, ligated, transformed as above and colonies selected on ampicillin.

Binary vectors containing the chimeric genes were transferred by tri-parental matings [Ruvkin et al., (1981) Nature 289:85–88] to Agrobacterium strain LBA4404/pAL4404 [Hockema et al., (1983), Nature 303:179–180] selecting for kanamycin or carbenicillin resistance. Cultures of Agrobacterium containing the binary vector were used to transform tobacco leaf disks [Horsch et al., (1985) Science 227:1229–1231]. Transgenic plants were regenerated in selective medium containing kanamycin and screened for the presence of the transgenes as described in Example 9.

EXAMPLE 9

ANALYSIS OF TRANSGENIC TOBACCO PLANTS

I. EXTRACTION OF NUCLEIC ACIDS FROM LEAVES

Leaves from plants containing the 35S promoter and the gene for SSPs from clones 86-H23 (SEQ ID NO:48), 88-2 (SEQ ID NO:50), 90-H8 (SEQ ID NO:52) and 3-5 (SEQ ID NO:90) were used to prepare DNA and RNA extracts. These extracts were used for PCR, Southern and Northern blot analysis. Two grams of leaf tissue, derived from leaves 10 cm in length were placed into a mortar containing liquid nitrogen on dry ice. The tissue was ground to a fine powder. This powder was added to 10 mL of extraction buffer [50mm Tris, pH 9.0, 10 mM EDTA, 2% SDS] at 50° C. in a sterile 50 mL polyethylene centrifuge tube. Five milligrams of proteinase K were added and the mixture incubated at 50° C. for 10 min with occasional mixing. The solution was extracted twice with phenol:chloroform:isoamyl alcohol [25:24:1] and twice with chloroform:isoamyl alcohol [24:1]. The aqueous layer was brought to 0.3M sodium acetate and precipitated with 2.5 volumes of ethanol. The pellet, containing the nucleic acids was washed with 70% ethanol and vacuum dried. The pellets were resuspended in 10.0 mL of water, mixed with an equal volume of 4M LiCl$_2$ and allowed to precipitate on ice for one h. The precipitated RNA was collected by centrifugation at 10,000 rpm for 25 min at 4° C., resuspended in 5.0 mL of water and reprecipitated twice more with LiCl$_2$ as above. After the third precipitation, the solution was brought to 0.3M sodium acetate and precipitated with 2.5 volumes of ethanol, washed with 70% ethanol, centrifuged, and resuspended for use in northern blot analysis. The original supernatant containing the DNA was precipitated with 1 volume of isopropanol on dry ice, collected by centrifugation, washed with 70% ethanol and resuspended for use in PCR and southern blot analyses.

II. EXTRACTION OF RNA FROM SEEDS

To analyze expression of SSP gene sequences in seed tissue, RNA was extracted by grinding 200 mg of seeds collected 14 days after flowering under liquid nitrogen to a fine powder with mortar and pestle. The powder was then extracted twice by adding 3 mL phenol:chloroform:isoamyl alcohol (25:24:1) and 4.5 mL of extraction buffer [1M Tris pH 9.0,1% SDS, 5% β-mercaptoethanol]. Nucleic acids in the supernatant were precipitated by adding 1/10th volume 3M sodium acetate and 2.5 volumes of ethanol. The precipitate was collected by centrifugation, washed with 80% ethanol and air dried. The pellet was then resuspended in 4 mL water and 1 mL 10M LiCl$_2$ was added. RNA was precipitated at 4° for 1 hour, collected by centrifugation and the pellet resuspended in 500 μL H$_2$O.

III. PCR ANALYSIS OF PLANT DNAS

To confirm the presence of the SSP gene sequences in the transgenic tobacco plants, extracted DNA was used as the template in polymerase chain reactions. Oligonucleotide primers which annealed to specific promoter and 3' sequences of the transgenes were used. The oligonucleotide primers were as follows:

| | | |
|---|---|---|
| For 35S promoter sequences: | | |
| 35S1 | 5'-TTTGGAGGAGGACACG-3' | (SEQ ID NO:106) |
| For NOS 3' sequences: | | |
| MEH15 | 5'-AAGAGAGAATTGAGAC-3' | (SEQ ID NO:107) |
| For phaseolin promoter sequences: | | |
| SM124 | 5'-GTACTACTACTCTACTACT-3' | (SEQ ID NO:108) |

```
For phaseolin 3' sequences:
SM125                                    (SEQ ID NO:109)
5'-GAGCTCTTACACCTACATGCA-3'
For β-conglycinin promoter sequences:
SM126                                    (SEQ ID NO:110)
5'-CATCAAGAACCAGTTCAATA-3'
```

PCR reaction mixtures included 0.1–0.3 μg of each primer, 1 μg of plant DNA, 4 μL of 2.5 mM dNTPS, 5 μL of 10× reaction buffer (800 mM Tris pH 9.0, 200 mm $(NH_4)_2SO_4$, 15 mM $MgCl_2$), 1 mL Perfect Match™ (Stratagene, La Jolla, Calif.) and $H_2O$ to a final volume of 49 μL. After an initial denaturation at 95° for 5 mins, 1 μL of TAQ™ polymerase was added to each reaction and the following cycle program was run: 1 min at 95°, 1 min at 42° and 3 min at 72° for 40 cycles. PCR generated DNA fragments were separated on 1.2% agarose gels and visualized with ethidium bromide. Bands generated were 100 to 200 bases longer than the SSP coding regions depending on the construct. Plants with correct PCR fragments were designated as positive for the transgene (see Tables 7 and 8).

IV. SOUTHERN BLOT ANALYSES OF PLANT DNAS

DNAs derived from PCR positive plants were further analyzed by digesting 10 μg with BamHI or Asp718 to completion, separating the fragments on a 1.0% agarose gel, transferring the DNA to Hybond M membrane using 20× SSC [Maniatis] and hybridizing the blot with a digoxigenin labelled DNA fragment appropriate to the transgene. Blotting procedures, digoxigenin labelling of probe fragment, hybridization and wash conditions and antibody visualization of signal were as described for the Genius™ blotting kit (USB). Southern blotting analyses for the 35S:SSP3-5:Nos 3' transgenic plants are summarized in Table 7.

V. NORTHERN BLOT ANALYSES OF PLANT RNAS:

RNAS isolated as described above were separated on 1% agarose gel containing 3% formaldehyde in 5 mM sodium tetraborate, 0.18 mM disodium ethylenediaminetetracetic acid. Separated RNAs were transferred to Zetaprobe™ membrane using 20× SSC, the blot hybridized with an appropriate $^{32}p$ labelled DNA probe fragment (probe fragments included promoter, SSP coding region and 3' DNA sequences) at 45°, washed three times with 2×SSC, 0.1% SDS at 25°, then 3× with 0.1×SSC, 0.1% SDS at 55° and the blot autoradiographed. Relative levels of SSP RNA message are summarized in Tables 7 and 8.

VI. EXPRESSION OF SSP PROTEINS IN TRANSGENIC TOBACCO LEAVES

Leaves from plants containing the 35S promoter and the gene for SSP-3-5 were also used to prepare protein extracts. The protein extracts were prepared from leaves 10 cm in length. The central vein was removed and and tissue cut into pieces and weighed. Extraction buffer (1 mL/g tissue): [50 mM Tris·Cl, 1 mM EDTA, 50 mM NaCl, pH 7.5] was added to the tissue in a small mortar on ice. The tissue was ground for approximately 10 min until a smooth paste was obtained. An additional 1 mL of extraction buffer was added for each gram of tissue and the grinding was continued for 5 min longer. The slurry was transferred to eppendorf centrifuge tubes and spun at 10,000 rpm for 15 min at 4° C. The supernatant was removed to a new tube, frozen and respun at full speed in the eppendorf centrifuge for 5 min. The concentration of protein in the sample was determined using the Biorad protein assay and bovine serum albumin as a standard. The supernatant was diluted, mixed with 2× SDS dye buffer (Enprotech), and boiled for 2 min prior to loading 1 μg onto 17 to 27% gradient SDS gels. The gels were blotted onto 0.2 micron nitrocellulose (Biorad), and developed by reaction with the anti-GST-SSP- 3-5 followed by chemiluminescent detection (Amersham) as discussed in Example 5. Results of the Western analyses of leaf tissue are presented in Table 7.

From the Western blotting data it is clear that the SSP-3-5 protein (SEQ ID NO:91) is expressed in leaf tissue at levels up to 0.5% of the total cell protein. The expression level in the leaves from the 35S promoter is positively correlated with the number of gene copies and the steady state level of mRNA. Expression of SSP-3–5 protein (SEQ ID NO:91) in seeds from the 35S promoter is limited to about 0.01%. Since the 35S promoter is known to express poorly in seeds, this finding does not suggest instability of the protein in seeds.

VII. EXPRESSION OF SSPs IN TOBACCO SEEDS

Dried seeds, harvested from transgenic tobacco plants were ground at room temperature in a mortar and pestle with a total of four volumes of extraction buffer [12.5 mM sodium borate, pH 10.0, 1% SDS, 2% 2-mercaptoethanol, 1 mM phenylmethylsulfonylfluoride]. Grinding was initiated with two volumes of buffer. After a paste was achieved, additional phenylmethylsulfonylfluoride was added to bring the final concentration to 2 mM and the final two volumes of buffer were added. The resultant slurry was frozen and then centrifuged in an eppendorf centrifuge for 15 min at 4° C. The supernatant was removed to another tube and the concentration determined using the Biorad Laboratories (Hercules, Calif.) protein assay with bovine serum albumin as a standard. Samples were diluted, SDS gel loading buffer added and electrophoresis was performed on daiichi intermediate gels (10–20% acrylamide). Transfer to nitrocellulose was performed as in Example 5 and the synthetic storage protein detected using polyclonal rabbit anti-GST-SSP3-5 serum. Results of the western analyses of these plants are presented in Table 8.

Amino acid analysis was performed on seeds of these plants. Fifteen mature seeds were placed in a pyrolyzed glass test tube with 100 μL 6N HCl, (double distilled, 5 mL V4COR ampules), 0.4% mercaptoethanol. The suspension was degassed with argon and the tube sealed under argon. The samples were incubated at 110° C.–125° C. for 20–24 hours. The tubes were cracked open, the contents dried and resuspended in 500 μL of dilution buffer (Beckman) containing 2 nmoles of norleucine per 50 μL. Fifty mL were injected onto a Beckman System 6300 amino acid analyzer equipped with an ion exchange amino acid analysis column. The analysis was run according to the manufacturer's recommendations. Eighteen amino acids are analyzed. Lysine is expressed as a percent of total amino acids analyzed. The results are shown in Table 8.

Analyses of transgenic tobacco plants carrying the phaseolin promoter/SSP-3-5 coding region and the phaseolin 3' sequences revealed that the SSP-3-5 gene sequence (SEQ ID NO:90) is stable and that expression of the gene product is correlated to mRNA level. In these plants, the level of accumulation of the protein in the seeds is estimated to be 1–2% of the total seed protein. This level of SSP expression in corn seeds would result in significant increases in lysine and methionine content.

TABLE 7

Northern, Southern, and Western blot analyses of transgenic tobacco plants expressing SSP proteins from the 35S promotor

| Plant # | PCR | Gene Copy Number | Relative mRNA | Approx. ng SSP per μg Total Protein |
|---|---|---|---|---|
| 35S/clone 3-5 | | | | |
| 44B | — | * | — | * |
| 18A | — | * | — | 0 |
| 8A | — | * | — | * |
| 39A | — | 0 | — | 0 |
| 17A | + | * | + | 0 |
| 31A | + | * | +/− | <.5 |
| 14A | + | 1 | + | 2 |
| 41B | + | * | + | 2 |
| 24A | + | * | + | 3 |
| 22A | + | 1 | ++ | 3.5 |
| 40A | + | 2-3 | +++ | 5.0 |
| 35S/clone 86-H23 | | | | |
| 7B | ++ | * | + | * |
| 13A | ++ | * | + | * |
| 17C | ++ | * | + | * |
| 27A | + | * | + | * |
| 35S/clone 88-2 | | | | |
| 18A | + | * | + | * |
| 27B | ++ | * | ++ | * |
| 31A | ++ | * | +++ | * |
| 36A | ++ | * | ++ | * |
| 35S/clone 90H8 | | | | |
| 22A | + | * | +/− | * |
| 34A | ++ | * | +/− | * |
| 31B | + | * | +/− | * |
| 15B | ++ | * | +++ | * |

*Analysis not performed

TABLE 8

Northern, Southern, and Western Blot Analysis of Transfenic Tocacco Plants Expressing SSP-3-5 in Seeds from the Phaseolin Promoter

| Plant # | PCR | Relative mRNA | SSP Detected by Western Blot Analysis | Molar % Lysine Detected in Seeds |
|---|---|---|---|---|
| B38B | ++ | — | — | 2.6 |
| A30B | — | * | — | 2.6 |
| A36B | +/− | — | — | 2.6 |
| B18A | +/− | * | + | 2.9 |
| A40B | +/− | + | + | 2.7 |
| A43B | +/− | + | + | 2.6 |
| A3B | +/− | * | + | 2.8 |
| B8C | +/− | * | + | 2.9 |
| A28A | +/− | * | * | * |
| A38C | — | * | + | 2.9 |
| B5B | ++ | * | + | 3.4 |
| B10D | + | * | + | 4.7 |
| B12A | + | * | + | 2.8 |
| B2A | ++ | + | + | 2.6 |
| B29C | ++ | ++ | + | 2.6 |
| A19A | + | ++ | + | 2.9 |
| A7G | + | +++ | + | 2.6 |
| B20A | ++ | * | ++ | 2.9 |
| B26A | ++ | +++ | ++ | 2.9 |

EXAMPLE 10

EXPRESSION OF SYNTHETIC STORAGE PROTEINS IN RICE PROTOPLASTS

CONSTRUCTION OF THE PLASMID 508/SK29

Figure 13:
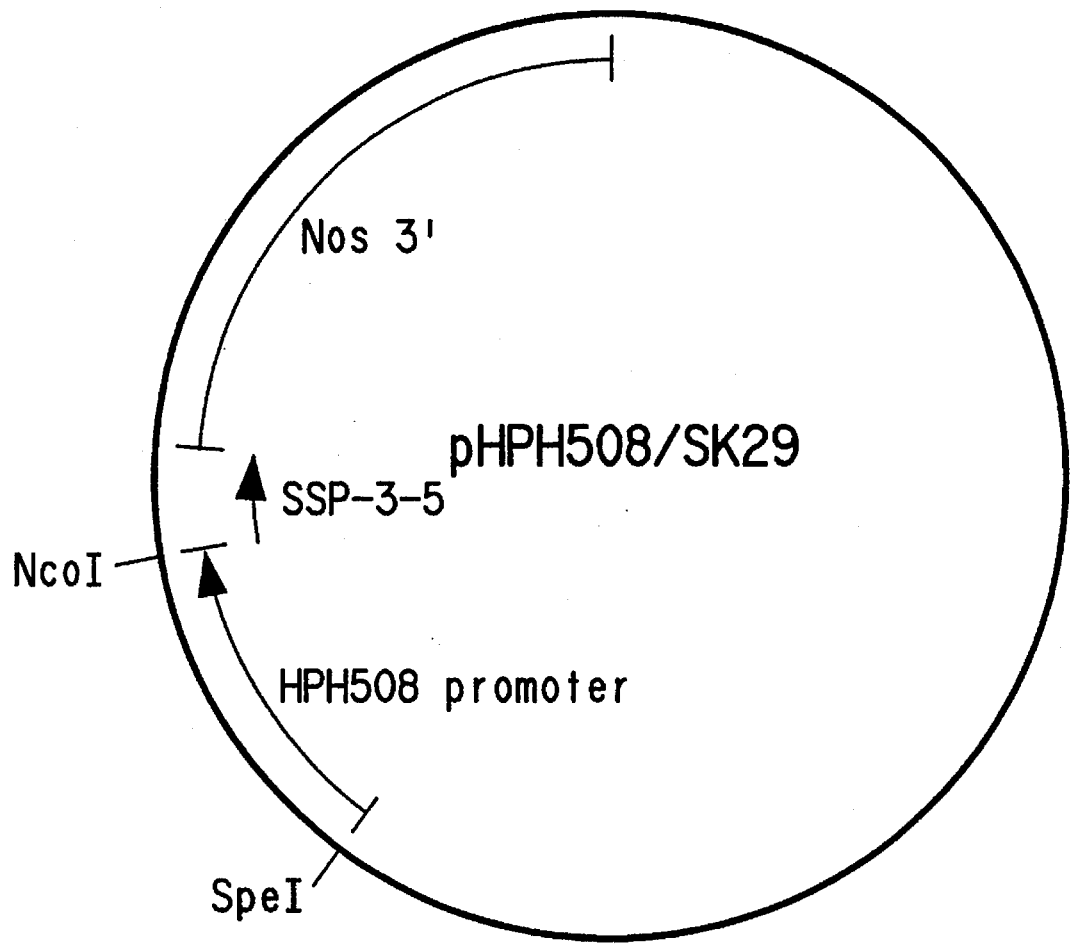
FIG. 13 depicts the construct used for expression of SSP-3-5 protein in, rice protoplast. HPH 508 promoter is a chemically inducible promoter derived from corn.

The SSP-3-5 gene was combined with a chemically inducible monocot promoter HPH508 (Int. Pat. App. PCT/US90/01210, Int. Pub. No. WO90/11361, now issued as U.S. Pat. No. 5,364,780) for use in transient expression assays with rice protoplasts (see FIG. 13). The chemically inducible promoter was chosen to allow Applicants to maximize expression through addition of the chemical inducer.

The construction of the plasmid pA24 has been described in International Patent Application #PCT/US90/01210 and in International Publication #WO90/11361, now issued as U.S. Pat. No. 5,364,780. Plasmid pA24 was digested to completion with the restriction endonucleases SnaBI and HpaI. The digestion products were separated on a 10% polyacrylamide gel. The 76 bp SnaBI/HpaI fragment was excised from the gel and eluted from the polyacrylamide by shaking overnight at 37° C. in elution buffer [Maniatis reference]. Another aliquot of plasmid pA24 was digested to completion with the restriction endonuclease HpaI and treated with calf intestinal alkaline phosphatase (Boehringer). The phosphatased, HpaI digested plasmid and the 76 bp SnaBI/HpaI fragment were ligated together at 16° C. overnight. The ligation was diluted 1:4 with distilled water and 2 μL were used to transform competent HB101 cells (BRL). Ampicillin resistant transformants were screened by restriction endonuclease digestion analysis with HpaI enzyme. This plasmid, containing two copies of the pA24 mutation of the In2–2 inducible element, was designated pHPH508/GUS.

The promoter fragment from pHPH508/GUS was excised from the plasmid as a 325 bp SpeI/NcoI fragment and purified by polyacrylamide gel electrophoresis as above. The plasmid pSK29 (constructed as described in Example 7) containing the SSP-3-5 gene behind the 35S promoter was likewise digested to completion with SpeI and NcoI restriction endonucleases, to remove the 35S promoter fragment, and treated with calf intestinal alkaline phosphatase (Boehringer). The phosphatased plasmid and the 325 bp SpeI/HpaI fragment were ligated together at 16° C. overnight. The ligation was diluted 1:4 with distilled water and 2 μL were used to transform competent HB101 cells (BRL). Ampicillin resistant transformants were screened by restriction digest analysis. The resultant plasmid containing the 325 bp promoter insert was designated pHPH508/SK29 (see FIG. 13).

GENERATION OF RICE PROTOPLASTS

Rice suspension cultures, initiated from anther-derived callus, were maintained by weekly subculture at a 1:4 dilution ratio with fresh liquid N6 medium as described by Chu et al. [Sci sinica 18:659–668] containing 2 mg/mL 2,4-dichlorophenoxyacetic acid and 3% (w/v) sucrose, pH 5.8. Protoplasts were generated from the suspension culture 4–6 days after subculture. Approximately 15 g of tissue were mixed with 4 mL/g tissue of enzyme solution [2% (w/v) cellulase "Onozuka" RS and 0.5% (w/v) Macerozyme R10, (both from Yakult Honsha, Nishinomiya, Japan), 13% (w/v) mannitol, 0.463 g/L $(NH4)_2SO_4$, 2.83 g/L $KNO_3$, 0.4 g/L $KH_2PO_4$, 0.185 g/L $MgSO_4.7H_2O$, 0.166 g/L $CaCl_2.2H_2O$, 3.3 mg/L $MnSO_4$, 1.5 mg/L $ZnSO_4.7H_2O$, 1.6 mg/L $H_3BO_3$, 800 μg/L KI, pH 5.8 (pH with 0.3M citric acid)] in a sterile petri dish and allowed to sit overnight. The suspension was then passed through a sterile 90 micron mesh filter rinsing with sufficient K5.8 media [140 mM NaCl, 3.6 mM KCl, 0.75 mM $Na_2HPO_4.7H_2O$, 5 mM glucose, 125 mM $CaCl_2$, pH 5.8] to bring the final volume of filtrate to 100 mL. The solution was transferred to sterile 50 mL Pyrex® tubes and centrifuged at 500 rpm (50g) for 10 min in a table top IEC swinging bucket centrifuge. The supernatant was removed with a 25 mL pipette and the protoplasts were resuspended in 35 mL of K5.8 media. After 10 min of centrifugation at 500 rpm the supernatant was again removed and the protoplasts were resuspended in 35 mL of N6 medium containing 140 g/L sucrose. After 20 min centrifugation at 500 rpm the protoplasts formed a floating layer and were removed from the top of the tube using disposable plastic pipettes. Two volumes of K5.8 media were added and the final yield (protoplasts/mL) determined using a Fuchs-Rosenthal hemocytometer.

TRANSFORMATION AND LABELLING OF RICE PROTOPLASTS

One million protoplasts were transformed with 5 μg of the plasmid pHPH508/SK29 containing the synthetic storage protein SSP-3-5 gene and a chemically inducible monocot promoter HPH508. Multiple aliquots of the protoplasts (1 million cells each) were centrifuged gently at 50g (500 rpm) for 5 min in sterile polystyrene Falcon 2054 tubes (12×75 mm). The supernatant was discarded and the cells were gently mixed to resuspend them in the remaining liquid. Five μg of transforming DNA in 5 μL of TE [10 mM Tris·Cl, 1 mM EDTA, pH 8.0] were added per million protoplasts. The tubes were shaken gently to disperse the cells in the DNA solution, and 0.1 mL of a solution containing 40% PEG1540 (Polysciences Inc., Warrington, Pa.) and 3 mM $CaCl_2$ were added. The resulting protoplast cell suspension was mixed gently and incubated at room temperature for 1 min. One mL of K5.8 solution containing 200 μg/mL N-(aminocarbonyl)-2-chlorobenzenesulfonamide was then added to dilute out the PEG and to induce the HPH508 promoter. The solution also contained 50 μC/mL $^{35}$S-Methionine (New England Nuclear) to label the SSP-3- 5 protein as it was synthesized. Control protoplasts transformed in an identical manner with pHPH508/GUS were used as a measure of protoplast viability. As with the bacterial expression system, Applicants expected the high methionine content of SSP-3-5 protein to cause it to label better than any other proteins in the rice protoplast.

The transformed protoplasts were allowed to incubate overnight in the dark at 25°–26° C. and the following day methionine was added to a final concentration of 1 mM. GUS assays were performed on control tubes and aliquots were removed from sample tubes for analysis by gel electrophoresis over the next 72 hours. Each aliquot was 100 μL. The aliquots were spun down, washed three times with K5.8+1 mM methionine and resuspended in 50 μL of lysis buffer [50 mM sodium phosphate, pH 7.0, 10 mM β-mercaptoethanol, 10 mM EDTA, 0.1% Triton X-100, 0.1% N-laurylsarcosine]. The resuspended protoplasts were vortexed for one min and centrifuged at 12,000 rpm in an eppendorf centrifuge for 15 min to remove detrites. Gel loading buffer (2×-Enprotech) was mixed 1:1 with the protoplast samples and 10 to 20 μL were loaded on each lane of a 10–20% Daiichi intermediate gel. The gel buffers were Tris-Tricine SDS (Enprotech) and the gel was run at 150 volts for 1.3 h. Fluorography was performed using Enlightning™ (New England Nuclear) according to the manufacturer's directions. The gels were dried onto 0.2 micron nitrocellulose sheets (Biorad) and exposed to Kodak X-Omat RP5 film for 30 min to several days. The identity of SSP-3-5 was confirmed by the $R_f$ value and by immunoprecipitation with the anti GST-SSP-3-5 serum discussed in Example 3.

Immunoprecipitations were done by diluting 40 μL of lysed protoplasts with 10 volumes (400 μL) of TNET buffer [50 mM Tris·Cl, pH 7.5; 150 mM NaCl; 1 mM EDTA; 2% Triton X100]. The sample was spun five min at full speed in an eppendorf centrifuge to remove debrites. Serum from a rabbit immunized with GST-SSP-3-5 (Example 3) was added (5 μL–20 μL) and the sample was incubated at 37° C. from one h to overnight. Killed Staphylococcus Aureus (Calbiochem) cells were added [5 μL of a 10% suspension] and the sample was incubated at 4° C. for 15 min to one h.

The sample was pelleted through a cushion of TNET buffer+ 40% (w/v) sucrose+0.1% (w/v) sodium dodecyl sulfate by spinning for five min at full speed in an eppendorf centrifuge. The pellet was resuspended and washed three times in TNT buffer [50 mM Tris·Cl, pH 7.5; 150 mM NaCl; 1% Triton X100] and finally washed once with 120 mM Tris·Cl, pH 6.8, resuspended in dye buffer (Enprotech) and loaded on an SDS polyacrylamide gel. These experiments demonstrate that the SSP-3-5 protein is stable in rice cells derived from embryogenic suspension cultures. The pulse chase experiments indicated that the half life for protein degradation is roughly the same for the SSP-3-5 protein as for the background rice proteins.

---

What is claimed is:

1. A chimeric gene comprising a nucleic acid fragment encoding a synthetic polypeptide comprising n heptad units in which the residues of each heptad are designated as d e f g a b c, each heptad unit being either the same or different, wherein:

n is at least 4;

a and d are independently selected from the group consisting of Met, Leu, Val, Ile and Thr;

each e and g is independently selected from the group consisting of Glu, Lys, Arg and Asp, provided that, within the same heptad, when e is Glu or Asp, g is Lys or Arg; and when e is Lys or Arg, g is Glu or Asp; and b, c and f are independently any amino acids except Gly or Pro and at least two amino acids of b, c and f in each heptad are selected from the group consisting of Glu, Lys, Asp, Arg, His, Thr, Ser, Asn, Ala, Gln and Cys operably linked to transcriptional and translational regulatory sequences that are functional in plant cells.

2. A chimeric gene of claim 1 wherein said nucleic acid fragment encodes a polypeptide wherein:

a and d are independently selected from the group consisting of Met and Leu.

3. A chimeric gene of claim 1 wherein said nucleic acid fragment encodes a polypeptide wherein:

e and g are independently selected from the group consisting of Glu or lys, provided that, within the same heptad, when e is Glu, g is Lys; and when e is Lys, g is Glu.

4. A chimeric gene of claim 1 wherein said nucleic acid fragment encodes a polypeptide wherein:

b, c and f are selected such that if f is a charged amino acid then b or c carries the opposite charge.

5. A chimeric gene of claim 1 wherein said nucleic acid fragment encodes a synthetic polypeptide comprising n heptad units in which the residues of each heptad are designated as d e f g a b c, each heptad unit being either the same or different wherein:

n is at least 4;

a and d are independently selected from the group consisting of Met and Leu;

each e and g is independently selected from the group consisting of Glu, or Lys, provided that, within the same heptad, when e is Glu, g is Lys;

when e is Lys, g is Glu; and b, c, and f are independently any amino acids except Gly or Pro, at least two amino acids of b, c, and f in each heptad are selected from the group consisting of Glu, Lys, Asp, Arg, His, Thr, Ser, Asn, Ala, Gln, and Cys, and b, c, and f are selected such that if f is a charged amino acid then b or c carries the opposite charge.

6. A chimeric gene of claim 1 wherein said nucleic acid fragment encodes a synthetic polypeptide of n heptads wherein the heptads are selected from the group consisting of:

LEEKLKA (SEQ ID NO:60)
MEEKLKA (SEQ ID NO:61)
MEEKMKA (SEQ ID NO:62)
LEEKLKK (SEQ ID NO:63)
MEEKLKK (SEQ ID NO:64)
MEEKMKK (SEQ ID NO:65)
LEEKLKW (SEQ ID NO:66)
MEEKLKW (SEQ ID NO:67)
LKEELKA (SEQ ID NO:69)
MKEELKA (SEQ ID NO:70)
MKEEMKA (SEQ ID NO:71)
LKEELKK (SEQ ID NO:72)
MKEELKK (SEQ ID NO:73)
MKEEMKK (SEQ ID NO:74)
LKEELKW (SEQ ID NO:75)
MKEELKW (SEQ ID NO:76)
MEEKMKW (SEQ ID NO:68)
MEDKMKW (SEQ ID NO:78)
LKEEMAK (SEQ ID NO:79)
LKEEMKK (SEQ ID NO:80)
MKEEMKW (SEQ ID NO:77)
LEEKMKV (SEQ ID NO:81)
MKDEMWK (SEQ ID NO:82).

7. A chimeric gene of claim 1 wherein said nucleic acid fragment encodes a synthetic polypeptide selected from the group consisting of SEQ ID NOS: 1, 2, 3, 4, 5, 6, 7, 83 and 105.

8. A chimeric gene of claim 1 further comprising an intracellular localization sequence or a sequence encoding a signal peptide is operably joined to the coding sequence for the synthetic polypeptide.

9. A chimeric gene of claim 1 wherein said regulatory sequences are active in seeds.

10. A chimeric gene of claim 9 wherein said regulatory sequences active in seeds are selected from the group consisting of regulatory sequences for soybean kunitz trypsin inhibitor, glycinin, soybean β-conglycinin, soybean lectin, bean lectin, β-phaseolin, 10 kD zein, 27 kD zein, 19 kD zein, globulin 1, and globulin 2.

11. A plant cell transformed with the chimeric gene of claim 1.

12. A plant expressing a polypeptide encoded by a chimeric gene of claim 1 or claim 2 or claim 3 or claim 4 or claim 5 or claim 6 or claim 7.

13. The plant of claim 12 wherein the plant is selected from the group consisting of soybean, tobacco, potato, Brassica spp. and forage grasses.

14. The seeds obtained from a plant of claim 13.

15. Seeds expressing a polypeptide encoded by a chimeric gene of claim 1 or claim 2 or claim 3 or claim 4 or claim 5 or claim 6 or claim 7.

16. A method for increasing the content of essential amino acids in seeds of plants relative to seeds of untransformed plants, comprising:

a. measuring the amino acid content of seeds of a plant;

b. synthesizing a chimeric gene of claim 1 that encodes a polypeptide comprised of one or more essential amino acids which are either missing or present at low levels in step a;

c. transforming a plant cell with the product of step b;

d. regenerating plants from said transformed plant cell of step c to obtain mature plants;

wherein the seeds of the mature plants of step d contain a higher content of essential amino acids than untransformed plants.

17. The plant of claim 13 wherein the Brassica spp. is selected from the group consisting of *B. napus*, *B. campestris*, B-Juncea, and *B. oleracea*.

18. The plant of claim 13 wherein the forage grass is selected from the group consisting of corn, rice, and wheat.

* * * * *

SEQUENCE LISTING ( 1 ) GENERAL INFORMATION:

( i i i ) NUMBER OF SEQUENCES: 113

( 2 ) INFORMATION FOR SEQ ID NO:1:

( i ) SEQUENCE CHARACTERISTICS:
        ( A ) LENGTH: 28 amino acids
        ( B ) TYPE: amino acid
        ( C ) STRANDEDNESS: unknown
        ( D ) TOPOLOGY: unknown ( i i ) MOLECULE TYPE: protein ( i x ) FEATURE:
        ( A ) NAME/KEY: Protein
        ( B ) LOCATION: 1..28
        ( D ) OTHER INFORMATION: /label=name
            / note="(SSP 4)4"

( x i ) SEQUENCE DESCRIPTION: SEQ ID NO:1:

```
Leu Glu Glu Lys Leu Lys Ala Leu Glu Glu Lys Leu Lys Ala Leu Glu
 1               5                  10                  15
Glu Lys Leu Lys Ala Leu Glu Glu Lys Leu Lys Ala
            20                  25
```

( 2 ) INFORMATION FOR SEQ ID NO:2:

( i ) SEQUENCE CHARACTERISTICS:
        ( A ) LENGTH: 28 amino acids
        ( B ) TYPE: amino acid
        ( C ) STRANDEDNESS: unknown
        ( D ) TOPOLOGY: unknown ( i i ) MOLECULE TYPE: protein ( i x ) FEATURE:
        ( A ) NAME/KEY: Protein
        ( B ) LOCATION: 1..28
        ( D ) OTHER INFORMATION: /label=name
            / note="(SSP 5)4"

( x i ) SEQUENCE DESCRIPTION: SEQ ID NO:2:

```
Met Glu Glu Lys Met Lys Ala Met Glu Glu Lys Met Lys Ala Met Glu
 1               5                  10                  15
Glu Lys Met Lys Ala Met Glu Glu Lys Met Lys Ala
            20                  25
```

( 2 ) INFORMATION FOR SEQ ID NO:3:

( i ) SEQUENCE CHARACTERISTICS:
        ( A ) LENGTH: 28 amino acids
        ( B ) TYPE: amino acid
        ( C ) STRANDEDNESS: unknown
        ( D ) TOPOLOGY: unknown ( i i ) MOLECULE TYPE: protein ( i x ) FEATURE:
        ( A ) NAME/KEY: Protein
        ( B ) LOCATION: 1..28

( D ) OTHER INFORMATION: /label=name
/ note="(SSP 7)4"

( x i ) SEQUENCE DESCRIPTION: SEQ ID NO:3:

Met Glu Glu Lys Leu Lys Ala Met Glu Glu Lys Leu Lys Ala Met Glu
1               5                   10                  15
Glu Lys Leu Lys Ala Met Glu Glu Lys Leu Lys Ala
            20                  25

( 2 ) INFORMATION FOR SEQ ID NO:4:

( i ) SEQUENCE CHARACTERISTICS:
    ( A ) LENGTH: 28 amino acids
    ( B ) TYPE: amino acid
    ( C ) STRANDEDNESS: unknown
    ( D ) TOPOLOGY: unknown ( i i ) MOLECULE TYPE: protein ( i x ) FEATURE:
    ( A ) NAME/KEY: Protein
    ( B ) LOCATION: 1..28
    ( D ) OTHER INFORMATION: /label=name
        / note="(SSP 8)4"

( x i ) SEQUENCE DESCRIPTION: SEQ ID NO:4:

Met Glu Glu Lys Leu Lys Lys Met Glu Glu Lys Leu Lys Lys Met Glu
1               5                   10                  15
Glu Lys Leu Lys Lys Met Glu Glu Lys Leu Lys Lys
            20                  25

( 2 ) INFORMATION FOR SEQ ID NO:5:

( i ) SEQUENCE CHARACTERISTICS:
    ( A ) LENGTH: 28 amino acids
    ( B ) TYPE: amino acid
    ( C ) STRANDEDNESS: unknown
    ( D ) TOPOLOGY: unknown ( i i ) MOLECULE TYPE: protein ( i x ) FEATURE:
    ( A ) NAME/KEY: Protein
    ( B ) LOCATION: 1..28
    ( D ) OTHER INFORMATION: /label=name
        / note="(SSP 9)4"

( x i ) SEQUENCE DESCRIPTION: SEQ ID NO:5:

Met Glu Glu Lys Leu Lys Trp Met Glu Glu Lys Leu Lys Trp Met Glu
1               5                   10                  15
Glu Lys Leu Lys Trp Met Glu Glu Lys Leu Lys Trp
            20                  25

( 2 ) INFORMATION FOR SEQ ID NO:6:

( i ) SEQUENCE CHARACTERISTICS:
    ( A ) LENGTH: 28 amino acids
    ( B ) TYPE: amino acid
    ( C ) STRANDEDNESS: unknown
    ( D ) TOPOLOGY: unknown ( i i ) MOLECULE TYPE: protein ( i x ) FEATURE:
    ( A ) NAME/KEY: Protein
    ( B ) LOCATION: 1..28
    ( D ) OTHER INFORMATION: /label=name
        / note="(SSP 10)4"

( x i ) SEQUENCE DESCRIPTION: SEQ ID NO:6:

Met Glu Glu Lys Met Lys Lys Met Glu Glu Lys Met Lys Lys Met Glu
1               5                   10                  15

Glu Lys Met Lys Lys Met Glu Glu Lys Met Lys Lys
            20                  25

( 2 ) INFORMATION FOR SEQ ID NO:7:

( i ) SEQUENCE CHARACTERISTICS:
           ( A ) LENGTH: 28 amino acids
           ( B ) TYPE: amino acid
           ( C ) STRANDEDNESS: unknown
           ( D ) TOPOLOGY: unknown ( i i ) MOLECULE TYPE: protein ( i x ) FEATURE:
           ( A ) NAME/KEY: Protein
           ( B ) LOCATION: 1..28
           ( D ) OTHER INFORMATION: /label=name
                   / note="(SSP 11)4"

( x i ) SEQUENCE DESCRIPTION: SEQ ID NO:7:

Met Glu Glu Lys Met Lys Trp Met Glu Glu Lys Met Lys Trp Met Glu
1               5                   10                  15

Glu Lys Met Lys Trp Met Glu Glu Lys Met Lys Trp
            20                  25

( 2 ) INFORMATION FOR SEQ ID NO:8:

( i ) SEQUENCE CHARACTERISTICS:
           ( A ) LENGTH: 30 amino acids
           ( B ) TYPE: amino acid
           ( C ) STRANDEDNESS: unknown
           ( D ) TOPOLOGY: unknown ( i i ) MOLECULE TYPE: protein ( i x ) FEATURE:
           ( A ) NAME/KEY: Protein
           ( B ) LOCATION: 1..30
           ( D ) OTHER INFORMATION: /label=name
                   / note="CSP 1"

( x i ) SEQUENCE DESCRIPTION: SEQ ID NO:8:

Met Glu Trp Glu Glu Leu Lys Lys Lys Leu Glu Glu Leu Lys Lys Lys
1               5                   10                  15

Trp Glu Glu Leu Lys Lys Lys Leu Glu Glu Leu Lys Lys Lys
            20                  25                  30

( 2 ) INFORMATION FOR SEQ ID NO:9:

( i ) SEQUENCE CHARACTERISTICS:
           ( A ) LENGTH: 20 base pairs
           ( B ) TYPE: nucleic acid
           ( C ) STRANDEDNESS: single
           ( D ) TOPOLOGY: linear ( i i ) MOLECULE TYPE: DNA (genomic)

( i x ) FEATURE:
           ( A ) NAME/KEY: misc_feature
           ( B ) LOCATION: 1..20
           ( D ) OTHER INFORMATION: /product="synthetic oligonucleotide"
                   / standard_name="SM 70"

( x i ) SEQUENCE DESCRIPTION: SEQ ID NO:9:

CTGACTCGCT GCGCTCGGTC                                          20

( 2 ) INFORMATION FOR SEQ ID NO:10:

( i ) SEQUENCE CHARACTERISTICS:
  ( A ) LENGTH: 24 base pairs
  ( B ) TYPE: nucleic acid
  ( C ) STRANDEDNESS: single
  ( D ) TOPOLOGY: linear ( i i ) MOLECULE TYPE: DNA (genomic)

( i x ) FEATURE:
  ( A ) NAME/KEY: misc_feature
  ( B ) LOCATION: 1..24
  ( D ) OTHER INFORMATION: /product="synthetic oligonucleotide"
    / standard_name="SM 71"

( x i ) SEQUENCE DESCRIPTION: SEQ ID NO:10:

TATTTTCTCC TTACGCATCT GTGC    24

( 2 ) INFORMATION FOR SEQ ID NO:11:

( i ) SEQUENCE CHARACTERISTICS:
  ( A ) LENGTH: 27 base pairs
  ( B ) TYPE: nucleic acid
  ( C ) STRANDEDNESS: single
  ( D ) TOPOLOGY: linear ( i i ) MOLECULE TYPE: DNA (genomic)

( i x ) FEATURE:
  ( A ) NAME/KEY: misc_feature
  ( B ) LOCATION: 1..27
  ( D ) OTHER INFORMATION: /product="synthetic oligonucleotide"
    / standard_name="SM 78"

( x i ) SEQUENCE DESCRIPTION: SEQ ID NO:11:

TTCATCGATA GGCGACCACA CCCGTCC    27

( 2 ) INFORMATION FOR SEQ ID NO:12:

( i ) SEQUENCE CHARACTERISTICS:
  ( A ) LENGTH: 27 base pairs
  ( B ) TYPE: nucleic acid
  ( C ) STRANDEDNESS: single
  ( D ) TOPOLOGY: linear ( i i ) MOLECULE TYPE: DNA (genomic)

( i x ) FEATURE:
  ( A ) NAME/KEY: misc_feature
  ( B ) LOCATION: 1..27
  ( D ) OTHER INFORMATION: /product="synthetic oligonucleotide"
    / standard_name="SM 79"

( x i ) SEQUENCE DESCRIPTION: SEQ ID NO:12:

AATATCGATG CCACGATGCG TCCGGCG    27

( 2 ) INFORMATION FOR SEQ ID NO:13:

( i ) SEQUENCE CHARACTERISTICS:
  ( A ) LENGTH: 55 base pairs
  ( B ) TYPE: nucleic acid
  ( C ) STRANDEDNESS: single
  ( D ) TOPOLOGY: linear ( i i ) MOLECULE TYPE: DNA (genomic)

( i x ) FEATURE:
  ( A ) NAME/KEY: misc_feature
  ( B ) LOCATION: 1..55
  ( D ) OTHER INFORMATION: /product="synthetic oligonucleotide"
    / standard_name="SM 81"

( x i ) SEQUENCE DESCRIPTION: SEQ ID NO:13:

CATGGAGGAG AAGATGAAGG CGATGGAAGA GAAGATGAAG GCGTGATAGG TACCG    55

( 2 ) INFORMATION FOR SEQ ID NO:14:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..55
        ( D ) OTHER INFORMATION: /product="synthetic oligonucleotide"
            / standard_name="SM 80"

( x i ) SEQUENCE DESCRIPTION: SEQ ID NO:14:

AATTCGGTAC CTATCACGCC TTCATCTTCT CTTCCATCGC CTTCATCTTC TCCTC     55

( 2 ) INFORMATION FOR SEQ ID NO:15:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..21
        ( D ) OTHER INFORMATION: /product="synthetic oligonucleotide"
            / standard_name="SM 84"

( x i ) SEQUENCE DESCRIPTION: SEQ ID NO:15:

GATGGAGGAG AAGATGAAGG C     21

( 2 ) INFORMATION FOR SEQ ID NO:16:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..21
        ( D ) OTHER INFORMATION: /product="synthetic oligonucleotide"
            / standard_name="SM 85"

( x i ) SEQUENCE DESCRIPTION: SEQ ID NO:16:

ATCGCCTTCA TCTTCTCCTC C     21

( 2 ) INFORMATION FOR SEQ ID NO:17:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..21
        ( D ) OTHER INFORMATION: /product="synthetic oligonucleotide"
            / standard_name="SM 82"

( x i ) SEQUENCE DESCRIPTION: SEQ ID NO:17:

GATGGAGGAG AAGCTGAAGG C                                                          21

( 2 ) INFORMATION FOR SEQ ID NO:18:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..21
        ( D ) OTHER INFORMATION: /product="synthetic oligonucleotide"
            / standard_name="SM 83"

( x i ) SEQUENCE DESCRIPTION: SEQ ID NO:18:

ATCGCCTTCA GCTTCTCCTC C                                                          21

( 2 ) INFORMATION FOR SEQ ID NO:19:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..21
        ( D ) OTHER INFORMATION: /product="synthetic oligonucleotide"
            / standard_name="SM 86"

( x i ) SEQUENCE DESCRIPTION: SEQ ID NO:19:

GATGGAGGAG AAGCTGAAGA A                                                          21

( 2 ) INFORMATION FOR SEQ ID NO:20:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..21
        ( D ) OTHER INFORMATION: /product="synthetic oligonucleotide"
            / standard_name="SM 87"

( x i ) SEQUENCE DESCRIPTION: SEQ ID NO:20:

ATCTTCTTCA GCTTCTCCTC C                                                          21

( 2 ) INFORMATION FOR SEQ ID NO:21:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:

(A) NAME/KEY: misc_feature
(B) LOCATION: 1..21
(D) OTHER INFORMATION: /product="synthetic oligonucleotide"
/ standard_name="SM 88"

(xi) SEQUENCE DESCRIPTION: SEQ ID NO:21:

GATGGAGGAG AAGCTGAAGT G             21

(2) INFORMATION FOR SEQ ID NO:22:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: misc_feature
(B) LOCATION: 1..21
(D) OTHER INFORMATION: /product="synthetic oligonucleotide"
/ standard_name="SM 89"

(xi) SEQUENCE DESCRIPTION: SEQ ID NO:22:

ATCCACTTCA GCTTCTCCTC C             21

(2) INFORMATION FOR SEQ ID NO:23:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: misc_feature
(B) LOCATION: 1..21
(D) OTHER INFORMATION: /product="synthetic oligonucleotide"
/ standard_name="SM 90"

(xi) SEQUENCE DESCRIPTION: SEQ ID NO:23:

GATGGAGGAG AAGATGAAGA A             21

(2) INFORMATION FOR SEQ ID NO:24:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: misc_feature
(B) LOCATION: 1..21
(D) OTHER INFORMATION: /product="synthetic oligonucleotide"
/ standard_name="SM 91"

(xi) SEQUENCE DESCRIPTION: SEQ ID NO:24:

ATCTTCTTCA TCTTCTCCTC C             21

(2) INFORMATION FOR SEQ ID NO:25:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (genomic)

(ix) FEATURE:
 (A) NAME/KEY: misc_feature
 (B) LOCATION: 1..21
 (D) OTHER INFORMATION: /product="synthetic oligonucleotide"
  / standard_name="SM 92"

(xi) SEQUENCE DESCRIPTION: SEQ ID NO:25:

GATGGAGGAG AAGATGAAGT G     21

(2) INFORMATION FOR SEQ ID NO:26:

(i) SEQUENCE CHARACTERISTICS:
  (A) LENGTH: 21 base pairs
  (B) TYPE: nucleic acid
  (C) STRANDEDNESS: single
  (D) TOPOLOGY: linear (ii) MOLECULE TYPE: DNA (genomic)

(ix) FEATURE:
  (A) NAME/KEY: misc_feature
  (B) LOCATION: 1..21
  (D) OTHER INFORMATION: /product="synthetic oligonucleotide"
   / standard_name="SM 93"

(xi) SEQUENCE DESCRIPTION: SEQ ID NO:26:

ATCCACTTCA TCTTCTCCTC C     21

(2) INFORMATION FOR SEQ ID NO:27:

(i) SEQUENCE CHARACTERISTICS:
  (A) LENGTH: 84 base pairs
  (B) TYPE: nucleic acid
  (C) STRANDEDNESS: single
  (D) TOPOLOGY: linear (ii) MOLECULE TYPE: DNA (genomic)

(ix) FEATURE:
  (A) NAME/KEY: misc_feature
  (B) LOCATION: 1..84
  (D) OTHER INFORMATION: /product="synthetic oligonucleotide"
   / standard_name="SM 98"

(xi) SEQUENCE DESCRIPTION: SEQ ID NO:27:

GATGGAGGAA AAGCTGAAAG CGATGGAGGA GAAACTCAAG GCTATGGAAG AAAAGCTTAA    60

AGCGATGGAG GAGAAACTGA AGGC     84

(2) INFORMATION FOR SEQ ID NO:28:

(i) SEQUENCE CHARACTERISTICS:
  (A) LENGTH: 84 base pairs
  (B) TYPE: nucleic acid
  (C) STRANDEDNESS: single
  (D) TOPOLOGY: linear (ii) MOLECULE TYPE: DNA (genomic)

(ix) FEATURE:
  (A) NAME/KEY: misc_feature
  (B) LOCATION: 1..84
  (D) OTHER INFORMATION: /product="synthetic oligonucleotide"
   / standard_name="SM 99"

(xi) SEQUENCE DESCRIPTION: SEQ ID NO:28:

ATCGCCTTCA GTTTCTCCTC CTACGCTTTA AGCTTTTCTT CCATAGCCTT GAGTTTCTCC    60

TCCATCGCTT TCAGCTTTTC CTCC     84

( 2 ) INFORMATION FOR SEQ ID NO:29:

( i ) SEQUENCE CHARACTERISTICS:
    ( A ) LENGTH: 84 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: misc_feature
    ( B ) LOCATION: 1..84
    ( D ) OTHER INFORMATION: /product="synthetic oligonucleotide"
        / standard_name="SM 100"

( x i ) SEQUENCE DESCRIPTION: SEQ ID NO:29:

GATGGAGGAA AAGCTTAAGA AGATGGAAGA AAAGCTGAAA TGGATGGAGG AGAAACTCAA 60

AAAGATGGAG GAAAAGCTTA AATG 84

( 2 ) INFORMATION FOR SEQ ID NO:30:

( i ) SEQUENCE CHARACTERISTICS:
    ( A ) LENGTH: 84 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: misc_feature
    ( B ) LOCATION: 1..84
    ( D ) OTHER INFORMATION: /product="synthetic oligonucleotide"
        / standard_name="SM 101"

( x i ) SEQUENCE DESCRIPTION: SEQ ID NO:30:

ATCCATTTAA GCTTTTCCTC CTACTTTTG AGTTTCTCCT CCATCCATTT CAGCTTTTCT 60

TCCATCTTCT TAAGCTTTTC CTCC 84

( 2 ) INFORMATION FOR SEQ ID NO:31:

( i ) SEQUENCE CHARACTERISTICS:
    ( A ) LENGTH: 30 amino acids
    ( B ) TYPE: amino acid
    ( C ) STRANDEDNESS: unknown
    ( D ) TOPOLOGY: unknown ( i i ) MOLECULE TYPE: protein ( i x ) FEATURE:
    ( A ) NAME/KEY: Protein
    ( B ) LOCATION: 1..30
    ( D ) OTHER INFORMATION: /label=name
        / note="CSP 2"

( x i ) SEQUENCE DESCRIPTION: SEQ ID NO:31:

Met Glu Trp Glu Glu Met Lys Lys Lys Met Glu Glu Met Lys Lys Lys
1               5                   10                  15

Trp Glu Glu Met Lys Lys Lys Met Glu Met Lys Lys Lys
                20                  25                  30

( 2 ) INFORMATION FOR SEQ ID NO:32:

( i ) SEQUENCE CHARACTERISTICS:
    ( A ) LENGTH: 160 base pairs
    ( B ) TYPE: nucleic acid
    ( C ) STRANDEDNESS: double
    ( D ) TOPOLOGY: linear ( i i ) MOLECULE TYPE: DNA (genomic)

( v i ) ORIGINAL SOURCE:
    ( B ) STRAIN: E. coli
    ( G ) CELL TYPE: DH5 alpha ( v i i ) IMMEDIATE SOURCE:
    ( B ) CLONE: C15

( i x ) FEATURE:
    ( A ) NAME/KEY: CDS
    ( B ) LOCATION: 2..151
    ( D ) OTHER INFORMATION: /function="synthetic storage protein"
        / product="protein"
        / gene="ssp"
        / standard_name="5.7.7.7.7.7.5"

( x i ) SEQUENCE DESCRIPTION: SEQ ID NO:32:

```
C ATG GAG GAG AAG ATG AAG GCG ATG GAG GAG AAG CTG AAG GCG ATG       46
  Met Glu Glu Lys Met Lys Ala Met Glu Glu Lys Leu Lys Ala Met
   1               5                  10                  15

GAG GAG AAG CTG AAG GCG ATG GAG GAG AAG CTG AAG GCG ATG GAG GAG    94
Glu Glu Lys Leu Lys Ala Met Glu Glu Lys Leu Lys Ala Met Glu Glu
            20                  25                  30

AAG CTG AAG GCG ATG GAG GAG AAG CTG AAG GCG ATG GAA GAG AAG ATG   142
Lys Leu Lys Ala Met Glu Glu Lys Leu Lys Ala Met Glu Glu Lys Met
                35                  40                  45

AAG GCG TGATAGGTAC CG                                             160
Lys Ala
     50
```

( 2 ) INFORMATION FOR SEQ ID NO:33:

( i ) SEQUENCE CHARACTERISTICS:
    ( A ) LENGTH: 49 amino acids
    ( B ) TYPE: amino acid
    ( D ) TOPOLOGY: linear ( i i ) MOLECULE TYPE: protein ( x i ) SEQUENCE DESCRIPTION: SEQ ID NO:33:

```
Met Glu Glu Lys Met Lys Ala Met Glu Glu Lys Leu Lys Ala Met Glu
 1               5                  10                  15

Glu Lys Leu Lys Ala Met Glu Glu Lys Leu Lys Ala Met Glu Glu Lys
            20                  25                  30

Leu Lys Ala Met Glu Glu Lys Leu Lys Ala Met Glu Glu Lys Met Lys
            35                  40                  45

Ala
```

( 2 ) INFORMATION FOR SEQ ID NO:34:

( i ) SEQUENCE CHARACTERISTICS:
    ( A ) LENGTH: 160 base pairs
    ( B ) TYPE: nucleic acid
    ( C ) STRANDEDNESS: double
    ( D ) TOPOLOGY: linear ( i i ) MOLECULE TYPE: DNA (genomic)

( v i ) ORIGINAL SOURCE:
    ( B ) STRAIN: E. coli
    ( G ) CELL TYPE: DH5 alpha ( v i i ) IMMEDIATE SOURCE:
    ( B ) CLONE: C20

( i x ) FEATURE:
    ( A ) NAME/KEY: CDS
    ( B ) LOCATION: 2..151
    ( D ) OTHER INFORMATION: /function="synthetic storage protein"

/ product="protein"
/ gene="ssp"
/ standard_name="5.7.7.7.7.7.5"

( x i ) SEQUENCE DESCRIPTION: SEQ ID NO:34:

```
C ATG GAG GAG AAG ATG AAG GCG ATG GAG GAG AAG CTG AAG GCG ATG         46
  Met Glu Glu Lys Met Lys Ala Met Glu Glu Lys Leu Lys Ala Met
  1               5                   10                  15

GAG GAG AAG CTG AAG GCG ATG GAG GAG AAG CTG AAG GCG ATG GAG GAG        94
Glu Glu Lys Leu Lys Ala Met Glu Glu Lys Leu Lys Ala Met Glu Glu
                20                  25                  30

AAG CTG AAG GCG ATG GAG GAG AAG CTG AAG GCG ATG GAA GAG AAG ATG       142
Lys Leu Lys Ala Met Glu Glu Lys Leu Lys Ala Met Glu Glu Lys Met
            35                  40                  45

AAG GCG TGATAGGTAC CG                                                  160
Lys Ala
        50
```

( 2 ) INFORMATION FOR SEQ ID NO:35:

( i ) SEQUENCE CHARACTERISTICS:
      ( A ) LENGTH: 49 amino acids
      ( B ) TYPE: amino acid
      ( D ) TOPOLOGY: linear ( i i ) MOLECULE TYPE: protein ( x i ) SEQUENCE DESCRIPTION: SEQ ID NO:35:

```
Met Glu Glu Lys Met Lys Ala Met Glu Glu Lys Leu Lys Ala Met Glu
1               5                   10                  15

Glu Lys Leu Lys Ala Met Glu Glu Lys Leu Lys Ala Met Glu Glu Lys
                20                  25                  30

Leu Lys Ala Met Glu Glu Lys Leu Lys Ala Met Glu Glu Lys Met Lys
            35                  40                  45

Ala
```

( 2 ) INFORMATION FOR SEQ ID NO:36:

( i ) SEQUENCE CHARACTERISTICS:
      ( A ) LENGTH: 139 base pairs
      ( B ) TYPE: nucleic acid
      ( C ) STRANDEDNESS: double
      ( D ) TOPOLOGY: linear ( i i ) MOLECULE TYPE: DNA (genomic)

( v i ) ORIGINAL SOURCE:
      ( B ) STRAIN: E. coli
      ( G ) CELL TYPE: DH5 alpha ( v i i ) IMMEDIATE SOURCE:
      ( B ) CLONE: C30

( i x ) FEATURE:
      ( A ) NAME/KEY: CDS
      ( B ) LOCATION: 2..130
      ( D ) OTHER INFORMATION: /function="synthetic storage protein"
         / product="protein"
         / gene="ssp"
         / standard_name="5.7.7.7.7.5"

( x i ) SEQUENCE DESCRIPTION: SEQ ID NO:36:

```
C ATG GAG GAG AAG ATG AAG GCG ATG GAG GAG AAG CTG AAG GCG ATG         46
  Met Glu Glu Lys Met Lys Ala Met Glu Glu Lys Leu Lys Ala Met
  1               5                   10                  15

GAG GAG AAG CTG AAG GCG ATG GAG GAG AAG CTG AAG GCG ATG GAG GAG        94
Glu Glu Lys Leu Lys Ala Met Glu Glu Lys Leu Lys Ala Met Glu Glu
                20                  25                  30
```

```
AAG CTG AAG GCG ATG GAA GAG AAG ATG AAG GCG TGATAGGTAC CG              139
Lys Leu Lys Ala Met Glu Glu Lys Met Lys Ala
         35                      40
```

(2) INFORMATION FOR SEQ ID NO:37:

(i) SEQUENCE CHARACTERISTICS:
        (A) LENGTH: 42 amino acids
        (B) TYPE: amino acid
        (D) TOPOLOGY: linear (ii) MOLECULE TYPE: protein (xi) SEQUENCE DESCRIPTION: SEQ ID NO:37:

```
Met Glu Glu Lys Met Lys Ala Met Glu Glu Lys Leu Lys Ala Met Glu
 1               5                  10                  15
Glu Lys Leu Lys Ala Met Glu Glu Lys Leu Lys Ala Met Glu Glu Lys
                20                  25                  30
Leu Lys Ala Met Glu Glu Lys Met Lys Ala
             35                  40
```

(2) INFORMATION FOR SEQ ID NO:38:

(i) SEQUENCE CHARACTERISTICS:
        (A) LENGTH: 97 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (B) STRAIN: E. coli
        (G) CELL TYPE: DH5 alpha (vii) IMMEDIATE SOURCE:
        (B) CLONE: D16

(ix) FEATURE:
        (A) NAME/KEY: CDS
        (B) LOCATION: 2..88
        (D) OTHER INFORMATION: /function="synthetic storage protein"
            / product="protein"
            / gene="ssp"
            / standard_name="5.5.5.5"

(xi) SEQUENCE DESCRIPTION: SEQ ID NO:38:

```
C ATG GAG GAG AAG ATG AAG GCG ATG GAG GAG AAG ATG AAG GCG ATG          46
  Met Glu Glu Lys Met Lys Ala Met Glu Glu Lys Met Lys Ala Met
   1               5                  10                  15
GAG GAG AAG ATG AAG GCG ATG GAA GAG AAG ATG AAG GCG TGATAGGTAC          95
Glu Glu Lys Met Lys Ala Met Glu Glu Lys Met Lys Ala
                20                  25
CG                                                                      97
```

(2) INFORMATION FOR SEQ ID NO:39:

(i) SEQUENCE CHARACTERISTICS:
        (A) LENGTH: 28 amino acids
        (B) TYPE: amino acid
        (D) TOPOLOGY: linear (ii) MOLECULE TYPE: protein (xi) SEQUENCE DESCRIPTION: SEQ ID NO:39:

```
Met Glu Glu Lys Met Lys Ala Met Glu Glu Lys Met Lys Ala Met Glu
 1               5                  10                  15
Glu Lys Met Lys Ala Met Glu Glu Lys Met Lys Ala
```

2 0                                   2 5

( 2 ) INFORMATION FOR SEQ ID NO:40:

( i ) SEQUENCE CHARACTERISTICS:
        ( A ) LENGTH: 118 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( B ) STRAIN: E. coli
        ( G ) CELL TYPE: DH5 alpha ( v i i ) IMMEDIATE SOURCE:
        ( B ) CLONE: D20

( i x ) FEATURE:
        ( A ) NAME/KEY: CDS
        ( B ) LOCATION: 2..109
        ( D ) OTHER INFORMATION: /function="synthetic storage protein"
            / product="protein"
            / gene="ssp"
            / standard_name="5.5.5.5.5"

( x i ) SEQUENCE DESCRIPTION: SEQ ID NO:40:

```
C ATG GAG GAG AAG ATG AAG GCG ATG GAG GAG AAG ATG AAG GCG ATG         46
  Met Glu Glu Lys Met Lys Ala Met Glu Glu Lys Met Lys Ala Met
  1               5                   10                  15

GAG GAG AAG ATG AAG GCG ATG GAG GAG AAG ATG AAG GCG ATG GAA GAG       94
Glu Glu Lys Met Lys Ala Met Glu Glu Lys Met Lys Ala Met Glu Glu
                20                  25                  30

AAG ATG AAG GCG TGATAGGTAC CG                                        118
Lys Met Lys Ala
            35
```

( 2 ) INFORMATION FOR SEQ ID NO:41:

( i ) SEQUENCE CHARACTERISTICS:
        ( A ) LENGTH: 35 amino acids
        ( B ) TYPE: amino acid
        ( D ) TOPOLOGY: linear ( i i ) MOLECULE TYPE: protein ( x i ) SEQUENCE DESCRIPTION: SEQ ID NO:41:

```
Met Glu Glu Lys Met Lys Ala Met Glu Glu Lys Met Lys Ala Met Glu
1               5                   10                  15

Glu Lys Met Lys Ala Met Glu Glu Lys Met Lys Ala Met Glu Glu Lys
                20                  25                  30

Met Lys Ala
        35
```

( 2 ) INFORMATION FOR SEQ ID NO:42:

( i ) SEQUENCE CHARACTERISTICS:
        ( A ) LENGTH: 97 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( B ) STRAIN: E. coli
        ( G ) CELL TYPE: DH5 alpha ( v i i ) IMMEDIATE SOURCE:
        ( B ) CLONE: D33

( i x ) FEATURE:
  ( A ) NAME/KEY: CDS
  ( B ) LOCATION: 2..88
  ( D ) OTHER INFORMATION: /function="synthetic storage protein"
    / product="protein"
    / gene="ssp"
    / standard_name="5.5.5.5"

( x i ) SEQUENCE DESCRIPTION: SEQ ID NO:42:

```
C ATG GAG GAG AAG ATG AAG GCG ATG GAG GAG AAG ATG AAG GCG ATG      46
  Met Glu Glu Lys Met Lys Ala Met Glu Glu Lys Met Lys Ala Met
  1               5                   10                  15

GAG GAG AAG ATG AAG GCG ATG GAA GAG AAG ATG AAG GCG TGATAGGTAC     95
Glu Glu Lys Met Lys Ala Met Glu Glu Lys Met Lys Ala
            20                  25

CG                                                                  97
```

( 2 ) INFORMATION FOR SEQ ID NO:43:

( i ) SEQUENCE CHARACTERISTICS:
    ( A ) LENGTH: 28 amino acids
    ( B ) TYPE: amino acid
    ( D ) TOPOLOGY: linear ( i i ) MOLECULE TYPE: protein ( x i ) SEQUENCE DESCRIPTION: SEQ ID NO:43:

```
Met Glu Glu Lys Met Lys Ala Met Glu Glu Lys Met Lys Ala Met Glu
1               5                   10                  15

Glu Lys Met Lys Ala Met Glu Glu Lys Met Lys Ala
            20                  25
```

( 2 ) INFORMATION FOR SEQ ID NO:44:

( i ) SEQUENCE CHARACTERISTICS:
    ( A ) LENGTH: 160 base pairs
    ( B ) TYPE: nucleic acid
    ( C ) STRANDEDNESS: double
    ( D ) TOPOLOGY: linear ( i i ) MOLECULE TYPE: DNA (genomic)

( v i ) ORIGINAL SOURCE:
    ( B ) STRAIN: E. coli
    ( G ) CELL TYPE: DH5 alpha ( v i i ) IMMEDIATE SOURCE:
    ( B ) CLONE: 82-4

( i x ) FEATURE:
    ( A ) NAME/KEY: CDS
    ( B ) LOCATION: 2..151
    ( D ) OTHER INFORMATION: /function="synthetic storage protein
      / product="protein"
      / gene="ssp"
      / standard_name="7.7.7.7.7.7.5"

( x i ) SEQUENCE DESCRIPTION: SEQ ID NO:44:

```
C ATG GAG GAG AAG CTG AAG GCG ATG GAG GAG AAG CTG AAG GCG ATG      46
  Met Glu Glu Lys Leu Lys Ala Met Glu Glu Lys Leu Lys Ala Met
  1               5                   10                  15

GAG GAG AAG CTG AAG GCG ATG GAG GAG AAG CTG AAG GCG ATG GAG GAG    94
Glu Glu Lys Leu Lys Ala Met Glu Glu Lys Leu Lys Ala Met Glu Glu
            20                  25                  30

AAG CTG AAG GCG ATG GAG GAG AAG CTG AAG GCG ATG GAA GAG AAG ATG   142
Lys Leu Lys Ala Met Glu Glu Lys Leu Lys Ala Met Glu Glu Lys Met
            35                  40                  45

AAG GCG TGATAGGTAC CG                                              160
```

Lys Ala
     50

( 2 ) INFORMATION FOR SEQ ID NO:45:

( i ) SEQUENCE CHARACTERISTICS:
        ( A ) LENGTH: 49 amino acids
        ( B ) TYPE: amino acid
        ( D ) TOPOLOGY: linear ( i i ) MOLECULE TYPE: protein ( x i ) SEQUENCE DESCRIPTION: SEQ ID NO:45:

Met Glu Glu Lys Leu Lys Ala Met Glu Glu Lys Leu Lys Ala Met Glu
 1               5                  10                  15

Glu Lys Leu Lys Ala Met Glu Glu Lys Leu Lys Ala Met Glu Glu Lys
                20                  25                  30

Leu Lys Ala Met Glu Glu Lys Leu Lys Ala Met Glu Glu Lys Met Lys
            35                  40                  45

Ala ( 2 ) INFORMATION FOR SEQ ID NO:46:

( i ) SEQUENCE CHARACTERISTICS:
        ( A ) LENGTH: 97 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( B ) STRAIN: E. coli
        ( G ) CELL TYPE: DH5 alpha ( v i i ) IMMEDIATE SOURCE:
        ( B ) CLONE: 84-H3

( i x ) FEATURE:
        ( A ) NAME/KEY: CDS
        ( B ) LOCATION: 2..88
        ( D ) OTHER INFORMATION: /function="synthetic storage protein
            / product="protein"
            / gene="ssp"
            / standard_name="5.5.5.5"

( x i ) SEQUENCE DESCRIPTION: SEQ ID NO:46:

C ATG GAG GAG AAG ATG AAG GCG ATG GAG GAG AAG ATG AAG GCG ATG    46
  Met Glu Glu Lys Met Lys Ala Met Glu Glu Lys Met Lys Ala Met
   1               5                  10                  15

GAG GAG AAG ATG AAG GCG ATG GAA GAG AAG ATG AAG GCG TGATAGGTAC   95
Glu Glu Lys Met Lys Ala Met Glu Glu Lys Met Lys Ala
                20                  25

CG                                                                97

( 2 ) INFORMATION FOR SEQ ID NO:47:

( i ) SEQUENCE CHARACTERISTICS:
        ( A ) LENGTH: 28 amino acids
        ( B ) TYPE: amino acid
        ( D ) TOPOLOGY: linear ( i i ) MOLECULE TYPE: protein ( x i ) SEQUENCE DESCRIPTION: SEQ ID NO:47:

Met Glu Glu Lys Met Lys Ala Met Glu Glu Lys Met Lys Ala Met Glu
 1               5                  10                  15

Glu Lys Met Lys Ala Met Glu Glu Lys Met Lys Ala ( 2 ) INFORMATION FOR SEQ ID NO:48:

( i ) SEQUENCE CHARACTERISTICS:
        ( A ) LENGTH: 97 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( B ) STRAIN: E. coli
        ( G ) CELL TYPE: DH5 alpha ( v i i ) IMMEDIATE SOURCE:
        ( B ) CLONE: 86-H23

( i x ) FEATURE:
        ( A ) NAME/KEY: CDS
        ( B ) LOCATION: 2..88
        ( D ) OTHER INFORMATION: /function="synthetic storage protein
            / product="protein"
            / gene="ssp"
            / standard_name="5.8.8.5"

( x i ) SEQUENCE DESCRIPTION: SEQ ID NO:48:

```
C ATG GAG GAG AAG ATG AAG GCG ATG GAG GAG AAG CTG AAG AAG ATG      46
  Met Glu Glu Lys Met Lys Ala Met Glu Glu Lys Leu Lys Lys Met
  1               5                   10                  15

GAG GAG AAG CTG AAG AAG ATG GAA GAG AAG ATG AAG GCG TGATAGGTAC    95
Glu Glu Lys Leu Lys Lys Met Glu Glu Lys Met Lys Ala
                20                  25

CG                                                                97
```

( 2 ) INFORMATION FOR SEQ ID NO:49:

( i ) SEQUENCE CHARACTERISTICS:
        ( A ) LENGTH: 28 amino acids
        ( B ) TYPE: amino acid
        ( D ) TOPOLOGY: linear ( i i ) MOLECULE TYPE: protein ( x i ) SEQUENCE DESCRIPTION: SEQ ID NO:49:

```
Met Glu Glu Lys Met Lys Ala Met Glu Glu Lys Leu Lys Lys Met Glu
1               5                   10                  15

Glu Lys Leu Lys Lys Met Glu Glu Lys Met Lys Ala
                20                  25
```

( 2 ) INFORMATION FOR SEQ ID NO:50:

( i ) SEQUENCE CHARACTERISTICS:
        ( A ) LENGTH: 112 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( B ) STRAIN: E. coli
        ( G ) CELL TYPE: DH5 alpha ( v i i ) IMMEDIATE SOURCE:
        ( B ) CLONE: 88-2

( i x ) FEATURE:
        ( A ) NAME/KEY: CDS
        ( B ) LOCATION: 2..103
        ( D ) OTHER INFORMATION: /function="synthetic storage protein / product="protein"
/ gene="ssp"
/ standard_name="5.9.9.9.5"

( x i ) SEQUENCE DESCRIPTION: SEQ ID NO:50:

```
C ATG GAG GAG AAG ATG AAG GCG AAG AAG CTG AAG TGG ATG GAG GAG      46
  Met Glu Glu Lys Met Lys Ala Lys Lys Leu Lys Trp Met Glu Glu
  1               5                   10                  15

AAG CTG AAG TGG ATG GAG GAG AAG CTG AAG TGG ATG GAA GAG AAG ATG    94
Lys Leu Lys Trp Met Glu Glu Lys Leu Lys Trp Met Glu Glu Lys Met
                20                  25                  30

AAG GCG TGATAGGTAC CG                                             112
Lys Ala
```

( 2 ) INFORMATION FOR SEQ ID NO:51:

( i ) SEQUENCE CHARACTERISTICS:
        ( A ) LENGTH: 33 amino acids
        ( B ) TYPE: amino acid
        ( D ) TOPOLOGY: linear ( i i ) MOLECULE TYPE: protein ( x i ) SEQUENCE DESCRIPTION: SEQ ID NO:51:

```
Met Glu Glu Lys Met Lys Ala Lys Lys Leu Lys Trp Met Glu Glu Lys
1               5                   10                  15

Leu Lys Trp Met Glu Glu Lys Leu Lys Trp Met Glu Glu Lys Met Lys
                20                  25                  30

Ala
```

( 2 ) INFORMATION FOR SEQ ID NO:52:

( i ) SEQUENCE CHARACTERISTICS:
        ( A ) LENGTH: 118 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( B ) STRAIN: E. coli
        ( G ) CELL TYPE: DH5 alpha ( v i i ) IMMEDIATE SOURCE:
        ( B ) CLONE: 90-H8

( i x ) FEATURE:
        ( A ) NAME/KEY: CDS
        ( B ) LOCATION: 2..109
        ( D ) OTHER INFORMATION: /function="synthetic storage protein
            / product="protein"
            / gene="ssp"
            / standard_name="5.10.10.10.5"

( x i ) SEQUENCE DESCRIPTION: SEQ ID NO:52:

```
C ATG GAG GAG AAG ATG AAG GCG ATG GAG GAG AAG ATG AAG AAG ATG      46
  Met Glu Glu Lys Met Lys Ala Met Glu Glu Lys Met Lys Lys Met
  1               5                   10                  15

GAG GAG AAG ATG AAG AAG ATG GAG GAG AAG ATG AAG AAG ATG GAA GAG    94
Glu Glu Lys Met Lys Lys Met Glu Glu Lys Met Lys Lys Met Glu Glu
                20                  25                  30

AAG ATG AAG GCG TGATAGGTAC CG                                     118
Lys Met Lys Ala
            35
```

( 2 ) INFORMATION FOR SEQ ID NO:53:

( i ) SEQUENCE CHARACTERISTICS:
  ( A ) LENGTH: 35 amino acids
  ( B ) TYPE: amino acid
  ( D ) TOPOLOGY: linear ( i i ) MOLECULE TYPE: protein ( x i ) SEQUENCE DESCRIPTION: SEQ ID NO:53:

```
Met Glu Glu Lys Met Lys Ala Met Glu Glu Lys Met Lys Lys Met Glu
 1               5                   10                  15
Glu Lys Met Lys Lys Met Glu Glu Lys Met Lys Lys Met Glu Glu Lys
            20                  25                  30
Met Lys Ala
        35
```

( 2 ) INFORMATION FOR SEQ ID NO:54:

( i ) SEQUENCE CHARACTERISTICS:
  ( A ) LENGTH: 97 base pairs
  ( B ) TYPE: nucleic acid
  ( C ) STRANDEDNESS: double
  ( D ) TOPOLOGY: linear ( i i ) MOLECULE TYPE: DNA (genomic)

( v i ) ORIGINAL SOURCE:
  ( B ) STRAIN: E. coli
  ( G ) CELL TYPE: DH5 alpha ( v i i ) IMMEDIATE SOURCE:
  ( B ) CLONE: 92-2

( i x ) FEATURE:
  ( A ) NAME/KEY: CDS
  ( B ) LOCATION: 2..88
  ( D ) OTHER INFORMATION: /function="synthetic storage protein
   / product="protein"
   / gene="ssp"
   / standard_name="5.11.11.5"

( x i ) SEQUENCE DESCRIPTION: SEQ ID NO:54:

```
C ATG GAG GAG AAG ATG AAG GCG ATG GAG GAG AAG ATG AAG TGG ATG      46
  Met Glu Glu Lys Met Lys Ala Met Glu Glu Lys Met Lys Trp Met
   1               5                   10                  15

GAG GAG AAG ATG AAG TGG ATG GAA GAG AAG ATG AAG GCG TGATAGGTAC     95
Glu Glu Lys Met Lys Trp Met Glu Glu Lys Met Lys Ala
            20                  25

C G                                                                97
```

( 2 ) INFORMATION FOR SEQ ID NO:55:

( i ) SEQUENCE CHARACTERISTICS:
  ( A ) LENGTH: 28 amino acids
  ( B ) TYPE: amino acid
  ( D ) TOPOLOGY: linear ( i i ) MOLECULE TYPE: protein ( x i ) SEQUENCE DESCRIPTION: SEQ ID NO:55:

```
Met Glu Glu Lys Met Lys Ala Met Glu Glu Lys Met Lys Trp Met Glu
 1               5                   10                  15
Glu Lys Met Lys Trp Met Glu Glu Lys Met Lys Ala
            20                  25
```

( 2 ) INFORMATION FOR SEQ ID NO:56:

( i ) SEQUENCE CHARACTERISTICS:
  ( A ) LENGTH: 243 base pairs
  ( B ) TYPE: nucleic acid ( C ) STRANDEDNESS: double
( D ) TOPOLOGY: linear ( i i ) MOLECULE TYPE: DNA (genomic)

( v i ) ORIGINAL SOURCE:
( B ) STRAIN: E. coli
( G ) CELL TYPE: DH5 alpha ( v i i ) IMMEDIATE SOURCE:
( B ) CLONE: 2-9

( i x ) FEATURE:
( A ) NAME/KEY: CDS
( B ) LOCATION: 2..235
( D ) OTHER INFORMATION: /function="synthetic storage protein
/ product="protein"
/ gene="ssp"
/ standard_name="7.7.7.7.7.7.8.9.8.9.5"

( x i ) SEQUENCE DESCRIPTION: SEQ ID NO:56:

| C | ATG | GAG | GAG | AAG | CTG | AAG | GCG | ATG | GAG | GAG | AAG | CTG | AAG | GCG | ATG | | 46 |
|---|-----|-----|-----|-----|-----|-----|-----|-----|-----|-----|-----|-----|-----|-----|-----|---|----|
|   | Met | Glu | Glu | Lys | Leu | Lys | Ala | Met | Glu | Glu | Lys | Leu | Lys | Ala | Met |   |    |
|   | 1   |     |     |     | 5   |     |     |     | 10  |     |     |     |     |     | 15  |   |    |

| GAG | GAG | AAG | CTG | AAG | GCG | ATG | GAG | GAG | AAG | CTG | AAG | GCG | ATG | GAG | GAG | 94 |
|-----|-----|-----|-----|-----|-----|-----|-----|-----|-----|-----|-----|-----|-----|-----|-----|----|
| Glu | Glu | Lys | Leu | Lys | Ala | Met | Glu | Glu | Lys | Leu | Lys | Ala | Met | Glu | Glu |    |
|     |     |     |     | 20  |     |     |     |     | 25  |     |     |     |     | 30  |     |    |

| AAG | CTG | AAG | GCG | ATG | GAG | GAG | AAG | CTG | AAG | GCG | ATG | GAG | GAA | AAG | CTT | 142 |
|-----|-----|-----|-----|-----|-----|-----|-----|-----|-----|-----|-----|-----|-----|-----|-----|-----|
| Lys | Leu | Lys | Ala | Met | Glu | Glu | Lys | Leu | Lys | Ala | Met | Glu | Glu | Lys | Leu |     |
|     |     |     | 35  |     |     |     |     | 40  |     |     |     |     | 45  |     |     |     |

| AAG | AAG | ATG | GAA | GAA | AAG | CTG | AAA | TGG | ATG | GAG | GAG | AAA | CTC | AAA | AAG | 190 |
|-----|-----|-----|-----|-----|-----|-----|-----|-----|-----|-----|-----|-----|-----|-----|-----|-----|
| Lys | Lys | Met | Glu | Glu | Lys | Leu | Lys | Trp | Met | Glu | Glu | Lys | Leu | Lys | Lys |     |
|     |     | 50  |     |     |     |     | 55  |     |     |     |     | 60  |     |     |     |     |

| ATG | GAG | GAA | AAG | CTT | AAA | TGG | ATG | GAA | GAG | AAG | ATG | AAG | GCG | TGATAGGTAC | 242 |
|-----|-----|-----|-----|-----|-----|-----|-----|-----|-----|-----|-----|-----|-----|------------|-----|
| Met | Glu | Glu | Lys | Leu | Lys | Trp | Met | Glu | Glu | Lys | Met | Lys | Ala |            |     |
|     | 65  |     |     |     |     | 70  |     |     |     |     | 75  |     |     |            |     |

C                                                                                                                                    243

( 2 ) INFORMATION FOR SEQ ID NO:57:

( i ) SEQUENCE CHARACTERISTICS:
( A ) LENGTH: 77 amino acids
( B ) TYPE: amino acid
( D ) TOPOLOGY: linear ( i i ) MOLECULE TYPE: protein ( x i ) SEQUENCE DESCRIPTION: SEQ ID NO:57:

| Met | Glu | Glu | Lys | Leu | Lys | Ala | Met | Glu | Glu | Lys | Leu | Lys | Ala | Met | Glu |
|-----|-----|-----|-----|-----|-----|-----|-----|-----|-----|-----|-----|-----|-----|-----|-----|
| 1   |     |     |     | 5   |     |     |     | 10  |     |     |     |     |     | 15  |     |

| Glu | Lys | Leu | Lys | Ala | Met | Glu | Glu | Lys | Leu | Lys | Ala | Met | Glu | Glu | Lys |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Leu | Lys | Ala | Met | Glu | Glu | Lys | Leu | Lys | Ala | Met | Glu | Glu | Lys | Leu | Lys |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Lys | Met | Glu | Glu | Lys | Leu | Lys | Trp | Met | Glu | Glu | Lys | Leu | Lys | Lys | Met |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Glu | Glu | Lys | Leu | Lys | Trp | Met | Glu | Glu | Lys | Met | Lys | Ala |
|-----|-----|-----|-----|-----|-----|-----|-----|-----|-----|-----|-----|-----|
| 65  |     |     |     |     | 70  |     |     |     |     | 75  |     |     |

( 2 ) INFORMATION FOR SEQ ID NO:58:

( i ) SEQUENCE CHARACTERISTICS:
( A ) LENGTH: 175 base pairs
( B ) TYPE: nucleic acid
( C ) STRANDEDNESS: double
( D ) TOPOLOGY: linear ( i i ) MOLECULE TYPE: DNA (genomic)

( v i ) ORIGINAL SOURCE:
    ( B ) STRAIN: E. coli
    ( G ) CELL TYPE: DH5 alpha ( v i i ) IMMEDIATE SOURCE:
    ( B ) CLONE: 5-1

( i x ) FEATURE:
    ( A ) NAME/KEY: CDS
    ( B ) LOCATION: 2..172
    ( D ) OTHER INFORMATION: /function="synthetic storage protein
        / product="protein"
        / gene="ssp"
        / standard_name="5.5.5.7.7.7.7.5"

( x i ) SEQUENCE DESCRIPTION: SEQ ID NO:58:

```
C ATG GAG GAG AAG ATG AAG GCG ATG GAG GAG AAG ATG AAG GCG ATG      46
  Met Glu Glu Lys Met Lys Ala Met Glu Glu Lys Met Lys Ala Met
  1               5                   10                  15

GAG GAG AAG ATG AAG GCG ATG GAG GAA AAG CTG AAA GCG ATG GAG GAG    94
Glu Glu Lys Met Lys Ala Met Glu Glu Lys Leu Lys Ala Met Glu Glu
            20                  25                  30

AAA CTC AAG GCT ATG GAA GAA AAG CTT AAA GCG ATG GAG GAG AAA CTG   142
Lys Leu Lys Ala Met Glu Glu Lys Leu Lys Ala Met Glu Glu Lys Leu
            35                  40                  45

AAG GCC ATG GAA GAG AAG ATG AAG GCG TGATAG                        175
Lys Ala Met Glu Glu Lys Met Lys Ala
            50                  55
```

( 2 ) INFORMATION FOR SEQ ID NO:59:

( i ) SEQUENCE CHARACTERISTICS:
        ( A ) LENGTH: 56 amino acids
        ( B ) TYPE: amino acid
        ( D ) TOPOLOGY: linear ( i i ) MOLECULE TYPE: protein ( x i ) SEQUENCE DESCRIPTION: SEQ ID NO:59:

```
Met Glu Glu Lys Met Lys Ala Met Glu Glu Lys Met Lys Ala Met Glu
1               5                   10                  15

Glu Lys Met Lys Ala Met Glu Glu Lys Leu Lys Ala Met Glu Glu Lys
            20                  25                  30

Leu Lys Ala Met Glu Glu Lys Leu Lys Ala Met Glu Glu Lys Leu Lys
            35                  40                  45

Ala Met Glu Glu Lys Met Lys Ala
            50                  55
```

( 2 ) INFORMATION FOR SEQ ID NO:60:

( i ) SEQUENCE CHARACTERISTICS:
        ( A ) LENGTH: 7 amino acids
        ( B ) TYPE: amino acid
        ( C ) STRANDEDNESS: unknown
        ( D ) TOPOLOGY: unknown ( i i ) MOLECULE TYPE: protein ( i x ) FEATURE:
        ( A ) NAME/KEY: Protein
        ( B ) LOCATION: 1..7
        ( D ) OTHER INFORMATION: /label=name
            / note="SSP 4"

( x i ) SEQUENCE DESCRIPTION: SEQ ID NO:60:

```
Leu Glu Glu Lys Leu Lys Ala
1               5
```

( 2 ) INFORMATION FOR SEQ ID NO:61:

( i ) SEQUENCE CHARACTERISTICS:
      ( A ) LENGTH: 7 amino acids
      ( B ) TYPE: amino acid
      ( C ) STRANDEDNESS: unknown
      ( D ) TOPOLOGY: unknown ( i i ) MOLECULE TYPE: protein ( x i ) SEQUENCE DESCRIPTION: SEQ ID NO:61:

Met Glu Glu Lys Leu Lys Ala
   1               5

( 2 ) INFORMATION FOR SEQ ID NO:62:

( i ) SEQUENCE CHARACTERISTICS:
      ( A ) LENGTH: 7 amino acids
      ( B ) TYPE: amino acid
      ( C ) STRANDEDNESS: unknown
      ( D ) TOPOLOGY: unknown ( i i ) MOLECULE TYPE: protein ( x i ) SEQUENCE DESCRIPTION: SEQ ID NO:62:

Met Glu Glu Lys Met Lys Ala
   1               5

( 2 ) INFORMATION FOR SEQ ID NO:63:

( i ) SEQUENCE CHARACTERISTICS:
      ( A ) LENGTH: 7 amino acids
      ( B ) TYPE: amino acid
      ( C ) STRANDEDNESS: unknown
      ( D ) TOPOLOGY: unknown ( i i ) MOLECULE TYPE: protein ( x i ) SEQUENCE DESCRIPTION: SEQ ID NO:63:

Leu Glu Glu Lys Leu Lys Lys
   1               5

( 2 ) INFORMATION FOR SEQ ID NO:64:

( i ) SEQUENCE CHARACTERISTICS:
      ( A ) LENGTH: 7 amino acids
      ( B ) TYPE: amino acid
      ( C ) STRANDEDNESS: unknown
      ( D ) TOPOLOGY: unknown ( i i ) MOLECULE TYPE: protein ( x i ) SEQUENCE DESCRIPTION: SEQ ID NO:64:

Met Glu Glu Lys Leu Lys Lys
   1               5

( 2 ) INFORMATION FOR SEQ ID NO:65:

( i ) SEQUENCE CHARACTERISTICS:
      ( A ) LENGTH: 7 amino acids
      ( B ) TYPE: amino acid
      ( C ) STRANDEDNESS: unknown
      ( D ) TOPOLOGY: unknown ( i i ) MOLECULE TYPE: protein ( x i ) SEQUENCE DESCRIPTION: SEQ ID NO:65:

Met Glu Glu Lys Met Lys Lys
   1               5

( 2 ) INFORMATION FOR SEQ ID NO:66:

( i ) SEQUENCE CHARACTERISTICS:
    ( A ) LENGTH: 7 amino acids
    ( B ) TYPE: amino acid
    ( C ) STRANDEDNESS: unknown
    ( D ) TOPOLOGY: unknown ( i i ) MOLECULE TYPE: protein ( x i ) SEQUENCE DESCRIPTION: SEQ ID NO:66:

```
Leu  Glu  Glu  Lys  Leu  Lys  Trp
 1                    5
```

( 2 ) INFORMATION FOR SEQ ID NO:67:

( i ) SEQUENCE CHARACTERISTICS:
    ( A ) LENGTH: 7 amino acids
    ( B ) TYPE: amino acid
    ( C ) STRANDEDNESS: unknown
    ( D ) TOPOLOGY: unknown ( i i ) MOLECULE TYPE: protein ( x i ) SEQUENCE DESCRIPTION: SEQ ID NO:67:

```
Met  Glu  Glu  Lys  Leu  Lys  Trp
 1                    5
```

( 2 ) INFORMATION FOR SEQ ID NO:68:

( i ) SEQUENCE CHARACTERISTICS:
    ( A ) LENGTH: 7 amino acids
    ( B ) TYPE: amino acid
    ( C ) STRANDEDNESS: unknown
    ( D ) TOPOLOGY: unknown ( i i ) MOLECULE TYPE: protein ( x i ) SEQUENCE DESCRIPTION: SEQ ID NO:68:

```
Met  Glu  Glu  Lys  Met  Lys  Trp
 1                    5
```

( 2 ) INFORMATION FOR SEQ ID NO:69:

( i ) SEQUENCE CHARACTERISTICS:
    ( A ) LENGTH: 7 amino acids
    ( B ) TYPE: amino acid
    ( C ) STRANDEDNESS: unknown
    ( D ) TOPOLOGY: unknown ( i i ) MOLECULE TYPE: protein ( x i ) SEQUENCE DESCRIPTION: SEQ ID NO:69:

```
Leu  Lys  Glu  Glu  Leu  Lys  Ala
 1                    5
```

( 2 ) INFORMATION FOR SEQ ID NO:70:

( i ) SEQUENCE CHARACTERISTICS:
    ( A ) LENGTH: 7 amino acids
    ( B ) TYPE: amino acid
    ( C ) STRANDEDNESS: unknown
    ( D ) TOPOLOGY: unknown ( i i ) MOLECULE TYPE: protein ( x i ) SEQUENCE DESCRIPTION: SEQ ID NO:70:

```
Met  Lys  Glu  Glu  Leu  Lys  Ala
 1                    5
```

( 2 ) INFORMATION FOR SEQ ID NO:71:

( i ) SEQUENCE CHARACTERISTICS:
        ( A ) LENGTH: 7 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:71:

Met  Lys  Glu  Glu  Met  Lys  Ala
    1                       5

( 2 ) INFORMATION FOR SEQ ID NO:72:

( i ) SEQUENCE CHARACTERISTICS:
        ( A ) LENGTH: 7 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:72:

Leu  Lys  Glu  Glu  Leu  Lys  Lys
    1                       5

( 2 ) INFORMATION FOR SEQ ID NO:73:

( i ) SEQUENCE CHARACTERISTICS:
        ( A ) LENGTH: 7 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:73:

Met  Lys  Glu  Glu  Leu  Lys  Lys
    1                       5

( 2 ) INFORMATION FOR SEQ ID NO:74:

( i ) SEQUENCE CHARACTERISTICS:
        ( A ) LENGTH: 7 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:74:

Met  Lys  Glu  Glu  Met  Lys  Lys
    1                       5

( 2 ) INFORMATION FOR SEQ ID NO:75:

( i ) SEQUENCE CHARACTERISTICS:
        ( A ) LENGTH: 7 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:75:

Leu  Lys  Glu  Glu  Leu  Lys  Trp
    1                       5

( 2 ) INFORMATION FOR SEQ ID NO:76:

( i ) SEQUENCE CHARACTERISTICS:
        ( A ) LENGTH: 7 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:76:

```
Met  Lys  Glu  Glu  Leu  Lys  Trp
1                   5
```

( 2 ) INFORMATION FOR SEQ ID NO:77:

( i ) SEQUENCE CHARACTERISTICS:
        ( A ) LENGTH: 7 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:77:

```
Met  Lys  Glu  Glu  Met  Lys  Trp
1                   5
```

( 2 ) INFORMATION FOR SEQ ID NO:78:

( i ) SEQUENCE CHARACTERISTICS:
        ( A ) LENGTH: 7 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:78:

```
Met  Glu  Asp  Lys  Met  Lys  Trp
1                   5
```

( 2 ) INFORMATION FOR SEQ ID NO:79:

( i ) SEQUENCE CHARACTERISTICS:
        ( A ) LENGTH: 7 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:79:

```
Leu  Lys  Glu  Glu  Met  Ala  Lys
1                   5
```

( 2 ) INFORMATION FOR SEQ ID NO:80:

( i ) SEQUENCE CHARACTERISTICS:
        ( A ) LENGTH: 7 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:80:

```
Leu  Lys  Glu  Glu  Met  Lys  Lys
1                   5
```

(2) INFORMATION FOR SEQ ID NO:81:

(i) SEQUENCE CHARACTERISTICS:
       (A) LENGTH: 7 amino acids
       (B) TYPE: amino acid
       (C) STRANDEDNESS: unknown
       (D) TOPOLOGY: unknown (ii) MOLECULE TYPE: protein (xi) SEQUENCE DESCRIPTION: SEQ ID NO:81:

Leu  Glu  Glu  Lys  Met  Lys  Val
   1                    5

(2) INFORMATION FOR SEQ ID NO:82:

(i) SEQUENCE CHARACTERISTICS:
       (A) LENGTH: 7 amino acids
       (B) TYPE: amino acid
       (C) STRANDEDNESS: unknown
       (D) TOPOLOGY: unknown (ii) MOLECULE TYPE: protein (xi) SEQUENCE DESCRIPTION: SEQ ID NO:82:

Met  Lys  Asp  Glu  Met  Trp  Lys
   1                    5

(2) INFORMATION FOR SEQ ID NO:83:

(i) SEQUENCE CHARACTERISTICS:
       (A) LENGTH: 28 amino acids
       (B) TYPE: amino acid
       (C) STRANDEDNESS: unknown
       (D) TOPOLOGY: unknown (ii) MOLECULE TYPE: protein (xi) SEQUENCE DESCRIPTION: SEQ ID NO:83:

Met  Glu  Glu  Lys  Leu  Lys  Lys  Met  Glu  Glu  Lys  Leu  Lys  Trp  Met  Glu
1                  5                        10                       15

Glu  Lys  Leu  Lys  Lys  Met  Glu  Glu  Lys  Leu  Lys  Trp
              20                       25

(2) INFORMATION FOR SEQ ID NO:84:

(i) SEQUENCE CHARACTERISTICS:
       (A) LENGTH: 130 base pairs
       (B) TYPE: nucleic acid
       (C) STRANDEDNESS: double
       (D) TOPOLOGY: linear (ii) MOLECULE TYPE: DNA (genomic)

(vi) ORIGINAL SOURCE:
       (B) STRAIN: E. coli
       (G) CELL TYPE: DH5 alpha (vii) IMMEDIATE SOURCE:
       (B) CLONE: segment 3 [seg 3]

(ix) FEATURE:
       (A) NAME/KEY: CDS
       (B) LOCATION: 3..116
       (D) OTHER INFORMATION: /function="synthetic seed storage
               protein"
               / product="protein"
               / gene="ssp"
               / standard_name="SSP-seg3"

(xi) SEQUENCE DESCRIPTION: SEQ ID NO:84:

```
CC ATG GAG GAG AAG ATG AAA AAG CTG GAA GAA AAG ATG AAG GCT ATG    47
   Met Glu Glu Lys Met Lys Lys Leu Glu Glu Lys Met Lys Ala Met
   1               5                   10                  15

GAG GAC AAG ATG AAA TGG CTT GAG GAA AAG ATG AAG AAG CTC GAA GAG   95
Glu Asp Lys Met Lys Trp Leu Glu Glu Lys Met Lys Lys Leu Glu Glu
            20                  25                  30

AAG ATG AAG GTC ATG AAG TGATAGGTAC CGAATTC                        130
Lys Met Lys Val Met Lys
            35
```

( 2 ) INFORMATION FOR SEQ ID NO:85:

( i ) SEQUENCE CHARACTERISTICS:
    ( A ) LENGTH: 37 amino acids
    ( B ) TYPE: amino acid
    ( D ) TOPOLOGY: linear ( i i ) MOLECULE TYPE: protein ( x i ) SEQUENCE DESCRIPTION: SEQ ID NO:85:

```
Met Glu Glu Lys Met Lys Lys Leu Glu Glu Lys Met Lys Ala Met Glu
1               5                   10                  15

Asp Lys Met Lys Trp Leu Glu Glu Lys Met Lys Lys Leu Glu Glu Lys
            20                  25                  30

Met Lys Val Met Lys
            35
```

( 2 ) INFORMATION FOR SEQ ID NO:86:

( i ) SEQUENCE CHARACTERISTICS:
    ( A ) LENGTH: 233 base pairs
    ( B ) TYPE: nucleic acid
    ( C ) STRANDEDNESS: double
    ( D ) TOPOLOGY: linear ( i i ) MOLECULE TYPE: DNA (genomic)

( v i ) ORIGINAL SOURCE:
    ( B ) STRAIN: E. coli
    ( G ) CELL TYPE: DH5 alpha ( v i i ) IMMEDIATE SOURCE:
    ( B ) CLONE: segment 34 [seg 34]

( i x ) FEATURE:
    ( A ) NAME/KEY: CDS
    ( B ) LOCATION: 3..221
    ( D ) OTHER INFORMATION: /function="synthetic storage protein
      / product="protein"
      / gene="ssp"
      / standard_name="SSP-seg34"

( x i ) SEQUENCE DESCRIPTION: SEQ ID NO:86:

```
CC ATG GAG GAG AAG ATG AAA AAG CTG GAA GAA AAG ATG AAG GCT ATG    47
   Met Glu Glu Lys Met Lys Lys Leu Glu Glu Lys Met Lys Ala Met
   1               5                   10                  15

GAG GAG AAG ATG AAA TGG CTT GAG GAA AAG ATG AAG AAG CTC GAA GAG   95
Glu Glu Lys Met Lys Trp Leu Glu Glu Lys Met Lys Lys Leu Glu Glu
            20                  25                  30

AAG ATG AAG GTC ATG GAG GAG AAG ATG AAA AAG CTC GAA GAA AAG ATG  143
Lys Met Lys Val Met Glu Glu Lys Met Lys Lys Leu Glu Glu Lys Met
            35                  40                  45

AAG GCA ATG GAA GAC AAA ATG AAG TGG CTT GAG GAG AAA ATG AAG AAG  191
Lys Ala Met Glu Asp Lys Met Lys Trp Leu Glu Glu Lys Met Lys Lys
        50                  55                  60

CTC GAA GAG AAG ATG AAG GTC ATG AAG TGATAGGTAC CGAAT             233
Leu Glu Glu Lys Met Lys Val Met Lys
```

6 5                              7 0

( 2 ) INFORMATION FOR SEQ ID NO:87:

( i ) SEQUENCE CHARACTERISTICS:
    ( A ) LENGTH: 72 amino acids
    ( B ) TYPE: amino acid
    ( D ) TOPOLOGY: linear ( i i ) MOLECULE TYPE: protein ( x i ) SEQUENCE DESCRIPTION: SEQ ID NO:87:

Met Glu Glu Lys Met Lys Lys Leu Glu Glu Lys Met Lys Ala Met Glu
 1               5                  10                  15

Glu Lys Met Lys Trp Leu Glu Glu Lys Met Lys Lys Leu Glu Glu Lys
                20                  25                  30

Met Lys Val Met Glu Glu Lys Met Lys Lys Leu Glu Glu Lys Met Lys
            35                  40                  45

Ala Met Glu Asp Lys Met Lys Trp Leu Glu Glu Lys Met Lys Lys Leu
        50              55                  60

Glu Glu Lys Met Lys Val Met Lys
65                  70

( 2 ) INFORMATION FOR SEQ ID NO:88:

( i ) SEQUENCE CHARACTERISTICS:
    ( A ) LENGTH: 84 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: misc_feature
    ( B ) LOCATION: 1..84
    ( D ) OTHER INFORMATION: /product="synthetic oligonucleotide"
     / standard_name="SM 96"

( x i ) SEQUENCE DESCRIPTION: SEQ ID NO:88:

GATGGAGGAA AAGATGAAGG CGATGGAGGA GAAAATGAAA GCTATGGAGG AAAAGATGAA 60

AGCGATGGAG GAGAAAATGA AGGC 84

( 2 ) INFORMATION FOR SEQ ID NO:89:

( i ) SEQUENCE CHARACTERISTICS:
    ( A ) LENGTH: 84 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: misc_feature
    ( B ) LOCATION: 1..84
    ( D ) OTHER INFORMATION: /product="synthetic oligonucleotide"
     / standard_name="SM 97"

( x i ) SEQUENCE DESCRIPTION: SEQ ID NO:89:

ATCGCCTTCA TTTTCTCCTC CATCGCTTTC ATCTTTTCCT CCATAGCTTT CATTTTCTCC 60

TCCATCGCCT TCATCTTTTC CTCC 84

( 2 ) INFORMATION FOR SEQ ID NO:90:

( i ) SEQUENCE CHARACTERISTICS:
    ( A ) LENGTH: 187 base pairs (B) TYPE: nucleic acid
(C) STRANDEDNESS: double
(D) TOPOLOGY: linear (i i) MOLECULE TYPE: DNA (genomic)

(v i) ORIGINAL SOURCE:
(B) STRAIN: E. coli
(G) CELL TYPE: DH5 alpha (i x) FEATURE:
(A) NAME/KEY: CDS
(B) LOCATION: 3..173
(D) OTHER INFORMATION: /function="synthetic storage protein
/ product="protein"
/ gene="ssp"
/ standard_name="SSP-3-5"

(x i) SEQUENCE DESCRIPTION: SEQ ID NO:90:

```
CC ATG GAG GAG AAG CTG AAG GCG ATG GAG GAG AAG CTG AAG GCG ATG      47
   Met Glu Glu Lys Leu Lys Ala Met Glu Glu Lys Leu Lys Ala Met
   1               5                   10                  15

GAG GAG AAG CTG AAG GCG ATG GAG GAG AAG CTG AAG GCG ATG GAG GAG      95
Glu Glu Lys Leu Lys Ala Met Glu Glu Lys Leu Lys Ala Met Glu Glu
            20                  25                  30

AAG CTG AAG GCG ATG GAG GAG AAG CTG AAG GCG ATG GAG GAA AAG ATG     143
Lys Leu Lys Ala Met Glu Glu Lys Leu Lys Ala Met Glu Glu Lys Met
        35                  40                  45

AAG GCG ATG GAA GAG AAG ATG AAG GCG TGATAGGTAC CGAATTC              187
Lys Ala Met Glu Glu Lys Met Lys Ala
        50                  55
```

(2) INFORMATION FOR SEQ ID NO:91:

(i) SEQUENCE CHARACTERISTICS:
(A) LENGTH: 56 amino acids
(B) TYPE: amino acid
(D) TOPOLOGY: linear (i i) MOLECULE TYPE: protein (x i) SEQUENCE DESCRIPTION: SEQ ID NO:91:

```
Met Glu Glu Lys Leu Lys Ala Met Glu Glu Lys Leu Lys Ala Met Glu
1               5                   10                  15

Glu Lys Leu Lys Ala Met Glu Glu Lys Leu Lys Ala Met Glu Glu Lys
            20                  25                  30

Leu Lys Ala Met Glu Glu Lys Leu Lys Ala Met Glu Glu Lys Met Lys
        35                  40                  45

Ala Met Glu Glu Lys Met Lys Ala
        50              55
```

(2) INFORMATION FOR SEQ ID NO:92:

(i) SEQUENCE CHARACTERISTICS:
(A) LENGTH: 61 base pairs
(B) TYPE: nucleic acid
(C) STRANDEDNESS: single
(D) TOPOLOGY: linear (i i) MOLECULE TYPE: DNA (genomic)

(i x) FEATURE:
(A) NAME/KEY: misc_feature
(B) LOCATION: 1..61
(D) OTHER INFORMATION: /product="synthetic oligonucleotide"
/ standard_name="SM 107"

(x i) SEQUENCE DESCRIPTION: SEQ ID NO:92:

CATGGAGGAG AAGATGAAAA AGCTCGAAGA GAAGATGAAG GTCATGAAGT GATAGGTACC   60

G 61

( 2 ) INFORMATION FOR SEQ ID NO:93:

( i ) SEQUENCE CHARACTERISTICS:
    ( A ) LENGTH: 61 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: misc_feature
    ( B ) LOCATION: 1..61
    ( D ) OTHER INFORMATION: /product="synthetic oligonucleotide"
      / standard_name="SM 106"

( x i ) SEQUENCE DESCRIPTION: SEQ ID NO:93:

AATTCGGTAC CTATCACTTC ATGACCTTCA TCTTCTCTTC GAGCTTTTC ATCTTCTCCT 60

C 61

( 2 ) INFORMATION FOR SEQ ID NO:94:

( i ) SEQUENCE CHARACTERISTICS:
    ( A ) LENGTH: 63 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: misc_feature
    ( B ) LOCATION: 1..63
    ( D ) OTHER INFORMATION: /product="synthetic oligonucleotide"
      / standard_name="SM 110"

( x i ) SEQUENCE DESCRIPTION: SEQ ID NO:94:

GCTGGAAGAA AAGATGAAGG CTATGGAGGA CAAGATGAAA TGGCTTGAGG AAAAGATGAA 60

GAA 63

( 2 ) INFORMATION FOR SEQ ID NO:95:

( i ) SEQUENCE CHARACTERISTICS:
    ( A ) LENGTH: 63 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: misc_feature
    ( B ) LOCATION: 1..63
    ( D ) OTHER INFORMATION: /product="synthetic oligonucleotide"
      / standard_name="SM 111"

( x i ) SEQUENCE DESCRIPTION: SEQ ID NO:95:

AGCTTCTTCA TCTTTTCCTC AAGCCATTTC ATCTTGTCCT CCATAGCCTT CATCTTTTCT 60

TCC 63

( 2 ) INFORMATION FOR SEQ ID NO:96:

( i ) SEQUENCE CHARACTERISTICS:
    ( A ) LENGTH: 130 base pairs
    ( B ) TYPE: nucleic acid
    ( C ) STRANDEDNESS: double
    ( D ) TOPOLOGY: linear ( i i ) MOLECULE TYPE: DNA (genomic)

( v i ) ORIGINAL SOURCE:
    ( B ) STRAIN: E. coli
    ( G ) CELL TYPE: DH5 alpha ( i x ) FEATURE:
    ( A ) NAME/KEY: CDS
    ( B ) LOCATION: 3..116
    ( D ) OTHER INFORMATION: /function="synthetic storage protein
        / product="protein"
        / gene="ssp"
        / standard_name="SSP-seg4"

( x i ) SEQUENCE DESCRIPTION: SEQ ID NO:96:

| | | | | | | | | | | | | | | | | |
|---|---|---|---|---|---|---|---|---|---|---|---|---|---|---|---|---|
| CC | ATG | GAG | GAG | AAG | ATG | AAA | AAG | CTC | GAA | GAA | AAG | ATG | AAG | GCA | ATG | 47 |
| | Met | Glu | Glu | Lys | Met | Lys | Lys | Leu | Glu | Glu | Lys | Met | Lys | Ala | Met | |
| | 1 | | | | 5 | | | | | 10 | | | | | 15 | |
| GAA | GAC | AAA | ATG | AAG | TGG | CTT | GAG | GAG | AAA | ATG | AAG | AAG | CTC | GAA | GAG | 95 |
| Glu | Asp | Lys | Met | Lys | Trp | Leu | Glu | Glu | Lys | Met | Lys | Lys | Leu | Glu | Glu | |
| | | | | 20 | | | | | 25 | | | | | 30 | | |
| AAG | ATG | AAG | GTC | ATG | AAG | TGATAGGTAC | CGAATTC | | | | | | | | | 130 |
| Lys | Met | Lys | Val | Met | Lys | | | | | | | | | | | |
| | | | | 35 | | | | | | | | | | | | |

( 2 ) INFORMATION FOR SEQ ID NO:97:

( i ) SEQUENCE CHARACTERISTICS:
        ( A ) LENGTH: 37 amino acids
        ( B ) TYPE: amino acid
        ( D ) TOPOLOGY: linear ( i i ) MOLECULE TYPE: protein ( x i ) SEQUENCE DESCRIPTION: SEQ ID NO:97:

| | | | | | | | | | | | | | | | |
|---|---|---|---|---|---|---|---|---|---|---|---|---|---|---|---|
| Met | Glu | Glu | Lys | Met | Lys | Lys | Leu | Glu | Glu | Lys | Met | Lys | Ala | Met | Glu |
| 1 | | | | 5 | | | | | 10 | | | | | 15 | |
| Asp | Lys | Met | Lys | Trp | Leu | Glu | Glu | Lys | Met | Lys | Lys | Leu | Glu | Glu | Lys |
| | | | 20 | | | | | 25 | | | | | 30 | | |
| Met | Lys | Val | Met | Lys | | | | | | | | | | | |
| | | | 35 | | | | | | | | | | | | |

( 2 ) INFORMATION FOR SEQ ID NO:98:

( i ) SEQUENCE CHARACTERISTICS:
        ( A ) LENGTH: 62 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..62
        ( D ) OTHER INFORMATION: /product="synthetic oligonucleotide"
            / standard_name="SM 112"

( x i ) SEQUENCE DESCRIPTION: SEQ ID NO:98:

GCTCGAAGAA AGATGAAGGC AATGGAAGAC AAAATGAAGT GGCTTGAGGA GAAAATGAAG   60

AA   62

( 2 ) INFORMATION FOR SEQ ID NO:99:

( i ) SEQUENCE CHARACTERISTICS:
        ( A ) LENGTH: 62 base pairs
        ( B ) TYPE: nucleic acid
        ( C ) STRANDEDNESS: single (D) TOPOLOGY: linear (ii) MOLECULE TYPE: DNA (genomic)

(ix) FEATURE:
    (A) NAME/KEY: misc_feature
    (B) LOCATION: 1..62
    (D) OTHER INFORMATION: /product="synthetic oligonucleotide"
        / standard_name="SM 113"

(xi) SEQUENCE DESCRIPTION: SEQ ID NO:99:

```
AGCTTCTTCA TTTTCTCCTC AAGCCACTTC ATTTTGTCTT CCATTGCCTT CATCTTTCTT    60
CG                                                                  62
```

(2) INFORMATION FOR SEQ ID NO:100:

(i) SEQUENCE CHARACTERISTICS:
        (A) LENGTH: 130 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (B) STRAIN: E. coli
        (G) CELL TYPE: DH5 alpha (ix) FEATURE:
        (A) NAME/KEY: CDS
        (B) LOCATION: 3..116
        (D) OTHER INFORMATION: /function="synthetic storage protein
            / product="protein"
            / gene="ssp"
            / standard_name="SSP-seg5"

(xi) SEQUENCE DESCRIPTION: SEQ ID NO:100:

```
CC ATG GAG GAG AAG ATG AAA AAG CTC AAG GAG GAA ATG GCT AAG ATG         47
   Met Glu Glu Lys Met Lys Lys Leu Lys Glu Glu Met Ala Lys Met
   1               5                   10                  15

AAA GAC GAA ATG TGG AAA CTG AAA GAG GAA ATG AAG AAG CTC GAA GAG        95
Lys Asp Glu Met Trp Lys Leu Lys Glu Glu Met Lys Lys Leu Glu Glu
                20                  25                  30

AAG ATG AAG GTC ATG AAG TGATAGGTAC CGAATTC                            130
Lys Met Lys Val Met Lys
            35
```

(2) INFORMATION FOR SEQ ID NO:101:

(i) SEQUENCE CHARACTERISTICS:
        (A) LENGTH: 37 amino acids
        (B) TYPE: amino acid
        (D) TOPOLOGY: linear (ii) MOLECULE TYPE: protein (xi) SEQUENCE DESCRIPTION: SEQ ID NO:101:

```
Met Glu Glu Lys Met Lys Lys Leu Lys Glu Glu Met Ala Lys Met Lys
1               5                   10                  15

Asp Glu Met Trp Lys Leu Lys Glu Glu Met Lys Lys Leu Glu Glu Lys
                20                  25                  30

Met Lys Val Met Lys
            35
```

(2) INFORMATION FOR SEQ ID NO:102:

(i) SEQUENCE CHARACTERISTICS:
        (A) LENGTH: 63 base pairs
        (B) TYPE: nucleic acid -continued ( C ) STRANDEDNESS: single
                ( D ) TOPOLOGY: linear ( i i ) MOLECULE TYPE: DNA (genomic)

( i x ) FEATURE:
                ( A ) NAME/KEY: misc_feature
                ( B ) LOCATION: 1..63
                ( D ) OTHER INFORMATION: /product="synthetic oligonucleotide"
                        / standard_name="SM 114"

( x i ) SEQUENCE DESCRIPTION: SEQ ID NO:102:

GCTCAAGGAG GAAATGGCTA AGATGAAAGA CGAAATCTGG AAACTGAAAG AGGAAATGAA 60

GAA 63

( 2 ) INFORMATION FOR SEQ ID NO:103:

( i ) SEQUENCE CHARACTERISTICS:
                ( A ) LENGTH: 63 base pairs
                ( B ) TYPE: nucleic acid
                ( C ) STRANDEDNESS: single
                ( D ) TOPOLOGY: linear ( i i ) MOLECULE TYPE: DNA (genomic)

( i x ) FEATURE:
                ( A ) NAME/KEY: misc_feature
                ( B ) LOCATION: 1..63
                ( D ) OTHER INFORMATION: /product="synthetic oligonucleotide"
                        / standard_name="SM 115"

( x i ) SEQUENCE DESCRIPTION: SEQ ID NO:103:

AGCTTCTTCA TTTCCTCTTT CAGTTTCCAC ATTTCGTCTT TCATCTTAGC CATTTCCTCC 60

TTG 63

( 2 ) INFORMATION FOR SEQ ID NO:104:

( i ) SEQUENCE CHARACTERISTICS:
                ( A ) LENGTH: 340 base pairs
                ( B ) TYPE: nucleic acid
                ( C ) STRANDEDNESS: double
                ( D ) TOPOLOGY: linear ( i i ) MOLECULE TYPE: DNA (genomic)

( v i ) ORIGINAL SOURCE:
                ( B ) STRAIN: E. coli
                ( G ) CELL TYPE: DH5 alpha ( v i i ) IMMEDIATE SOURCE:
                ( B ) CLONE: segment 534 [seg 534]

( i x ) FEATURE:
                ( A ) NAME/KEY: CDS
                ( B ) LOCATION: 3..326
                ( D ) OTHER INFORMATION: /function="synthetic seed storage
                        protein"
                        / product="protein"
                        / gene="ssp"
                        / standard_name="SSP-534"

( x i ) SEQUENCE DESCRIPTION: SEQ ID NO:104:

```
CC ATG GAG GAG AAG ATG AAA AAG CTC AAG GAG GAA ATG GCT AAG ATG      47
   Met Glu Glu Lys Met Lys Lys Leu Lys Glu Glu Met Ala Lys Met
   1               5                   10                  15

AAA GAC GAA ATG TGG AAA CTG AAA GAG GAA ATG AAG AAG CTC GAA GAG     95
Lys Asp Glu Met Trp Lys Leu Lys Glu Glu Met Lys Lys Leu Glu Glu
                20                  25                  30

AAG ATG AAG GTC ATG GAG GAG AAG ATG AAA AAG CTG GAA GAA AAG ATG    143
Lys Met Lys Val Met Glu Glu Lys Met Lys Lys Leu Glu Glu Lys Met
            35                  40                  45
```

```
AAG  GCT  ATG  GAG  GAC  AAG  ATG  AAA  TGG  CTT  GAG  GAA  AAG  ATG  AAG  AAG      191
Lys  Ala  Met  Glu  Asp  Lys  Met  Lys  Trp  Leu  Glu  Glu  Lys  Met  Lys  Lys
          50                       55                       60

CTC  GAA  GAG  AAG  ATG  AAG  GTC  ATG  GAG  GAG  AAG  ATG  AAA  AAG  CTC  GAA      239
Leu  Glu  Glu  Lys  Met  Lys  Val  Met  Glu  Glu  Lys  Met  Lys  Lys  Leu  Glu
          65                       70                       75

GAA  AAG  ATG  AAG  GCA  ATG  GAA  GAC  AAA  ATG  AAG  TGG  CTT  GAG  GAG  AAA      287
Glu  Lys  Met  Lys  Ala  Met  Glu  Asp  Lys  Met  Lys  Trp  Leu  Glu  Glu  Lys
80                       85                       90                       95

ATG  AAG  AAG  CTC  GAA  GAG  AAG  ATG  AAG  GTC  ATG  AAG  TGATAGGTAC              333
Met  Lys  Lys  Leu  Glu  Glu  Lys  Met  Lys  Val  Met  Lys
               100                      105

CGAATTC                                                                             340
```

( 2 ) INFORMATION FOR SEQ ID NO:105:

( i ) SEQUENCE CHARACTERISTICS:
        ( A ) LENGTH: 107 amino acids
        ( B ) TYPE: amino acid
        ( D ) TOPOLOGY: linear ( i i ) MOLECULE TYPE: protein ( x i ) SEQUENCE DESCRIPTION: SEQ ID NO:105:

```
Met  Glu  Glu  Lys  Met  Lys  Lys  Leu  Lys  Glu  Glu  Met  Ala  Lys  Met  Lys
 1                    5                        10                       15

Asp  Glu  Met  Trp  Lys  Leu  Lys  Glu  Glu  Met  Lys  Lys  Leu  Glu  Glu  Lys
               20                       25                       30

Met  Lys  Val  Met  Glu  Glu  Lys  Met  Lys  Lys  Leu  Glu  Glu  Lys  Met  Lys
          35                       40                       45

Ala  Met  Glu  Asp  Lys  Met  Lys  Trp  Leu  Glu  Glu  Lys  Met  Lys  Lys  Leu
     50                       55                       60

Glu  Glu  Lys  Met  Lys  Val  Met  Glu  Glu  Lys  Met  Lys  Lys  Leu  Glu  Glu
65                       70                       75                       80

Lys  Met  Lys  Ala  Met  Glu  Asp  Lys  Met  Lys  Trp  Leu  Glu  Glu  Lys  Met
               85                       90                       95

Lys  Lys  Leu  Glu  Glu  Lys  Met  Lys  Val  Met  Lys
               100                      105
```

( 2 ) INFORMATION FOR SEQ ID NO:106:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..16
        ( D ) OTHER INFORMATION: /function="PCR primer"
            / product="synthetic oligonucleotide"
            / standard_name="35S1"

( x i ) SEQUENCE DESCRIPTION: SEQ ID NO:106:

TTTGGAGGAG GACACG                                                                    16

( 2 ) INFORMATION FOR SEQ ID NO:107:

( i ) SEQUENCE CHARACTERISTICS:
        ( A ) LENGTH: 16 base pairs
        ( B ) TYPE: nucleic acid (C) STRANDEDNESS: single
(D) TOPOLOGY: linear (ii) MOLECULE TYPE: DNA (genomic)

(ix) FEATURE:
    (A) NAME/KEY: misc_feature
    (B) LOCATION: 1..16
    (D) OTHER INFORMATION: /function="PCR primer"
        / product="synthetic oligonucleotide"
        / standard_name="MEH15"

(xi) SEQUENCE DESCRIPTION: SEQ ID NO:107:

AAGAGAGAAT TGAGAC 16

(2) INFORMATION FOR SEQ ID NO:108:

(i) SEQUENCE CHARACTERISTICS:
    (A) LENGTH: 19 base pairs
    (B) TYPE: nucleic acid
    (C) STRANDEDNESS: single
    (D) TOPOLOGY: linear (ii) MOLECULE TYPE: DNA (genomic)

(ix) FEATURE:
    (A) NAME/KEY: misc_feature
    (B) LOCATION: 1..19
    (D) OTHER INFORMATION: /function="PCR primer"
        / product="synthetic oligonucleotide"
        / standard_name="SM 124"

(xi) SEQUENCE DESCRIPTION: SEQ ID NO:108:

GTACTACTAC TCTACTACT 19

(2) INFORMATION FOR SEQ ID NO:109:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: DNA (genomic)

(ix) FEATURE:
    (A) NAME/KEY: misc_feature
    (B) LOCATION: 1..21
    (D) OTHER INFORMATION: /function="PCR primer"
        / product="synthetic oligonucleotide"
        / standard_name="SM 125"

(xi) SEQUENCE DESCRIPTION: SEQ ID NO:109:

GAGCTCTTAC ACCTACATGC A 21

(2) INFORMATION FOR SEQ ID NO:110:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: DNA (genomic)

(ix) FEATURE:
    (A) NAME/KEY: misc_feature
    (B) LOCATION: 1..20
    (D) OTHER INFORMATION: /function="PCR primer"
        / product="synthetic oligonucleotide"
        / standard_name="SM 126"

(xi) SEQUENCE DESCRIPTION: SEQ ID NO:110:

CATCAAGAAC CAGTTCAATA                                                         20

( 2 ) INFORMATION FOR SEQ ID NO:111:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: unknown ( i i ) MOLECULE TYPE: protein ( i x ) FEATURE:
        ( A ) NAME/KEY: Protein
        ( B ) LOCATION: 1..14
        ( D ) OTHER INFORMATION: /label=name
              / note="base gene [(SSP5)2]"

( x i ) SEQUENCE DESCRIPTION: SEQ ID NO:111:

Met Glu Glu Lys Met Lys Ala Met Glu Glu Lys Met Lys Ala
 1               5                  10

( 2 ) INFORMATION FOR SEQ ID NO:112:

( i ) SEQUENCE CHARACTERISTICS:
        ( A ) LENGTH: 56 amino acids
        ( B ) TYPE: amino acid
        ( C ) STRANDEDNESS: unknown
        ( D ) TOPOLOGY: unknown ( i i ) MOLECULE TYPE: protein ( i x ) FEATURE:
        ( A ) NAME/KEY: Protein
        ( B ) LOCATION: 1..56
        ( D ) OTHER INFORMATION: /label=name
              / note="SSP-3- 5(A/E)"

( x i ) SEQUENCE DESCRIPTION: SEQ ID NO:112:

Met Glu Glu Lys Leu Lys Ala Met Glu Glu Lys Leu Lys Ala Met Glu
 1               5                  10                  15

Glu Lys Leu Lys Ala Met Glu Glu Lys Leu Lys Ala Met Glu Glu Lys
                20                  25                  30

Leu Lys Ala Met Glu Glu Lys Leu Lys Ala Met Glu Glu Lys Met Lys
            35                  40                  45

Glu Met Glu Glu Lys Met Lys Ala
            50                  55

( 2 ) INFORMATION FOR SEQ ID NO:113:

( i ) SEQUENCE CHARACTERISTICS:
        ( A ) LENGTH: 16 amino acids
        ( B ) TYPE: amino acid
        ( C ) STRANDEDNESS: unknown
        ( D ) TOPOLOGY: unknown ( i i ) MOLECULE TYPE: protein ( i x ) FEATURE:
        ( A ) NAME/KEY: Protein
        ( B ) LOCATION: 1..16
        ( D ) OTHER INFORMATION: /label=name
              / note="pSK34 base gene"

( x i ) SEQUENCE DESCRIPTION: SEQ ID NO:113:

Met Glu Glu Lys Met Lys Lys Leu Glu Glu Lys Met Lys Val Met Lys
 1               5                  10                  15